(12) United States Patent
Liou

(10) Patent No.: US 7,179,629 B2
(45) Date of Patent: Feb. 20, 2007

(54) REGULATION OF HUMAN SERINE/THREONINE KINASE

(75) Inventor: Jiing-Ren Liou, Belmont, MA (US)

(73) Assignee: Bayer Healthcare AG, Leverkusen (DE)

( * ) Notice: Subject to any disclaimer, the term of this patent is extended or adjusted under 35 U.S.C. 154(b) by 51 days.

(21) Appl. No.: 10/514,201

(22) PCT Filed: May 15, 2003

(86) PCT No.: PCT/EP03/05092

§ 371 (c)(1),
(2), (4) Date: May 4, 2005

(87) PCT Pub. No.: WO03/097822

PCT Pub. Date: Nov. 27, 2003

(65) Prior Publication Data

US 2005/0214768 A1 Sep. 29, 2005

Related U.S. Application Data

(60) Provisional application No. 60/432,628, filed on Dec. 12, 2002, provisional application No. 60/386,734, filed on Jun. 10, 2002, provisional application No. 60/380,294, filed on May 15, 2002.

(51) Int. Cl.
*C12N 9/12* (2006.01)

(52) U.S. Cl. .................................................. 435/194

(58) Field of Classification Search .................... None
See application file for complete search history.

(56) References Cited

FOREIGN PATENT DOCUMENTS

| WO | WO 02 18557 | 3/2002 |
|---|---|---|
| WO | WO 02 46384 | 6/2002 |

OTHER PUBLICATIONS

Cohen et al, Classification of protein-serine/threonine phosphatases: identification and quantitation in cell extracts. Methods Enzymol. 1991;201:389-98. Review.

Tonks et al, Purification and assay of CD45: an integral membrane protein-tyrosine phosphatase. Methods Enzymol. 1991;201:442-51.

Database Embl 'On line! EBI; SEQ ID No.: 2 from WO0218557 Mar. 7, 2002 Bandman et al.: "Human PKIN-2 protein" Database accession No. AAE21707 XP002248930.

Leung Thomas et al.: "Myotonic dystrophy kinase-related Cdc42-binding kinase acts as a Cdc42 effector in promoting cytoskeletal reorganization." Molecular and Cellular Biology, vol. 18, No. 1, Jan. 1998, pp. 130-140, XP002248927 ISSN: 0270-7306, p. 131, paragraph 1; figures 2,3.

Database Swall 'On line? EBI; Jun. 1, 1998, Leung T: "Mytonic dystrophy kinase-related Cdc42-binding kinase" Database accession No. 054874 XP002248931.

Dong Jing-Ming et al: "Cdc42 antagonizes inductive action of cAMP on cell shape, via effects of the myotonic dystrophy kinase-related Cdc42-binding kinase (MRCK)on myosin light chain phosphorylation." European Journal of Cell Biology, vol. 81, No. 4, Apr. 2002 pp. 231-242, XP002248928 ISSN: 0171-9335.

Tan Ivan et al: "Intermolecular and Intramolecular interactions regulate catalytic activity of myotonic dystrophy kinase-related Cdc42-binding kinase alpha." Molecular and Cellular Biology, vol. 21, No. 8, Apr. 2001, pp. 2767-2778, XP002248929 ISSN: 0270-7306.

Database Embl 'On line!EBI;SEQ ID NO: 19 from WO02/46384, Jun. 3, 2002, Yue et al (Incyte Genomics): Human kinase and phosphatase-19 (KAP-19) protein" Database accession No. AAE25099, XP002248932.

Tan I et al: "Genomic organization of human myotonic dystrophy kinase-related Cdc42-binding kinase alpha reveals multiple alternative splicing and functional diversity" Gene: An International Journal of Genes and Genomes, Elsevier Science Publishers, Barking, GB, vol. 304, Jan. 30, 2003, pp. 107-115, XP004406357 ISSN: 0378-1119.

*Primary Examiner*—Sheridan Swope
(74) *Attorney, Agent, or Firm*—Banner & Witcoff, Ltd.

(57) ABSTRACT

Reagents that regulate human serine/threonine kinase and reagents which bind to human serine/threonine kinase gene products can play a role in preventing, ameliorating, or correcting dysfunctions or diseases including, but not limited to, cancer, diabetes, neurological disorders, cardiovascular disorders, musculo-skeletal disorders, inflammatory disorders, genitourological disorders, and respiratory disorders (e.g., asthma and COPD).

1 Claim, No Drawings

US 7,179,629 B2

REGULATION OF HUMAN SERINE/THREONINE KINASE

This application is a National Stage application of co-pending PCT application PCT/EPO3/05092 filed May 15, 2003, which was published in English under PCT Article 21(2) on Nov. 27, 2003, and which claims the benefit of U.S. provisional application Ser. No. 60/380,294 filed May 15, 2002, Ser. No. 60/386,734 filed Jun. 10, 2002, and Ser. No. 60/432,628 filed Dec. 12, 2002.

FIELD OF THE INVENTION

The invention relates to the regulation of human serine/threonine kinase.

BACKGROUND OF THE INVENTION

Intercellular signaling regulates a variety of important biological functions. For example, transforming growth factor type beta (TGF-β) regulates the proliferation and differentiation of a variety of cell types binding to and activating cell surface receptors which possess serine-threonine kinase activity. Atfi et al. (*Proc. Natl. Acad. Sci. U.S.A.* 92, 12110–04, 1995) have shown that TGF-β activates a 78-kDa protein (p78) serine/threonine kinase; the p78 kinase was activated only in cells for which TGF-β acts as a growth inhibitory factor. Because of the important functions of kinases such as p78, there is a need in the art to identify new kinases and methods of regulating these new kinases for therapeutic effects.

It is an object of the invention to provide reagents and methods of regulating a human serine/threonine kinase. This and other objects of the invention are provided by one or more of the embodiments described below.

The invention relates to an isolated polynucleotide from the group consisting of:
a) a polynucleotide encoding a Serine/threonine kinase polypeptide comprising an amino acid sequence selected from the group consisting of:
   amino acid sequences which are at least about 89% identical to
   the amino acid sequence shown in SEQ ID NO: 2; and
   the amino acid sequence shown in SEQ ID NO: 2.
b) a polynucleotide comprising the sequence of SEQ ID NO: 1;
c) a polynucleotide which hybridizes under stringent conditions to a poly-nucleotide specified in (a) and (b) and encodes a Serine/threonine kinase polypeptide;
d) a polynucleotide the sequence of which deviates from the polynucleotide sequences specified in (a) to (c) due to the degeneration of the genetic code and encodes a Serine/threonine kinase polypeptide; and
e) a polynucleotide which represents a fragment, derivative or allelic variation of a polynucleotide sequence specified in (a) to (d) and encodes a Serine/threonine kinase polypeptide.

A novel human serine/threonine kinase is a discovery of the present invention. Human serine/threonine kinase comprises the amino acid sequence shown m SEQ ID NO: 2. A coding sequence for human serine/threonine kinase is shown in SEQ ID NO: 1. This sequence is located on chromosome 1q42. A homologues sequence from rat (*rattus norvegicus*) is shown in SEQ ID NO: 3. Related ESTs (SEQ ID NOS: 4–20) are expressed in prostate (adenocarcinoma, cell line), liver (adenocarcinoma, cell line), eye (retinoblastoma), pancreas (islets of Langerhans), brain (anaplastic oligodendroglioma, schizophrenic brain S-11 frontal lobe), placenta, melanocytes, and uterus (serous papillary carcinoma, high grade).

The protein kinase domain, a phorbol ester/diacylglycerol binding domain, protein kinase C terminal domain, PH domain, and CNH domain are found. The 3D structure infers LBRI 481 to a cAMP-dependent protein kinase (catalytic subunit).

Furthermore, ATP-binding region, kinase active site. Active site D residue and sites of ATP-binding, and NP-binding are also found in SEQ ID NO: 2.

Human serine/threonine kinase of the invention is expected to be useful for the same purposes as previously identified serine/threonine kinases. Human serine/threonine kinase is believed to be useful in therapeutic methods to treat disorders such as cancer, diabetes, neurological disorders, cardiovascular disorders, musculo-skeletal disorders, inflammatory disorders, genitourological disorders, and respiratory disorders (e.g., asthma and COPD). Human serine/threonine kinase also can be used to screen for human serine/threonine kinase activators and inhibitors.

One embodiment of the present invention is an expression vector containing any polynucleotide of the present invention.

Yet another embodiment of the present invention is a host cell containing any expression vector of the present invention.

Still another embodiment of the present invention is a substantially purified Serine/threonine kinase polypeptide encoded by any polynucleotide of the present invention.

Even another embodiment of the present invention is a method of producing a Serine/threonine kinase polypeptide of the present invention, wherein the method comprises the following steps:
a. culturing the host cells of the present invention under conditions suitable for the expression of the Serine/threonine kinase polypeptide; and
b. recovering the Serine/threonine kinase polypeptide from the host cell culture.

Yet another embodiment of the present invention is a method for detecting a polynucleotide encoding a Serine/threonine kinase polypeptide in a biological sample comprising the following steps:
a. hybridizing any polynucleotide of the present invention to a nucleic acid material of a biological sample, thereby forming a hybridization complex; and
b. detecting said hybridization complex.

Still another embodiment of the present invention is a method for detecting a polynucleotide of the present invention or a Serine/threonine kinase polypeptide of the present invention comprising the steps of:
a. contacting a biological sample with a reagent which specifically interacts with the polynucleotide or the Serine/threonine kinase polypeptide and
b. detecting the interaction Even another embodiment of the present invention is a diagnostic kit for conducting any method of the present invention.

Yet another embodiment of the present invention is a method of screening for agents which decrease the activity of a Serine/threonine kinase, comprising the steps of:
a. contacting a test compound with a Serine/threonine kinase polypeptide encoded by any polynucleotide of the present invention;
b. detecting binding of the test compound to the Serine/threonine kinase polypeptide, wherein a test compound which binds to the polypeptide is identified as a potential therapeutic agent for decreasing the activity of a Serine/threonine kinase.

Still another embodiment of the present invention is a method of screening for agents which regulate the activity of a Serine/threonine kinase, comprising the steps of:

a. contacting a test compound with a Serine/threonine kinase polypeptide encoded by any polynucleotide of the present invention; and b. detecting a Serine/threonine kinase activity of the polypeptide, wherein a test compound which increases the Serine/threonine kinase activity is identified as a potential therapeutic agent for increasing the activity of the Serine/threonine kinase, and wherein a test compound which decreases the Serine/threonine, kinase activity of the polypeptide is identified as a potential therapeutic agent for decreasing the activity of the Serine/threonine kinase.

Even another embodiment of the present invention is a method of screening for agents which decrease the activity of a Serine/threonine kinase, comprising the step of:

contacting a test compound with any polynucleotide of the present invention and detecting binding of the test compound to the polynucleotide, wherein a test compound which binds to the polynucleotide is identified as a potential therapeutic agent for decreasing the activity of Serine/threonine kinase.

Yet another embodiment of the present invention is a method of reducing the activity of a Serine/threonine kinase, comprising the step of:

contacting a cell with a reagent which specifically binds to any polynucleotide of the present invention or any Serine/threonine kinase polypeptide of the present invention, whereby the activity of Serine/threonine kinase is reduced.

Still another embodiment of the present invention is a reagent that modulates the activity of a Serine/threonine kinase polypeptide or a polynucleotide wherein said reagent is identified by any methods of the present invention.

Even another embodiment of the present invention is a pharmaceutical composition, comprising:

an expression vector of the present invention or a reagent of the present invention and a pharmaceutically-acceptable carrier.

Yet another embodiment of the present invention is the use of an expression vector of the present invention or a reagent of the present invention for modulating the activity of a Serine/threonine kinase in a disease, preferably cancer, diabetes, a neurological disorder, a cardiovascular disorder, a musculo-skeletal disorder, a inflammatory disorder, a genitourological disorder or a respiratory disorder (e.g., asthma and COPD).

The invention thus provides a human serine/threonine kinase that can be used to identify test compounds that may act, for example, as activators or inhibitors at the enzyme's active site. Human serine/threonine kinase and fragments thereof also are useful in raising specific antibodies that can block the enzyme and effectively reduce its activity.

Polypeptides

Human serine/threonine kinase polypeptides according to the invention comprise at least 6, 10, 15, 20, 25, 50, 75, 100, 125, 150, 175, 200, 225, 250, 275, 300, 400, 500, 600, 700, 800, 900, 1000, 1100, 1200, 1300, 1400, 1500, 1600, 1700, or 1732 contiguous amino acids selected from the amino acid sequence shown in SEQ ID NO: 2 or a biologically active variant thereof, as defined below. A serine/threonine kinase polypeptide of the invention therefore can be a portion of a serine/threonine kinase protein, a full-length serine/threonine kinase protein, or a fusion protein comprising all or a portion of a serine/threonine kinase protein.

Biologically Active Variants

Human serine/threonine kinase polypeptide variants which are biologically active, e.g., retain enzymatic activity also are human serine/threonine kinase polypeptides. Preferably, naturally or non-naturally occurring human serine/threonine kinase polypeptide variants have amino acid sequences which are at least about 89, 90, 96, 97, 98, or 99% identical to the amino acid sequence shown in SEQ ID NO: 2 or a fragment thereof. Percent identity between a putative human serine/threonine kinase polypeptide variant and an amino acid sequence of SEQ ID NO: 2 is determined by conventional methods. See, for example, Altschul et al., *Bull. Math. Bio.* 48:603 (1986), and Henikoff & Henikoff, *Proc. Natl. Acad Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff & Henikoff, 1992.

Those skilled in the art appreciate that there are many established algorithms available to align two amino acid sequences. The "FASTA" similarity search algorithm of Pearson & Lipman is a suitable protein alignment method for examining the level of identity shared by an amino acid sequence disclosed herein and the amino acid sequence of a putative variant. The FASTA algorithm is described by Pearson & Lipman, *Proc. Nat'l Acad Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO: 2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman & Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a human serine/threonine kinase polypeptide can be found using computer programs well known in the art, such as DNASTAR software.

The invention additionally, encompasses serine/threonine kinase polypeptides that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques including, but not limited, to specific chemical cleavage by cyanogen bromide, trypsin, chymotrypsin, papain, V8 protease, NaBH$_4$, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The serine/threonine kinase polypeptides may also be modified with a detectable label, such as an enzymatic, fluorescent, isotopic or affinity label to allow for detection and isolation of the protein.

The invention also provides chemically modified derivatives of serine/threonine kinase polypeptides that may provide additional advantages such as increased solubility, stability and circulating time of the polypeptide, or decreased immunogenicity (see U.S. Pat. No. 4,179,337). The chemical moieties for derivitization can be selected from water soluble polymers such as polyethylene glycol ethylene glycol/propylene glycol copolymers, carboxymethylcellulose, dextran, polyvinyl alcohol, and the like. The polypeptides can be modified at random or predetermined positions within the molecule and can include one, two, three, or more attached chemical moieties.

Whether an amino acid change or a polypeptide modification results in a biologically active serine/threonine kinase polypeptide can readily be determined by assaying for enzymatic activity, as described for example, in Trost et al., *J. Biol. Chem.* 275, 7373–77, 2000; Hayashi et al., *Biochem. Biophys. Res. Commun.* 264, 449–56, 1999; Masure et al., *Eur. J. Biochem.* 265, 353–60, 1999; and Mukhopadhyay et al., *J. Bacteriol.* 181, 6615–22, 1999.

Fusion Proteins

Fusion proteins are useful for generating antibodies against serine/threonine kinase polypeptide amino acid sequences and for use in various assay systems. For example, fusion proteins can be used to identify proteins that interact with portions of a human serine/threonine kinase polypeptide. Protein affinity chromatography or library-based assays for protein-protein interactions, such as the yeast two-hybrid or phage display systems, can be used for this purpose. Such methods are well known in the art and also can be used as drug screens.

A human serine/threonine kinase polypeptide fusion protein comprises two polypeptide segments fused together by means of a peptide bond. The first polypeptide segment comprises at least 6, 10, 15, 20, 25, 50, 75, 100, 125, 150, 175, 200, 225, 250, 275, 300, 400, 500, 600, 700, 800, 900, 1000, 1100, 1200, 1300, 1400, 1500, 1600, 1700, or 1732 contiguous amino acids of SEQ ID NO: 2 or of a biologically active variant, such as those described above. The first polypeptide segment also can comprise full-length serine/threonine kinase protein.

The second polypeptide segment can be a full-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT).

Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the serine/threonine kinase polypeptide-encoding sequence and the heterologous protein sequence, so that the serine/threonine kinase polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO: 1 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human serine/threonine kinase polypeptide can be obtained using serine/threonine kinase polypeptide polynucleotides (described below) to make suitable probes or primers for screening cDNA expression libraries from other species, such as mice, monkeys, or yeast, identifying cDNAs which encode homologs of serine/threonine kinase polypeptide, and expressing the cDNAs as is known in the art.

Polynucleotides

A human serine/threonine kinase polynucleotide can be single- or double-stranded and comprises a coding sequence or the complement of a coding sequence for a serine/threonine kinase polypeptide. A coding sequence for human serine/threonine kinase is shown in SEQ ID NO: 1.

Degenerate nucleotide sequences encoding human serine/threonine kinase polypeptides, as well as homologous nucleotide sequences which are at least about 50, 55, 60, 65, 70, preferably about 75, 90, 96, 98, or 99% identical to the nucleotide sequence shown in SEQ ID NO: 1 or its complement also are serine/threonine kinase polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of serine/threonine kinase polynucleotides that encode biologically active serine/threonine kinase polypeptides also are serine/threonine kinase polynucleotides. Polynucleotide fragments comprising at least 8, 9, 10, 11, 12, 15, 20, or 25 contiguous nucleotides of SEQ ID NO: 1 or its complement also are serine/threonine kinase polynucleotides. These fragments can be used, for example, as hybridization probes or as antisense oligonucleotides.

Identification of Polynucleotide Variants and Homologs

Variants and homologs of the serine/threonine kinase polynucleotides described above also are serine/threonine kinase polynucleotides. Typically, homologous serine/threonine kinase polynucleotide sequences can be identified by hybridization of candidate polynucleotides to known serine/threonine kinase polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the serine/threonine kinase polynucleotides disclosed herein also can be identified by making suitable probes or primers and screening cDNA expression libraries from other species, such as mice, monkeys, or yeast. Human variants of serine/threonine kinase polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human serine/threonine kinase polynucleotides or serine/threonine kinase polynucleotides of other species can therefore be identified by hybridizing a putative homologous serine/threonine kinase polynucleotide with a polynucleotide having a nucleotide sequence of SEQ ID NO: 1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to serine/threonine kinase polynucleotides or their complements following stringent hybridization and/or wash conditions also are serine/threonine kinase polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a serine/threonine kinase polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% G+C) - 0.63(\% \text{ formamide}) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A human serine/threonine kinase polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated serine/threonine kinase polynucleotides. For example, restriction enzymes and probes can be used to isolate polynucleotide fragments, which comprise serine/threonine kinase nucleotide sequences. Isolated polynucleotides are in preparations that are free or at least 70, 80, or 90% free of other molecules.

Human serine/threonine kinase cDNA molecules can be made with standard molecular biology techniques, using serine/threonine kinase mRNA as a template. Human serine/threonine kinase cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesize serine/threonine kinase polynucleotides. The degeneracy of the genetic code allows alternate nucleotide sequences to be synthesized which will encode a human serine/threonine kinase polypeptide having, for example, an amino acid sequence shown in SEQ ID NO: 2 or a biologically active variant thereof.

Extending Polynucleotides

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus. Sarkar, *PCR Methods Applic.* 2, 318–322, 1993; Triglia et al., *Nucleic Acids Res.* 16, 8186, 1988; Lagerstrom et al., *PCR Methods Applic.* 1, 111–119, 1991; Parker et al., *Nucleic Acids Res.* 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). See WO 01/98340

Obtaining Polynucleotides

Human serine/threonine kinase polypeptides can be obtained, for example, by purification from human cells, by expression of serine/threonine kinase polynucleotides, or by direct chemical synthesis.

Protein Purification

Human serine/threonine kinase polypeptides can be purified from any human cell which expresses the receptor, including host cells which have been transfected with serine/threonine kinase polynucleotides. A purified serine/threonine kinase polypeptide, is separated from other compounds that normally associate with the serine/threonine kinase polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis.

A preparation of purified serine/threonine kinase polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express a human serine/threonine kinase polynucleotide, the polynucleotide can be inserted into an expression vector which contains the necessary elements for the transcription and translation of the inserted coding sequence. Methods which are well known to those skilled in the art can be used to construct expression vectors containing sequences encoding serine/threonine kinase polypeptides and appropriate transcriptional and translational control elements. These methods include in vitro recombinant DNA techniques, synthetic techniques, and in vivo genetic recombination. Such techniques are described, for example, in Sambrook et al. (i989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a human serine/threonine kinase polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems. See WO 01/98340.

Host Cells

A host cell strain can be chosen for its ability to modulate the expression of the inserted sequences or to process the expressed serine/threonine kinase polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells that have specific cellular machinery and characteristic mechanisms for post-translational activities (e.g., CHO, HeLa, MDCK, HEK293, and WI38) are available from the American Type Culture Collection (ATCC; 10801 University Boulevard, Manassas, Va. 20110-2209) and can be chosen to ensure the correct modification and processing of the foreign protein. See WO 01/98340.

Alternatively, host cells which contain a human serine/threonine kinase polynucleotide and which express a human serine/threonine kinase polypeptide can be identified by a variety of procedures known to those of skill in the art. Examples include enzyme-linked immunosorbent assay (ELISA), radioimmunoassay (RIA), and fluorescence activated cell sorting (FACS). Hampton et al., SEROLOGICAL METHODS: A LABORATORY MANUAL, APS Press, St. Paul, Minn., 1990) and Maddox et al., J. Exp. Med 158, 1211–1216, 1983). See WO 01/98340.

A wide variety of labels and conjugation techniques are known by those skilled in the art and can be used in various nucleic acid and amino acid assays. Means for producing labeled hybridization or PCR probes for detecting sequences related to polynucleotides encoding serine/threonine kinase polypeptides include oligolabeling, nick translation, end-labeling, or PCR amplification using a labeled nucleotide. Alternatively, sequences encoding a human serine/threonine kinase polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding a human serine/threonine kinase polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode serine/threonine kinase polypeptides can be designed to contain signal sequences which direct secretion of soluble serine/threonine kinase polypeptides through a prokaryotic or eukaryotic cell membrane or which direct the membrane insertion of membrane-bound serine/threonine kinase polypeptide. See WO 01/98340.

Chemical Synthesis

Sequences encoding a human serine/threonine kinase polypeptide can be synthesized, in whole or in part, using chemical methods well known in the art (see Caruthers et al., Nucl. Acids Res. Symp. Ser. 215–223, 1980; Horn et al. Nucl. Acids Res. Symp. Ser. 225–232, 1980). Alternatively, a human serine/threonine kinase polypeptide itself can be produced using chemical methods to synthesize its amino acid sequence, such as by direct peptide synthesis using solid-phase techniques (Merrifield, J. Am. Chem. Soc. 85, 2149–2154, 1963; Roberge et al., Science 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of serine/threonine kinase polypeptides can be separately synthesized and combined using chemical methods to produce a full-length molecule. See WO 01/98340.

As will be understood by those of skill in the art, it may be advantageous to produce serine/threonine kinase polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter serine/threonine kinase polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a human serine/threonine kinase polypeptide. "Antibody" as used herein includes intact immunoglobulin molecules, as well as fragments thereof, such as Fab, F(ab')$_2$, and Fv, which are capable of binding an epitope of a human serine/threonine kinase polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a human serine/threonine kinase polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the immunogen.

Typically, an antibody that specifically binds to a human serine/threonine kinase polypeptide provides a detection signal at least 5-, 10-, or 20-fold higher than a detection signal provided with other proteins when used in an immunochemical assay. Preferably, antibodies that specifically bind to serine/threonine kinase polypeptides do not detect other proteins in immunochemical assays and can immunoprecipitate a human serine/threonine kinase polypeptide from solution. See WO 01/98340.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of serine/threonine kinase gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of serine/threonine kinase gene expression can be obtained by designing antisense oligonucleotides that will form duplexes to the control, 5', or regulatory regions of the serine/threonine kinase gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes. See WO 01/98340.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a human serine/threonine kinase polynucleotide can be used to generate ribozymes that will specifically bind to mRNA transcribed from the serine/threonine kinase polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201). See WO 01/98340.

Differentially Expressed Genes

Described herein are methods for the identification of genes whose products interact with human serine/threonine kinase. Such genes may represent genes that are differentially expressed in disorders including, but not limited to, cancer, diabetes, neurological disorders, cardiovascular disorders, musculo-skeletal disorders, inflammatory disorders, genitourological disorders, and respiratory disorders (e.g., asthma and COPD). Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human serine/threonine kinase gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., Proc. Natl. Acad Sci. U.S.A. 85, 208–12, 1988), subtractive hybridization (Hedrick et al., Nature 308, 149–53; Lee et al., Proc. Natl. Acad Sci. U.S.A. 88, 2825, 1984), and, preferably, differential display (Liang & Pardee, Science 257, 967–71, 1992; U.S. Pat. No. 5,262,311).

The differential expression information may itself suggest relevant methods for the treatment of disorders involving the human serine/threonine kinase. For example, treatment may include a modulation of expression of the differentially expressed genes and/or the gene encoding the human serine/threonine kinase. The differential expression information may indicate whether the expression or activity of the differentially expressed gene or gene product or the human serine/threonine kinase gene or gene product are up-regulated or down-regulated.

Screening Methods

The invention provides assays for screening test compounds that bind to or modulate the activity of a human serine/threonine kinase polypeptide or a human serine/threonine kinase polynucleotide. A test compound preferably binds to a human serine/threonine kinase polypeptide or polynucleotide. More preferably, a test compound decreases or increases enzymatic activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412–421, 1992), or on beads (Lam, Nature 354, 82–84, 1991), chips (Fodor, Nature 364, 555–556, 1993), bacteria or spores (Ladner, U.S. Pat. No. 5,223,409), plasmids (Cull et al., Proc. Natl. Acad. Sci. U.S.A. 89, 1865–1869, 1992), or phage (Scott & Smith, Science 249, 386–390, 1990; Devlin, Science 249, 404–406, 1990); Cwirla et al., Proc. Natl. Acad. Sci. 97, 6378–6382, 1990; Felici, J. Mol. Biol. 222, 301–310, 1991; and Ladner, U.S. Pat. No. 5,223,409).

High Throughput Screening

Test compounds can be screened for the ability to bind to serine/threonine kinase polypeptides or polynucleotides or to affect serine/threonine kinase activity or serine/threonine kinase gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., Proc. Natl. Acad. Sci. USA. 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., Molecular Diversity 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule that binds to and occupies, for example, the active site of the serine/threonine kinase polypeptide, such that normal biological activity is prevented. Examples of such small molecules include, but are not limited to, small peptides or peptide-like molecules.

In binding assays, either the test compound or the serine/threonine kinase polypeptide can comprise a detectable label, such as a fluorescent, radioisotopic, chemiluminescent, or enzymatic label, such as horseradish peroxidase, alkaline phosphatase, or luciferase. Detection of a test compound that is bound to the serine/threonine kinase polypeptide can then be accomplished, for example, by direct counting of radioemmission, by scintillation counting, or by determining conversion of an appropriate substrate to a detectable product.

Alternatively, binding of a test compound to a human serine/threonine kinase polypeptide can be determined without labeling either of the interactants. For example, a microphysiometer can be used to detect binding of a test compound with a human serine/threonine kinase polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a human serine/threonine kinase polypeptide (McConnell et al., *Science* 257, 1906–1912, 1992).

Determining the ability of a test compound to bind to a human serine/threonine kinase polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a human serine/threonine kinase polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with -the serine/threonine kinase polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a human serine/threonine kinase polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with the serine/threonine kinase polypeptide.

It may be desirable to immobilize either the serine/threonine kinase polypeptide (or polynucleotide) or the test compound to facilitate separation of bound from unbound forms of one or both of the interactants, as well as to accommodate automation of the assay. Thus, either the serine/threonine kinase polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a human serine/threonine kinase polypeptide (or polynucleotide) can be accomplished in any vessel suitable for containing the reactants. Examples of such vessels include microtiter plates, test tubes, and microcentrifuge tubes.

In one embodiment, the serine/threonine kinase polypeptide is a fusion protein comprising a domain that allows the serine/threonine kinase polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed serine/threonine kinase polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a human serine/threonine kinase polypeptide (or polynucleotide) or a test compound can be immobilized utilizing conjugation of biotin and streptavidin. Biotinylated serine/threonine kinase polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a serine/threonine kinase polypeptide, polynucleotide, or a test compound, but which do not interfere with a desired binding site, such as the active site of the serine/threonine kinase polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the serine/threonine kinase polypeptide or test compound, enzyme-linked assays which rely on detecting an activity of the serine/threonine kinase polypeptide, and SDS gel electrophoresis under non-reducing conditions.

Screening for test compounds which bind to a human serine/threonine kinase polypeptide or polynucleotide also can be carried out in an intact cell. Any cell which comprises a serine/threonine kinase polypeptide or polynucleotide can be used in a cell-based assay system. A serine/threonine kinase polynucleotide can be naturally occurring in the cell or can be introduced using techniques such as those described above. Binding of the test compound to a serine/threonine kinase polypeptide or polynucleotide is determined as described above.

Enzymatic Activity

Test compounds can be tested for the ability to increase or decrease the enzymatic activity of a human serine/threonine kinase polypeptide. Enzymatic activity can be measured, for example, as described in Trost et al., *J. Biol. Chem.*, 275, 7373–77, 2000; Hayashi et al., *Biochem. Biophys. Res. Commun.* 264, 449–56, 1999; Masure et al., *Eur. J. Biochem.* 265, 353–60, 1999; and Mukhopadhyay et al., *J. Bacteriol.* 181, 6615–22, 1999.

Enzyme assays can be carried out after contacting either a purified serine/threonine kinase polypeptide, a cell membrane preparation, or an intact cell with a test compound. A test compound that decreases enzymatic activity of a human serine/threonine kinase polypeptide by at least about 10, preferably about 50, more preferably about 75, 90, or 100% is identified as a potential therapeutic agent for decreasing serine/threonine kinase activity. A test compound which increases enzymatic activity of a human serine/threonine kinase polypeptide by at least about 10, preferably about 50, more preferably about 75, 90, or 100% is identified as a potential therapeutic agent for increasing human serine/threonine kinase activity.

Gene Expression

In another embodiment, test compounds that increase or decrease serine/threonine kinase gene expression are identified. A serine/threonine kinase polynucleotide is contacted with a test compound, and the expression of an RNA or polypeptide product of the serine/threonine kinase polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of serine/threonine kinase mRNA or polypeptide expression in the cells can be determined by methods well known in the art for detecting mRNA or polypeptide. Either qualitative or quantitative methods can be used. The presence of polypeptide products of a human serine/threonine kinase polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a human serine/threonine kinase polypeptide.

Such screening can be carried out either in a cell-free assay system or in an intact cell. Any cell that expresses a human serine/threonine kinase polynucleotide can be used in a cell-based assay system. The serine/threonine kinase polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions that can be administered to a patient to achieve a therapeutic effect. Pharmaceutical compositions of the invention can comprise, for example, a human serine/threonine kinase polypeptide, serine/threonine kinase polynucleotide, ribozymes or antisense oligonucleotides, antibodies which specifically bind to a serine/threonine kinase polypeptide, or mimetics, activators, or inhibitors of a human serine/threonine kinase polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON's PHARMACEUTCAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

Human serine/threonine kinase can be regulated to treat cancer, diabetes, neurological disorders, cardiovascular disorders, musculo-skeletal disorders, inflammatory disorders, genitourological disorders, and respiratory disorders (e.g., asthma and COPD).

Cancer

Human serine/threonine kinase is highly expressed in the following cancer tissues: kidney tumor. Expression in the above-mentioned tissues and in particular the differential expression between diseased tissue and healthy tissue demonstrates that human serine/threonine kinase protein or mRNA can be used to diagnose cancer. In addition, the activity of human serine/threonine kinase can be modulated to treat cancer.

Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard canter therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Cancer disorders within the scope of the invention comprise any disease of an organ or tissue in mammals characterized by poorly controlled or uncontrolled multiplication of normal or abnormal cells in that tissue and its effect on the body as a whole. Cancer diseases within the scope of the invention comprise benign neoplasms, dysplasias, hyperplasias as well as neoplasms showing metastatic growth or any other transformations, e.g., leukoplalias, which often precede a breakout of cancer. Cells and tissues are cancerous when they grow more rapidly than normal cells, displacing or spreading into the surrounding healthy tissue or any other tissues of the body described as metastatic growth, assume abnormal shapes and sizes, show changes in their nucleocytoplasmatic ratio, nuclear polychromasia, and finally may cease.

Cancerous cells and tissues may affect the body as a whole when causing paraneoplastic syndromes or if cancer occurs within a vital organ or tissue, normal function will be impaired or halted, with possible fatal results. The ultimate involvement of a vital organ by cancer, either primary or metastatic, may lead to the death of the mammal affected. Cancer tends to spread, and the extent of its spread is usually related to an individual's chances of surviving the disease. Cancers are generally said to be in one of three stages of growth: early, or localized, when a tumor is still confined to the tissue of origin, or primary site; direct extension, where cancer cells from the tumour have invaded adjacent tissue or have spread only to regional lymph nodes; or metastasis, in which cancer cells have migrated to distant parts of the body from the primary site, via the blood or lymph systems, and have established secondary sites of infection. Cancer is said to be malignant because of its tendency to cause death if not treated.

Benign tumors usually do not cause death, although they may if they interfere with a normal body function by virtue of their location, size, or paraneoplastic side effects. Hence, benign tumors fall under the definition of cancer within the scope of the invention as well. In general, cancer cells divide at a higher rate than do normal cells, but the distinction between the growth of cancerous and normal tissues is not so much the rapidity of cell division in the former as it is the partial or complete loss of growth restraint in cancer cells and their failure to differentiate into a useful, limited tissue of the type that characterizes the functional equilibrium of growth of normal tissue.

Cancer tissues may express certain molecular receptors and probably are influenced by the host's susceptibility and immunity and it is known that-certain cancers of the breast and prostate, for example, are considered dependent on specific hormones for their existence. The term "cancer" under the scope of the invention is not limited to simple benign neoplasia but includes any other benign and malign neoplasia, such as 1) carcinoma, 2) sarcoma, 3) carcinosarcoma, 4) cancers of the blood-forming tissues, 5) tumors of nerve tissues including the brain, and 6) cancer of skin cells.

Carcinoma occurs in epithelial tissues, which cover the outer body (the skin) and line mucous membranes and the inner cavitary structures of organs e.g. such as the breast, lung, the respiratory and gastrointestinal tracts, the endocrine glands, and the genitourinary system. Ductal or glandular elements may persist in epithelial tumors, as in adenocarcinomas, e.g., thyroid adenocarcinoma, gastric adenocarcinoma, uterine adenocarcinoma. Cancers of the pavement-cell epithelium of the skin and of certain mucous membranes, such as cancers of the tongue, lip, larynx, urinary bladder, uterine cervix, or penis, may be termed epidermoid or squamous-cell carcinomas of the respective tissues and are within the scope of the definition of cancer as well.

Sarcomas develop in connective tissues, including fibrous tissues, adipose (fat) tissues, muscle, blood vessels, bone, and cartilage such as osteogenic sarcoma, liposarcoma, fibrosarcoma, and synovial sarcoma.

Carcinosarcoma is cancer that develops in both epithelial and connective tissue. Cancer disease within the scope of this definition may be primary or secondary, whereby primary indicates that the cancer originated in the tissue where it is found rather than was established as a secondary site through metastasis from another lesion. Cancers and tumor diseases within the scope of this definition may be benign or malign and may affect all anatomical structures of the body of a mammal. By example, to they comprise cancers and tumor diseases of I) the bone marrow and bone marrow derived cells (leukemias), II) the endocrine and exocrine glands, such as the thyroid, parathyroid, pituitary, adrenal glands, salivary glands, and pancreas III) the breast, such as benign or malignant tumors in the mammary glands of either a male or a female, the mammary ducts, adenocarcinoma, medullary carcinoma, comedocarcinoma, Paget's disease of the nipple, inflammatory carcinoma of the young woman, IV) the lung, V) the stomach, VI) the liver and spleen, VII) the small intestine, VIII) the colon, IX) the bone and its supportive and connective tissues such as malignant or benign bone tumour, such as malignant osteogenic sarcoma, benign osteoma, cartilage tumors, malignant chondrosarcoma or benign chondroma, bone marrow tumors such as malignant myeloma or benign eosinophilic granuloma, as well as metastatic tumors from bone tissues at other locations of the body; X) the mouth, throat, larynx, and the esophagus, XI) the urinary bladder and the internal and external organs and structures of the urogenital system of male and female such as the ovaries, uterus, cervix of the uterus, testes, and prostate gland, XII) the prostate, XIII) the pancreas, such as ductal carcinoma of the pancreas; XIV) the lymphatic tissue such as lymphomas and other tumors of lymphoid origin, XV) the skin, XVI) cancers and tumor diseases of all anatomical structures belonging to the respiratory systems including thoracal muscles and linings, XVI) primary or secondary cancer of the lymph nodes, XVIII) the tongue and of the bony structures of the hard palate or sinuses, XVIV) the mouth, cheeks, neck and salivary glands, XX) the blood vessels including the heart and their linings, XXI) the smooth or skeletal muscles and their ligaments and linings, XXII) the peripheral, the autonomous, the central nervous system including the cerebellum, and XXIII) the adipose tissue.

Protein phosphorylation is an essential component in intracellular signaling, with diverse and crucial functions including mediation of cell proliferation, survival, apoptosis, differentiation, migration and attachment. It is regulated by the balance between the opposing activities of protein kinases and protein phosphatases. Protein phosphorylation is mainly mediated by two types of protein kinases—protein tyrosine kinases and protein serine/threorine kinases. A number of protein tyrosine kinases are encoded by proto-oncogenes or viral oncogenes, and are thus strongly implicated in cancer. Protein serine/threonine kinases are known to play a role in intracellular signal transduction mediated by growth factors, cytokines, etc. inducing either cell proliferation, apoptosis or differentiation. Inhibitors of protein kinases are expected to provide efficacious therapeutic agents for the treatment of cancer.

Diabetes

Diabetes mellitus is a common metabolic disorder characterized by an abnormal elevation in blood glucose, alterations in lipids and abnormalities (complications) in the cardiovascular system, eye, kidney and nervous system. Diabetes is divided into two separate diseases: type 1 diabetes (juvenile onset), which results from a loss of cells which make and secrete insulin, and type 2 diabetes (adult onset), which is caused by a defect in insulin secretion and a defect in insulin action.

Type I diabetes is initiated by an autoimmune reaction that attacks the insulin secreting cells (beta cells) in the pancreatic islets. Agents that prevent this reaction from occurring or that stop the reaction before destruction of the beta cells has been accomplished are potential therapies for this disease. Other agents that induce beta cell proliferation and regeneration also are potential therapies.

Type II diabetes is the most common of the two diabetic conditions (6% of the population). The defect in insulin secretion is an important cause of the diabetic condition and results from an inability of the beta cell to properly detect and respond to rises in blood glucose levels with insulin release. Therapies that increase the response by the beta cell to glucose would offer an important new treatment for this disease.

The defect in insulin action in Type II diabetic subjects is another target for therapeutic intervention. Agents that increase the activity of the insulin receptor in muscle, liver, and fat will cause a decrease in blood glucose and a normalization of plasma lipids. The receptor activity can be increased by agents that directly stimulate the receptor or that increase the intracellular signals from the receptor. Other therapies can directly activate the cellular end process, i.e. glucose transport or various enzyme systems, to generate an insulin-like effect and therefore a produce beneficial outcome. Because overweight subjects have a greater susceptibility to Type II diabetes, any agent that reduces body weight is a possible therapy.

Both Type I and Type diabetes can be treated with agents that mimic insulin action or that treat diabetic complications by reducing blood glucose levels. Likewise, agents that reduces new blood vessel growth can be used to treat the eye complications that develop in both diseases.

Neurological Disorders

Human serine/threonine kinase is highly expressed in the following brain tissues: fetal brain, brain, Alzheimer brain, cerebellum, cerebellum (right), cerebellum (left), cerebral cortex, Alzheimer cerebral cortex, frontal lobe, Alzheimer brain frontal lobe, occipital lobe, parietal lobe, temporal lobe, precentral gyrus, tonsilla cerebelli, vermis cerebelli, pons, cerebral peduncles, corpus callosum, hippocampus, thalamus, spinal cord The expression in brain tissues and in particular the differential expression between diseased tissue and healthy tissue demonstrates that human serine/threonine kinase protein or mRNA can be used to diagnose nervous system diseases. In addition, the activity of human serine/threonine kinase can be modulated to treat nervous system diseases.

Central and peripheral nervous system disorders can be treated, such as primary and secondary disorders after brain injury, disorders of mood, anxiety disorders, disorders of thought and volition, disorders of sleep and wakefulness, diseases of the motor unit, such as neurogenic and myopathic disorders, neurodegenerative disorders such as Alzheimer's and Parkinson's disease, and processes of peripheral and chronic pain.

Pain that is associated with peripheral or central nervous system disorders also can be treated by regulating the activity of human serine/threonine kinase. Pain which can be treated includes that associated with central nervous system disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia Pain associated with cancer and cancer treatment also can be treated, as can headache pain (for example, migraine with aura, migraine without aura, and other migraine disorders), episodic and chronic tension-type headache, tension-type like headache, cluster headache, and chronic paroxysmal hemicrania.

Cardiovascular Disorders

Human serine/threonine kinase is highly expressed in the following cardiovascular related tissues: heart, pericardium, heart atrium (right), heart atrium (left), heart ventricle (left), interventricular septum. Expression in the above-mentioned tissues demonstrates that human serine/threonine kinase protein or mRNA can be used to diagnose cardiovascular diseases. In addition, the activity of human serine/threonine kinase can be modulated to treat cardiovascular diseases.

Heart failure is defined as a pathophysiological state in which an abnormality of cardiac function is responsible for the failure of the heart to pump blood at a rate commensurate with the requirement of the metabolizing tissue. It includes all forms of pumping failures such as high-output and low-output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included as well as the acute treatment of MI and the prevention of complications.

Ischemic diseases are conditions in which the coronary flow is restricted resulting in a perfusion which is inadequate to meet the myocardial requirement for oxygen. This group of diseases includes stable angina, unstable angina and asymptomatic ischemia.

Arrhythmias include all forms of atrial and ventricular tachyarrhythmias, atrial tachycardia, atrial flutter, atrial fibrillation, atrio-ventricular reentrant tachycardia, preexitation syndrome, ventricular tachycardia, ventricular flutter, ventricular fibrillation, as well as bradycardic forms of arrhythmias.

Hypertensive vascular diseases include primary as well as all kinds of secondary arterial hypertension, renal, endocrine, neurogenic, others. The genes may be used as drug targets for the treatment of hypertension as well as for the prevention of all complications arising from cardiovascular diseases.

Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon and venous disorders.

Atherosclerosis is a cardiovascular disease in which the vessel wall is remodeled, compromising the lumen of the vessel. The atherosclerotic remodeling process involves accumulation of cells, both smooth muscle cells and monocyte/macrophage inflammatory cells, in the intima of the vessel wall. These cells take up lipid, likely from the circulation, to form a mature atherosclerotic lesion. Although the formation of these lesions is a chronic process, occurring over decades of an adult human life, the majority of the morbidity associated with atherosclerosis occurs when a lesion ruptures, releasing thrombogenic debris that rapidly occludes the artery. When such an acute event occurs in the coronary artery, myocardial infarction can ensue, and in the worst case, can result in death.

The formation of the atherosclerotic lesion can be considered to occur in five overlapping stages such as migration, lipid accumulation, recruitment of inflammatory cells, proliferation of vascular smooth muscle cells, and extracellular matrix deposition. Each of these processes can be shown to occur in man and in animal models of atherosclerosis, but the relative contribution of each to the pathology and clinical significance of the lesion is unclear.

Thus, a need exists for therapeutic methods and agents to treat cardiovascular pathologies, such as atherosclerosis and other conditions related to coronary artery disease.

Cardiovascular diseases include but are not limited to disorders of the heart and the vascular system, such as congestive heart failure, myocardial infarction, ischemic diseases of the heart, all kinds of atrial and ventricular arrhythmias, hypertensive vascular diseases, peripheral vascular diseases, and atherosclerosis.

Levels of fats in the bloodstream that are too high or too low, especially cholesterol levels, can cause long-term problems. The risk to develop atherosclerosis and coronary artery or carotid artery disease (and thus the risk of having a heart attack or stroke) increases with the total cholesterol level increasing. Nevertheless, extremely low cholesterol levels may not be healthy. Examples of disorders of lipid metabolism are hyperlipidemia (abnormally high levels of fats (cholesterol, triglycerides, or both) in the blood, may be caused by family history of hyperlipidemia, obesity, a high-fat diet, lack of exercise, moderate to high alcohol consumption, cigarette smoking, poorly controlled diabetes, and an underactive thyroid gland), hereditary hyperlipidemias (type I hyperlipoproteinemia (familial hyperchylomicronemia), type II hyperlipoproteinemia (familial hypercholesterolemia), type III hyperlipoproteinemia, type IV hyperlipoproteinemia, or type V hyperlipoproteinemia), hypolipoproteinemia, lipidoses (caused by abnormalities in the enzymes that metabolize fats), Gaucher's disease, Niemann-Pick disease, Fabry's disease, Wolman's disease, cerebrotendinous xanthomatosis, sitosterolemia, Refsum's disease, or Tay-Sachs disease.

Kidney disorders may lead to hyper or hypotension. Examples for kidney problems possibly leading to hypertension are renal artery stenosis, pyelonephritis, glomerulonephritis, kidney tumors, polycistic kidney disease, injury to the kidney, or radiation therapy affecting the kidney. Excessive urination may lead to hypotension.

Musculo-skeletal Disorders

Human serine/threonine kinase is highly expressed in the following muscle/skeleton tissues: skeletal muscle. The expression in skeletal muscle demonstrates that human serine/threonine kinase protein or mRNA can be used to diagnose diseases of the musculo-skeletal system. In addition, the activity of human serine/threonine kinase can be modulated to treat those diseases.

Components of the musculoskeletal system are skeleton, muscles, tendons, ligaments, and other components of joints. Disorders of the musculoskeletal system often cause chronic pain and physical disability. These disorders include injuries, infections, inflammation, and other types of disorders. Examples of musculoskeletal disorders include osteoporosis, postmenopausal osteoporosis, senile osteoporosis, secondary osteoporosis, idiopathic juvenile osteoporosis, Paget's disease of the bone, osteochondromas (osteocartilaginous exostoses), tumors of the bone (benign chondromas, chondroblastomas, chondromyxoid fibromas, osteoid osteomas, giant cell tumors of the bone, multiple myeloma, osteosarcoma (osteogenic sarcoma), fibrosarcomas and malignant fibrous histiocytomas, chondrosarcomas, Ewing's tumor (Ewing's sarcoma), malignant lymphoma of bone (reticulum cell sarcoma, metastatic tumors of the bone), osteoarthritis, and gout and Pseudogout.

Disorders of the joints and connective tissue include rheumatoid arthritis, psoriatic arthritis, discoid lupus erythematosus, systemic lupus erythematosus, scleroderma (systemic sclerosis), Sjögren's syndrome, connective tissue disease, polymyositis and dermatomyositis, relapsing polychondritis, vasculitis, polyarteritis nodosa, polymyalgia rheumatica, temporal arteritis, Wegener's granulomatosis, Reiter's syndrome, Behçet's syndrome, ankylosing spondylitis, or Charcot's joints (neuropathic joint disease).

Bone and joint infections include osteomyelitis and infectious arthritis.

Disorders of the muscles, bursae, and tendons include spasmodic torticollis, fibromyalgia syndromes (myofascial pain syndromes, fibromyositis), bursitis, tendinitis and tenosynovitis.

Foot problems include, for example, ankle sprain, foot fractures, heel spurs, Sever's disease, posterior Achilles tendon bursitis, anterior Achilles tendon bursitis, posterior tibial neuralgia, pain in the ball of the foot (caused by damage to the nerves between the toes or to the joints between the toes and foot), onychomycosis, and nail discoloration.

Respiratory Disorders

Human serine/threonine kinase is highly expressed in the following tissues of the respiratory system: fetal lung fibroblast IMR-90 cells, lung, lung COPD. Expression in the above-mentioned tissues and in particular the differential expression between diseased tissue and healthy tissue demonstrates that human serine/threonine kinase protein or mRNA can be used to diagnose respiratory diseases. In addition, the activity of human serine/threonine kinase can be modulated to treat those diseases.

Asthma

Allergy is a complex process in which environmental antigens induce clinically adverse reactions. The inducing antigens, called allergens, typically elicit a specific IgE response and, although in most cases the allergens themselves have little or no intrinsic toxicity, they induce pathology when the IgE response in turn elicits an IgE-dependent or T cell-dependent hypersensitivity reaction. Hypersensitivity reactions can be local or systemic and typically occur within minutes of allergen exposure in individuals who have previously been sensitized to an allergen. The hypersensitivity reaction of allergy develops when the allergen is recognized by IgE antibodies bound to specific receptors on the surface of effector cells, such as mast cells, basophils, or eosinophils, which causes the activation of the effector cells and the release of mediators that produce the acute signs and symptoms of the reactions. Allergic diseases include asthma, allergic rhinitis (hay fever), atopic dermatitis, and anaphylaxis.

Asthma is thought to arise as a result of interactions between multiple genetic and environmental factors and is characterized by three major features: 1) intermittent and reversible airway obstruction caused by bronchoconstriction, increased mucus production, and thickening of the walls of the airways that leads to a narrowing of the airways, 2) airway hyperresponsiveness caused by a decreased control of airway caliber, and 3) airway inflammation. Certain cells are critical to the inflammatory reaction of asthma and they include T cells and antigen presenting cells, B cells that produce IgE, and mast cells, basophils, eosinophils, and other cells that bind IgE. These effector cells accumulate at the site of allergic reaction in the airways and release toxic products that contribute to the acute pathology and eventually to the tissue destruction related to the disorder. Other resident cells, such as smooth muscle cells, lung epithelial cells, mucus-producing cells, and nerve cells may also be abnormal in individuals with asthma and may contribute to the pathology. While the airway obstruction of asthma, presenting clinically as an intermittent wheeze and shortness of breath, is generally the most pressing symptom of the disease requiring immediate treatment, the inflammation and tissue destruction associated with the disease can lead to irreversible changes that eventually make asthma a chronic disabling disorder requiring long-term management.

Despite recent important advances in our understanding of the pathophysiology of asthma, the disease appears to be increasing in prevalence and severity (Gergen and Weiss, Am. Rev. Respir. Dis. 146, 823–24, 1992). It is estimated that 30–40% of the population suffer with atopic allergy, and 15% of children and 5% of adults in the population suffer from asthma (Gergen and Weiss, 1992). Thus, an enormous burden is placed on our health care resources. However, both diagnosis and treatment of asthma are difficult. The severity of lung tissue inflammation is not easy to measure and the symptoms of the disease are often indistinguishable from those of respiratory infections, chronic respiratory inflammatory disorders, allergic rhinitis, or other respiratory disorders. Often, the inciting allergen cannot be determined, making removal of the causative environmental agent difficult. Current pharmacological treatments suffer their own set of disadvantages. Commonly used therapeutic agents, such as beta agonists, can act as symptom relievers to transiently improve pulmonary function, but do not affect the underlying inflammation. Agents that can reduce the underlying inflammation, such as anti-inflammatory steroids, can have major drawbacks that range from immunosuppression to bone loss (Goodman and Gilman's THE PHRAMACOLOGIC BASIS OF THERAPEUTICS, Seventh Edition, MacMillan Publishing Company, NY, USA, 1985). In addition, many of the present therapies, such as inhaled corticosteroids, are short-lasting, inconvenient to use, and must be used often on a regular basis, in some cases for life; making failure of patients to comply with the treatment a major problem and thereby reducing their effectiveness as a treatment.

Because of the problems associated with conventional therapies, alternative treatment strategies have been evaluated. Glycophorin A (Chu and Sharom, Cell. Immunol. 145, 223–39, 1992), cyclosporin (Alexander et al., Lancet 33P, 324–28, 1992), and a nonapeptide fragment of IL-2 (Zav'yalov et al., Immunol. Lett. 31, 285–88, 1992) all inhibit interleukin-2 dependent T lymphocyte proliferation; however, they are known to have many other effects. For example, cyclosporin is used as a immuno-suppressant after organ transplantation. While these agents may represent alternatives to steroids in the treatment of asthmatics, they inhibit interleukin-2 dependent T lymphocyte proliferation and potentially critical immune functions associated with homeostasis. Other treatments that block the release or activity of mediators of bronchochonstriction, such as cromones or anti-leukotrienes, have recently been introduced for the treatment of mild asthma, but they are expensive and not effective in all patients and it is unclear whether they have any effect on the chronic changes associated with asthmatic inflammation. What is needed in the art is the identification of a treatment that can act in pathways critical to the development of asthma_that both blocks the episodic attacks of the disorder and preferentially dampens the hyperactive allergic immune response without immunocompromising the patient.

COPD

Chronic obstructive pulmonary (or airways) disease (COPD) is a condition defined physiologically as airflow obstruction that generally results from a mixture of emphysema and peripheral airway obstruction due to chronic bronchitis (Senior & Shapiro, Pulmonary Diseases and Disorders, 3d ed., New York, McGraw-Hill, 1998, pp. 659–681, 1998; Barnes, Chest 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

Protein Kinases. Protein kinases are signal transducing enzymes that phosphorylate proteins, including other kinases, and, along with protein phosphatases, regulate the level and extent of protein phosphorylation and activation. Intracellular signalling pathways have important roles in inflammatory processes. These pathways may be activated by cytokines, oxidant stress and other inflammatory mediators (reviewed in Kyraikis and Avruch, 1996 and 2001). For example, the pro-inflammatory cytokines, tumor necrosis factor α (TNFα) and interleukin-1 activate the protein ser/thr kinases c-Jun-NH2-terminal kinase (JNK) and p38 mitogen-activated protein (MAP) kinase, leading to activation of AP-1 and IKB kinase (IKK), which, in turn, leads to activation of the transcription factor NFKB. Activation of NFKB is required for the transcription of several pro-inflammatory molecules, including interleukin-8 and ICAM-1. Enzymes of the MAP kinase class may also act to increase cytokine production by stabilization of mRNA (Winzen et al., 1999).

Inhibition of specific protein kinases has been shown to elicit anti-inflammatory effects. For example, the accumulation of polymorphonuclear leukocytes in murine lung following intratracheal administration of bacterial lipopolysaccharide can be blocked by inhibition of p38 MAP kinase (Nick, et al. 2000). As a further example, aerosol delivery to rat lungs of antisense oligodeoxynucleotides to syk kinase mRNA, suppressed nitric oxide and TNFα production from alveolar macrophages stimulated with IgG-anti-IgG complexes (Stenton et al. 2000). Protein kinase subtypes are therefore attractive therapeutic targets for the attenuation of the inflammatory response in COPD. See Kyriakis, J. M. and Avruch J. Sounding the alarm: protein kinase cascades activated by stress and inflammation. J Biol Chem 1996, 271:24313–6; Kyriakis, J. M. and Avruch, J. Mammalian mitogen-activated protein kinase signal transduction pathways activated by stress and inflammation. J. Physiol. Rev. 2001, 81:807–69; Winzen, R, Kracht, M., Ritter, B., Wilhelm, A., Chen C. A., Shyu, A., Müller, M., Gaestel, M., Resch, K., and Holtmann, H. The p38 MAP kinase pathway signals for cytokine-induced mRNA stabilization via MAP kinase-activated protein kinase 2 and an AU-rich region-targeted mechanism. EMBO J 1999, 18: 4969–4980; Nick, J. A., Young, S. Y, Brown, K. K., Avdi, N. J., Arndt, P. G., Suratt, B. T., Janes, M. S., Henson, P. M., Worthen, G. S. Role of p38 mitogen-activated protein kinase in a murine model of pulmonary inflammation. J Immunol. 2000, 164:2151–9; and Stenton, G. R., Kim, M. K., Nohara, O., Chen, C. F., Hirji, N., Wills, F. L., Gilchrist, M., Hwang, P. H., Park, J. G., Finlay, W., Jones, R. L., Befus, A. D., Schreiber, A. D. Aerosolized Syk antisense suppresses Syk expression, mediator release from macrophages, and pulmonary inflammation. J Immunol 2000, 164:3790–7.

Inflammatory Disorders

Human serine/threonine kinase is highly expressed in the following tissues of the immune system and tissues responsive to components of the immune system as well as in the following tissues responsive to mediators of inflammation: lung COPD. Expression in the above-mentioned tissues and in particular the differential expression between diseased tissue and healthy tissue demonstrates that human serine/threonine kinase protein or mRNA can be used to diagnose inflammatory diseases. In addition, the activity of human serine/threonine kinase can be modulated to treat inflammatory diseases.

Inflammatory diseases include diseases triggered by cellular or non-cellular mediators of the immune system or tissues causing the inflammation of body tissues and subsequently producing an acute or chronic inflammatory condition. Examples of such inflammatory diseases are hypersensitivity reactions of type I–IV, e.g. hypersensitivity diseases of the lung including asthma, atopic diseases, allergic rhinitis or conjunctivitis, angioedema of the lids, hereditary angioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, glomerulonephritis, acute or chronic host versus graft reactions.

Genitourinary Disorders

Human serine/threonine kinase is highly expressed in the following urological tissues: fetal kidney, kidney, kidney tumor. Expression in the above-mentioned tissues and in particular the differential expression between diseased tissue and healthy tissue demonstrates that human serine/threonine kinase protein or mRNA can be used to diagnose urological disorders. In addition, the activity of human serine/threonine kinase can be modulated to treat genitourological disorders.

Genitourological disorders comprise benign and malign disorders of the organs constituting the genitourological system of female and male, renal diseases such as acute or chronic renal failure, immunologically mediated renal diseases such as renal transplant rejection, lupus nephritis, immune complex renal diseases, glomerulopathies, nephritis, toxic nephropathy, obstructive uropathies such as benign prostatic hyperplasia (BPH), neurogenic bladder syndrome, urinary incontinence such as urge-, stress-, or overflow incontinence, pelvic pain, and erectile dysfunction.

Benign Prostatic Hyperplasia. Benign prostatic hyperplasia (BPH) is the benign nodular hyperplasia of the periurethral prostate gland commonly seen in men over the age of 50. The overgrowth occurs in the central area of the prostate called the transition zone, which wraps around the urethra BPH causes variable degrees of bladder outlet obstruction, resulting in progressive lower urinary tract syndromes (LUTS) characterized by urinary frequency, urgency, and nocturia due to incomplete emptying and rapid refilling of the bladder. The actual cause of BPH is unknown but may involve age-related alterations in balance of steroidal sex hormones.

Selective $\alpha 1$-adrenoceptor antagonists, such as prazosin, indoramin, and tamsulosin, are used as an adjunct in the symptomatic treatment of urinary obstruction caused by BPH, although they do not affect on the underlying cause of BPH. In BPH, increased sympathetic tone exacerbates the degree of obstruction of the urethra through contraction of prostatic and urethral smooth muscle. These compounds inhibit sympathetic activity, thereby relaxing the smooth muscle of the urinary tract. Uroselective $\alpha 1$-antagonists and $\alpha 1$-antagonists with high tissue selectivity for lower urinary tract smooth muscle that do not provoke hypotensive side-effects should be developed for the treatment.

Drugs blocking dihydrotestosterone have been used to reduce the size of the prostate. $5\alpha$-reductase inhibitors such as finasteride are prescribed for BPH. These agents selectively inhibit $5\alpha$-reductase which mediates conversion of testosterone to dihydrotestosterone, thereby reducing plasma dihydrotestosterone levels and, thus, prostate growth. The $5\alpha$-reductase inhibitors do not bind to androgen receptors and do not affect testosterone levels, nor do they possess feminizing side-effects.

Androgen receptor antagonists are used for the treatment of prostatic hyperplasia due to excessive action or production of testosterone. Various antiandrogens are under investigation for BPH including chlormadione derivatives with no estrogenic activity, orally-active aromatase inhibitors, and luteinizing hormone-releasing hormone (LHRH) analogues.

Urinary Incontinence. Urinary incontinence (UI) is the involuntary loss of urine. Urge urinary incontinence (UUI) is one of the most common types of UI together with stress urinary incontinence (SUI), which is usually caused by a defect in the urethral closure mechanism. UUI is often associated with neurological disorders or diseases causing neuronal damage, such as dementia, Parkinson's disease, multiple sclerosis, stroke, and diabetes, although it also occurs in individuals with no such disorders. One of the usual causes of UUI is overactive bladder (OAB), which is a medical condition referring to the symptoms of frequency and urgency derived from abnormal contractions and instability of the detrusor muscle.

There are several medications for urinary incontinence on the market today, mainly to help treating UUI. Therapy for OAB is focused on drugs that affect peripheral neural control mechanisms or those that act directly on bladder detrusor smooth muscle contraction, with a major emphasis on development of anticholinergic agents. These agents can inhibit the parasympathetic nerves, which control bladder voiding, or can exert a direct spasmolytic effect on the detrusor muscle of the bladder. This results in a decrease in intravesicular pressure, an increase in capacity, and a reduction in the frequency of bladder contraction. Orally active anticholinergic drugs, such as propantheline (ProBanthine), tolterodine tartrate (Detrol), and oxybutynin (Ditropan), are the most commonly prescribed drugs. However, their most serious drawbacks are unacceptable side effects, such as dry mouth, abnormal visions, constipation, and central nervous system disturbances. These side effects lead to poor compliance. Dry mouth symptoms alone are responsible for a 70% non-compliance rate with oxybutynin. The inadequacies of present therapies highlight the need for novel, efficacious, safe, orally available drugs that have fewer side effects.

Serine/Threonine Kinases and Treatment of Urological Disorders

Serine/Threonine kinases, such as protein kinase C (PKC) and myosin light-chain kinase (MLCK) are known to play physiological roles in urination through controlling the contraction of bladder smooth muscles.

PKC is a serine/threonine kinase, which consists of at least 10 isoforms. The isoforms have distinct features in structure, substrate requirement, expression profiles, and intracellular localization. Five PKC isoforms ($\beta1$, $\beta2$, $\delta$, $\epsilon$, and $\zeta$) are expressed in rat dorsal root ganglion (DRG). When cultured DRG neurons were stimulated by Bradykinin (BK), only PKC$\epsilon$ specifically translocates to the plasma membranes, indicating a physiological importance of PKC$\epsilon$ in neuronal response in rat DRG. Cesare, et al., *Neuron* 23, 617–24, 1999. PKC$\epsilon$ is abundantly expressed in the central and peripheral nerve systems. It is activated by diacylglycerol or TPA in an independent manner of $Ca^{2+}$, which is different from classical PKCs. Nishizuka, *Science* 258, 607–14, 1992; Way et al., *Trends in Pharm. Sci.* 21, 181–87, 2000.

Recent studies showed that BK-evoked thermal hypersensitivity was attenuated in vanilloid receptor 1 (VR1) knockout mice. Julius et al., *Nature* 413, 203–10, 2001. Furthermore, BK markedly enhanced proton- and capsaicin-evoked membrane potentials in VR1/B2-transfected cells. These results imply that BK is involved in overactive bladder and urinary incontinence through the VR1-mediated sensory nerve potentiation, because VR1 plays a key role in the sensory C-fiber afferent nerves. Desensitization by VR1 agonists such as capsaicin and resiniferatoxin is currently being evaluated in clinical study for the treatment of urinary incontinence. Chuang et al., *Nature* 411, 957–62, 2001.

Thus, it appears that activation of PKC-epsilon plays a pivotal role in the BK-evoked VR1-mediated sensitization of sensory nerves in hyperactive bladder. Therefore, PKC$\epsilon$ inhibitors may have therapeutic potential for the treatment of overactive bladder and urinary incontinence.

Bladder filling and emptying is well-balanced coordinated control of contraction and relaxation of the bladder body, the bladder base and urethra. Contraction of smooth muscle is produced by the sliding of actin filaments against myosin filaments. The head regions of myosin molecules attach to adjacent actin filaments in an ATP-dependent manner. One of the two light chains on the head regions of the myosin-II molecule is phosphorylated during muscle contraction. When this light chain is phosphorylated, the myosin head interacts with an actin filament and causes contraction, whereas the myosin head dissociates from actin when the light chain is dephosphorylated. The phosphorylation is catalyzed by MLCK, which requires the binding of a $Ca^{2+}$/calmodulin complex for activation. Therefore, the contractile state of bladder smooth muscle is mediated by $Ca^{2+}$-regulated phosphorylation of myosin light chains in the assembly units.

A high degree of insertion of 7-amino acids near the ATP-binding region and LC20 phosphorylation in myosin from the bladder body samples was demonstrated, although non-inserted myosin and the low level of myosin light chain phosphorylation was observed in the urethra. Prior studies have shown that the inserted myosin has a two-fold higher actin-activated ATPase activity compared to the insert-less isoform. The tight contraction of bladder dome may help to facilitate rapid force development and emptying, while loose contraction may contribute to slowly or non-cycling myosin cross bridges and the maintenance of a tonic or contracted state during bladder filling. Hypolite et al., *Scand. J. Urol. Nephrol.* (*Suppl.* 201), 46–50, 1999.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a human serine/threonine kinase polypeptide binding molecule) can be used in an animal model to determine the efficacy, toxicity, or side effects of treatment with such an agent. Alternatively, an agent identified as described herein can bemused in an animal model to determine the mechanism of action of such an agent. Furthermore, this invention pertains to uses of novel agents identified by the above-described screening assays for treatments as described herein.

A reagent which affects serine/threonine kinase activity can be administered to a human cell, either in vitro or in vivo, to reduce serine/threonine kinase activity. The reagent preferably binds to an expression product of a human serine/threonine kinase gene. If the expression product is a protein, the reagent is preferably an antibody. For treatment of human cells ex vivo, an antibody can be added to a preparation of stem cells that have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient that increases or decreases enzymatic activity relative to the enzymatic activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of a human serine/threonine kinase gene or the activity of a serine/threonine kinase polypeptide by at least about 10, preferably about 50, more preferably about 75, 90, or 100% relative to the absence of the reagent. The effectiveness of the mechanism chosen to decrease the level of expression of a human serine/threonine kinase gene or the activity of a human serine/threonine kinase polypeptide can be assessed using methods well known in the art, such as hybridization of nucleotide probes to serine/threonine kinase-specific mRNA, quantitative RT-PCR, immunologic detection of a human serine/threonine kinase polypeptide, or measurement of enzymatic activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human serine/threonine kinase also can be used in diagnostic assays for detecting diseases and abnormalities or susceptibility to diseases and abnormalities related to the presence of mutations in the nucleic acid sequences that encode the enzyme. For example, differences can be determined between the cDNA or genomic sequence encoding serine/threonine kinase in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be 5 revealed by nuclease protection assays, such as RNase and S 1 protection or the chemical cleavage method (e.g., Cotton et al., *Proc. Natl. Acad Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of serine/threonine kinase also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Detection of Serine/Threonine Kinase Activity

For high level expression of a FLAG-tagged serine/threonine kinase polypeptide, COS-1 cells are transfected with the expression vector pC-serine/threonine kinase polypeptide (expressing the DNA-sequence of ID NO: 1) using the calcium phosphate method. After 5 h, the cells are infected with recombinant vaccinia virus vTF7-3 (10 plaque-forming units/cell). The cells are harvested 20 h after infection and lysed in 50 mM Tris, pH 7,5, 5 mM MgCl$_2$, 0,1% Nonidet P-40, 0,5 mM dithiothreitol, 1 mM phenylmethylsulfonyl fluoride, 10 μg/ml aprotinin. Serine/threonine kinase polypeptide is immunoprecipitated from the lysate using anti-FLAG antibodies. In vitro kinase assay and phosphoamino acid analysis are performed in a volume of 40 μl with immunoprecipitated FLAG serine/threonine kinase polypeptide in 50 mM Tris-HCl, pH 8.0, 50 mM NaCl, 5 mM MgCl$_2$, 1 mM dithiothreitol. The reaction is started by the addition of 4 μl of 1 mM ATP supplemented with 5 μCi of ($-^{32}$P)ATP and incubated for 30 min at 37° C. Afterward, the samples are subjected to SDS-PAGE and phosphorylated proteins are detected by autoradiography. Histone type III-S, casein, bovine serum albumin, or myelin basic proteins are used as substrates. It is shown that the polypeptide with the amino acid sequence of SEQ ID NO: 2 has serine/threonine kinase activity.

EXAMPLE 2

Expression of Recombinant Human Serine/Threonine Kinase

The *Pichia pastoris* expression vector pPICZB Invitrogen, San Diego, Calif.) is used to produce large quantities of recombinant human serine/threonine kinase polypeptides in yeast. The serine/threonine kinase-encoding DNA sequence is derived from SEQ ID NO: 1. Before insertion into vector pPICZB, the DNA sequence is modified by well known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris,* driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni—NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human serine/threonine kinase polypeptide is obtained.

EXAMPLE 3

Identification of Test Compounds that Bind to Serine/Threonine Kinase Polypeptides Purified serine/threonine kinase polypeptides comprising a glutathione-S-transferase protein and absorbed onto glutathione-derivatized wells of 96-well microtiter plates are contacted with test compounds from a small molecule library at pH 7.0 in a physiological buffer solution. Human serine/threonine kinase polypeptides comprise the amino acid sequence shown in SEQ ID NO: 2. The test compounds comprise a fluorescent tag. The samples are incubated for 5 minutes to one hour. Control samples are incubated in the absence of a test compound.

The buffer solution containing the test compounds is washed from the wells. Binding of a test compound to a human serine/threonine kinase polypeptide is detected by fluorescence measurements of the contents of the wells. A test compound that increases the fluorescence in a well by at least 15% relative to fluorescence of a well in which a test compound is not incubated is identified as a compound which binds to a human serine/threonine kinase polypeptide.

EXAMPLE 4

Identification of a Test Compound Which Decreases Serine/Threonine Kinase Gene Expression A test compound is administered to a culture of human cells transfected with a serine/threonine kinase expression construct and incubated at 37° C. for 10 to 45 minutes. A culture of the same type of cells that have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 µg total RNA and hybridized with a $^{32}$P-labeled serine/threonine kinase-specific probe at 65° C. in Express-hyb (CLONTECH). The probe comprises at least 11 contiguous nucleotides selected from the complement of SEQ ID NO: 1. A test compound that decreases the serine/threonine kinase-specific signal-relative to the signal obtained in the absence of the test compound is identified as an inhibitor of serine/threonine kinase gene expression.

EXAMPLE 5

Identification of a Test Compound Which Decreases Serine/Threonine Kinase Activity A test compound is administered to a culture of human cells transfected with a serine/threonine kinase expression construct and incubated at 37° C. for 10 to 45 minutes. A culture of the same type of cells that have not been transfected is incubated for the same time without the test compound to provide a negative control.

Kinase activity may be measured by phosphorylation of a protein substrate such as myelin basic protein using gamma-labeled $^{32}$P-ATP and quantitation of the incorporated radioactivity using a gamma radioisotope counter. Human serine/threonine kinase is incubated with the protein substrate, $^{32}$P-ATP, and a kinase buffer. The $^{32}$P incorporated into the substrate is then separated from free $^{32}$P-ATP by electrophoresis and the incorporated $^{32}$P is counted. A determination of the specific amino acid residues phosphorylated is made by phosphoamino acid analysis of the hydrolyzed protein as described by Boyle et al., *Meth. Enzymol* 20, 110–148, 1991. A test compound which decreases the enzymatic activity of the kinase relative to the enzymatic activity in the absence of the test compound is identified as an inhibitor of kinase activity.

EXAMPLE 6

Tissue-specific Expression of Serine/Threonine Kinase

The qualitative expression pattern of serine/threonine kinase in various tissues is determined by Reverse Transcription-Polymerase Chain Reaction (RT-PCR).

Quantitative Expression Profiling

To demonstrate that serine/threonine kinase is involved in cancer, expression is determined in the following tissues: adrenal gland, bone marrow, brain, cerebellum, colon, fetal brain, fetal liver, heart, kidney, liver, lung, mammary gland, pancreas, placenta, prostate, salivary gland, skeletal muscle, small intestine, spinal cord, spleen, stomach, testis, thymus, thyroid, trachea, uterus, and peripheral blood lymphocytes. Expression in the following cancer cell lines also is determined: DU-145 (prostate), NCI-H125 (lung), HT-29 (colon), COLO-205 (colon), A-549 (lung), NCI-H460 (lung), HT-116 (colon), DLD-1 (colon), MDA-MD-231 (breast), LS174T (colon), ZF-75 (breast), MDA-MN435 (breast), HT-1080, MCF-7 (breast), and U87. Matched pairs of malignant and normal tissue from the same patient also are tested.

To demonstrate that serine/threonine kinase is involved in the disease process of diabetes, the following whole body panel is screened to show predominant or relatively high expression: subcutaneous and mesenteric adipose tissue, adrenal gland, bone marrow, brain, colon, fetal brain, heart, hypothalamus, kidney, liver, lung, mammary gland, pancreas, placenta, prostate, salivary gland, skeletal muscle, small intestine, spleen, stomach, testis, thymus, thyroid, trachea, and uterus. Human islet cells and an islet cell library also are tested. As a final step, the expression of serine/threonine kinase in cells derived from normal individuals with the expression of cells derived from diabetic individuals is compared.

To demonstrate that serine/threonine kinase is involved in peripheral or central nervous system disorders, the following tissues are screened: fetal and adult brain, muscle, heart, lung, kidney, liver, thymus, testis, colon, placenta, trachea, pancreas, kidney, gastric mucosa, colon, liver, cerebellum, skin, cortex (Alzheimer's and normal), hypothalamus, cortex, amygdala, cerebellum, hippocampus, choroid, plexus, thalamus, and spinal cord.

To demonstrate that serine/threonine kinase is involved in the disease process of COPD, the initial expression panel consists of RNA samples from respiratory tissues and inflammatory cells relevant to COPD: lung (adult and fetal), trachea, freshly isolated alveolar type II cells, cultured human bronchial epithelial cells, cultured small airway epithelial cells, cultured bronchial sooth muscle cells, cultured H441 cells (Clara-like), freshly isolated neutrophils and monocytes, and cultured monocytes (macrophage-like). Body map profiling also is carried out, using total RNA panels purchased from Clontech. The tissues are adrenal gland, bone marrow, brain, colon, heart, kidney, liver, lung, mammary gland, pancreas, prostate, salivary gland, skeletal muscle, small intestine, spleen, stomach, testis, thymus, trachea, thyroid, and uterus.

Quantitative expression profiling is performed by the form of quantitative PCR analysis called "kinetic analysis" firstly described in Higuchi et al., *BioTechnology* 10, 413–17, 1992, and Higuchi et al., *BioTechnology* 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'-3' endonuclease activity of Taq DNA polymerase and a fluorescent dye released in the medium (Holland et al., *Proc. Natl. Acad Sci. USA.* 88, 7276–80, 1991). Because the fluorescence emission will increase in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used. All "real time PCR" measurements of fluorescence are made in the ABI Prism 7700.

RNA extraction and cDNA preparation. Total RNA from the tissues listed above are used for expression quantification. RNAs labeled "from autopsy" were extracted from autoptic tissues with the TRIzol reagent (Life Technologies, MD) according to the manufacturer's protocol.

Fifty µg of each RNA were treated with DNase I for 1 hour at 37° C. in the following reaction mix: 0.2 U/µl RNase-free DNase I (Roche Diagnostics, Germany); 0.4 U/µl RNase inhibitor (PE Applied Biosystems, CA); 10 mM Tris-HCl pH 7.9; 10 mM $MgCl_2$; 50 mM NaCl; and 1 mM DTT.

After incubation, RNA is extracted once with 1 volume of phenol:chloroform:isoamyl alcohol (24:24:1) and once with chloroform, and precipitated with 1/10 volume of 3 M sodium acetate, pH 5.2, and 2 volumes of ethanol.

50 µg of each RNA from the autoptic tissues are DNase treated with the DNA-free kit purchased from Ambion (Ambion, Tex.). After resuspension and spectrophotometric quantification, each sample is reverse transcribed with the TaqMan Reverse Transcription Reagents (PE Applied Biosystems, CA) according to the manufacturer's protocol. The final concentration of RNA in the reaction mix is 200 ng/µL. Reverse transcription is carried out with 2.5 µM of random hexamer primers.

TaqMan quantitative analysis. Specific primers and probe are designed according to the recommendations of PE Applied Biosystems; the probe can be labeled at the 5' end FAM (6-carboxy-fluorescein) and at the 3' end with TAMRA (6-carboxy-tetramethyl-rhodamine). Quantification experiments are performed on 10 ng of reverse transcribed RNA from each sample. Each determination is done in triplicate.

Total cDNA content is normalized with the simultaneous quantification (multiplex PCR) of the 18S ribosomal RNA using the Pre-Developed TaqMan Assay Reagents (PDAR) Control Kit (PE Applied Biosystems, CA).

The assay reaction mix is as follows: 1× final TaqMan Universal PCR Master Mix (from 2× stock) (PE Applied Biosystems, CA); 1× PDAR control—18S RNA (from 20× stock); 300 nM forward primer; 900 nM reverse primer; 200 nM probe; 10 ng cDNA; and water to 25 µl.

Each of the following steps are carried out once: pre PCR, 2 minutes at 50° C., and 10 minutes at 95° C. The following steps are carried out 40 times: denaturation, 15 seconds at 95° C., annealing/extension, 1 minute at 60° C.

The experiment is performed on an ABI Prism 7700 Sequence Detector (PE Applied Biosystems, CA). At the end of the run, fluorescence data acquired during PCR are processed as described in the ABI Prism 7700 user's manual in order to achieve better background subtraction as well as signal linearity with the starting target quantity.

EXAMPLE 7

Proliferation Inhibition Assay: Antisense Oligonucleotides Suppress the Growth of Cancer Cell Lines The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5% $CO_2$ atmosphere.

Phosphorothioate oligoribonucleotides are synthesized on an Applied Biosystems Model 380B DNA synthesizer using phosphoroamidite chemistry. A sequence of 24 bases complementary to the nucleotides at position 1 to 24 of SEQ ID NO: 1 is used as the test oligonucleotide. As a control, another (random) sequence is used: 5'-TCA ACT GAC TAG ATG TAC ATG GAC-3' (SEQ ID NO: 20). Following assembly and deprotection, oligonucleotides are ethanol-precipitated twice, dried, and suspended in phosphate buffered saline at the desired concentration. Purity of the oligonucleotides is tested by capillary gel electrophoresis and ion exchange HPLC. The purified oligonucleotides are added to the culture medium at a concentration of 10 µM once per day for seven days.

The addition of the test oligonucleotide for seven days results in significantly reduced expression of human serine/threonine kinase as determined by Western blotting. This effect is not observed with the control oligonucleotide. After 3 to 7 days, the number of cells in the cultures is counted using an automatic cell counter. The number of cells in cultures treated with the test oligonucleotide (expressed as 100%) is compared with the number of cells in cultures treated with the control oligonucleotide. The number of cells in cultures treated with the test oligonucleotide is not more than 30% of control, indicating that the inhibition of human serine/threonine kinase has an anti-proliferative effect on cancer cells.

EXAMPLE 8

In Vivo Testing of Compounds/Target Validation for Cancer Treatment

Acute Mechanistic Assays

Reduction in Mitogenic Plasma Hormone Levels

This non-tumor assay measures the ability of a compound to reduce either the endogenous level of a circulating hormone or the level of hormone produced in response to a biologic stimulus. Rodents are administered test compound (p.o., i.p., i.v., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pre-treatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value≦0.05 compared to the vehicle control group.

Hollow Fiber Mechanism of Action Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman) or a specific biochemical activity (i.e., cAMP levels. Results are analyzed by Student's t-test or Rank Sum test after the variance between groups is compared by an F-test, with significance at $p \leq 0.05$ as compared to the vehicle control group.

Subacute Functional in Vivo Assays

Reduction in Mass of Hormone Dependent Tissues

This is another non-tumor assay that measures the ability of a compound to reduce the mass of a hormone dependent tissue (i.e., seminal vesicles in males and uteri in females). Rodents are -administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects are compared to a vehicle-treated control group. An F-test is preformed to determine if the variance is equal or unequal followed by a Student's t-test. Significance is p value $\leq 0.05$ compared to the vehicle control group.

Hollow Fiber Proliferation Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at $p \leq 0.05$ as compared to the vehicle control group.

Anti-angiogenesis Models

Corneal Angiogenesis

Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank Sum test. Image analysis data is evaluated by measuring the area of neovascularization (in pixels) and group averages are compared by Student's t-test (2 tail). Significance is $p \leq 0.05$ as compared to the growth factor or cells only group.

Matrigel Angiogenesis

Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at $p \leq 0.05$ as compared to the vehicle control group.

Primary Antitumor Efficacy

Early Therapy Models

Subcutaneous Tumor

Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Anti-tumor efficacy may be initially determined by comparing the size of treated (T) and control (C) tumors on a given day by a Student's t-test, after the variance between groups is compared by an F-test, with significance determined at $p \leq 0.05$. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is $p \leq 0.05$.

Intraperitoneal Intracranial Tumor Models

Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is $p \leq 0.05$ by a log-rank test compared to the control group in the experiment.

Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group.

Orthotopic Disease Models

Mammary Fat Pad Assay

Tumor cells or fragments, of mammary adenocarcinoma origin, are implanted directly into a surgically exposed and reflected mammary fat pad in rodents. The fat pad is placed back in its original position and the surgical site is closed.

Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at $p \leq 0.05$ compared to the control group in the experiment.

Intraprostatic Assay

Tumor cells or fragments, of prostatic adenocarcinoma origin, are implanted directly into a surgically exposed dorsal lobe of the prostate in rodents. The prostate is externalized through an abdominal incision so, that the tumor can be implanted specifically in the dorsal lobe while verifying that the implant does not enter the seminal vesicles. The successfully inoculated prostate is replaced in the abdomen and the incisions through the abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at $p \leq 0.05$ compared to the control group in the experiment.

Intrabronchial Assay

Tumor cells of pulmonary origin may be implanted intrabronchially by making an incision through the skin and exposing the trachea The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at $p \leq 0.05$ compared to the control group in the experiment.

Intracecal Assay

Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at $p \leq 0.05$ compared to the control group in the experiment.

Secondary (Metastatic) Antitumor Efficacy

Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance determined at $p \leq 0.05$ compared to the control group in the experiment for both of these endpoints.

Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance at $p \leq 0.05$ compared to the vehicle control group in the experiment for both endpoints.

EXAMPLE 9

Diabetes: In Vivo Testing of Compounds/Target Validation

Glucose Production

Over-production of glucose by the liver, due to an enhanced rate of gluconeogenesis, is the major cause of fasting hyperglycemia in diabetes. Overnight fasted normal rats or mice have elevated rates of gluconeogenesis as do streptozotocin-induced diabetic rats or mice fed ad libitum. Rats are made diabetic with a single intravenous injection of 40 mg/kg of streptozotocin while C57BL/KsJ mice are given 40–60 mg/kg i.p. for 5 consecutive days. Blood glucose is measured from tail-tip blood and then compounds are administered via different routes (p.o., i.p., i.v., s.c.). Blood is collected at various times thereafter and glucose measured. Alternatively, compounds are administered for several days, then the animals are fasted overnight, blood is collected and plasma glucose measured. Compounds that inhibit glucose production will decrease plasma glucose levels compared to the vehicle-treated control group.

Insulin Sensitivity

Both ob/ob and db/db mice as well as diabetic Zucker rats are hyperglycemic, hyperinsulinemic and insulin resistant. The animals are pre-bled, their glucose levels measured, and then they are grouped so that the mean glucose level is the same for each group. Compounds are administered daily either q.d. or b.i.d. by different routes (p.o., i.p., s.c.) for 7–28 days. Blood is collected at various times and plasma glucose and insulin levels determined. Compounds that improve insulin sensitivity in these models will decrease both plasma glucose and insulin levels when compared to the vehicle-treated control group.

Insulin Secretion

Compounds that enhance insulin secretion from the pancreas will increase plasma insulin levels and improve the disappearance of plasma glucose following the administration of a glucose load. When measuring insulin levels, compounds are administered by different routes (p.o., i.p., s.c. or i.v.) to overnight fasted normal rats or mice. At the appropriate time an intravenous glucose load (0.4 g/kg) is given, blood is collected one minute later. Plasma insulin levels are determined. Compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60 and 90 minutes and plasma glucose levels determined. Compounds that increase insulin levels will decrease glucose levels and the area-under-the glucose curve when compared to the vehicle-treated group given only glucose.

Compounds that enhance insulin secretion from the pancreas will increase plasma insulin levels and improve the disappearance of plasma glucose following the administration of a glucose load. When measuring insulin levels, test compounds which regulate serine/threonine kinase are administered by different routes (p.o., i.p., s.c., or i.v.) to overnight fasted normal rats or mice. At the appropriate time an intravenous glucose load (0.4 g/kg) is given, blood is collected one minute later. Plasma insulin levels are determined. Test compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60, and 90 minutes and plasma glucose levels determined. Test compounds that increase insulin levels will decrease glucose levels and the area-under-the glucose curve when compared to the vehicle-treated group given only glucose.

EXAMPLE 10

In Vivo Testing of Compounds/Target Validation for the Treatment of Peripheral and Central Nervous System Disorders Pain Acute pain. Acute pain is measured on a hot plate mainly in rats. Two variants of hot plate testing are used: In the classical variant animals are put on a hot surface (52 to 56° C.) and the latency time is measured until the animals show nocifensive-behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

Persistent pain. Persistent pain is measured with the formalin or capsaicin test, mainly in rats. A solution of 1 to 5% formalin or 10 to 100 µg capsaicin is injected into one hind paw of the experimental animal. After formalin or capsaicin application the animals show nocifensive reactions like flinching, licking and biting of the affected paw. The number of nocifensive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

Neuropathic pain. Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve. The second variant is the tight ligation of about the half of the diameter of the common sciatic nerve. In the next variant, a group of models is used in which tight ligations or transections are made of either the L5 and L6 spinal nerves, or the L % spinal nerve only. The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10° C. where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadanian rhythms in activity (Surjo and Arndt, Universität zu Köln, Cologne, Germany), and by scoring differences in gait (foot print patterns; FOOTPRINTS program, Klapdor et al., 1997. A low cost method to analyze footprint patterns. J. Neurosci. Methods 75, 49–54).

Compounds are tested against sham operated and vehicle treated control groups. Substance application is performed at different time points via different application routes (i.v., i.p., p.o., i.t., i.c.v., s.c., intradermal, transdermal) prior to pain testing.

Inflammatory Pain. Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed.

The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

Diabetic neuropathic pain. Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

Parkinson's disease

6-Hydroxydopamine (6-OH-DA) Lesion. Degeneration of the dopaminergic nigrostriatal and striatopallidal pathways is the central pathological event in Parkinson's disease. This disorder has been mimicked experimentally in rats using single/sequential unilateral stereotaxic injections of 6-OH-DA into the medium forebrain bundle (MFB).

Male Wistar rats (Harlan Winkelmann, Germany), weighing 200±250 g at the beginning of the experiment, are used. The rats are maintained in a temperature- and humidity-controlled environment under a 12 h light/dark cycle with free access to food and water when not in experimental sessions. The following in vivo protocols are approved by the governmental authorities. All efforts are made to minimize animal suffering, to reduce the number of animals used, and to utilize alternatives to in vivo techniques.

Animals are administered pargyline on the day of surgery (Sigma, St. Louis, Mo., USA; 50 mg/kg i.p.) in order to inhibit metabolism of 6-OHDA by monoamine oxidase and desmethylimipramine HCl (Sigma; 25 mg/kg i.p.) in order to prevent uptake of 6-OHDA by noradrenergic terminals. Thirty minutes later the rats are anesthetized with sodium pentobarbital (50 mg/kg) and placed in a stereotaxic frame. In order to lesion the DA nigrostriatal pathway 4 µl of 0.01% ascorbic acid-saline containing 8 µg of 6-OHDA HBr (Sigma) are injected into the left medial fore-brain bundle at a rate of 1 µl/min (2.4 mm anterior, 1.49 mm lateral, −2.7 mm ventral to Bregma and the skull surface). The needle is left in place an additional 5 min to allow diffusion to occur.

Stepping Test. Forelimb akinesia is assessed three weeks following lesion placement using a modified stepping test protocol. In brief, the animals are held by the experimenter with one hand fixing the hindlimbs and slightly raising the hind part above the surface. One paw is touching the table, and is then moved slowly sideways (5 s for 1 m), first in the forehand and then in the backhand direction. The number of adjusting steps is counted for both paws in the backhand and forehand direction of movement. The sequence of testing is right paw forehand and backhand adjusting stepping, followed by left paw forehand and backhand directions. The test is repeated three times on three consecutive days, after an initial training period of three days prior to the first testing. Forehand adjusted stepping reveals no consistent differences between lesioned and healthy control animals. Analysis is therefore restricted to backhand adjusted stepping.

Balance Test. Balance adjustments following postural challenge are also measured during the stepping test sessions. The rats are held in the same position as described in the stepping test and, instead of being moved sideways, tilted by the experimenter towards the side of the paw touching the table. This maneuver results in loss of balance and the ability of the rats to regain balance by forelimb movements is scored on a scale ranging from 0 to 3. Score 0 is given for a normal forelimb placement. When the forelimb movement is delayed but recovery of postural balance detected, score 1 is given. Score 2 represents a clear, yet insufficient, forelimb reaction, as evidenced by muscle contraction, but lack of success in recovering balance, and score 3 is given for no reaction of movement. The test is repeated three times a day on each side for three consecutive days after an initial training period of three days prior to the first testing.

Staircase Test (Paw-Reaching). A modified version of the staircase test is used for evaluation of paw reaching behavior three weeks following primary and secondary lesion placement. Plexiglass test boxes with a central platform and a removable staircase on each side are used. The apparatus is designed such that only the paw on the same side at each staircase can be used, thus providing a measure of independent forelimb use. For each test the animals are left in the test boxes for 15 min. The double staircase is filled with 7×3 chow pellets (Precision food pellets, formula: P, purified rodent diet, size 45 mg; Sandown Scientific) on each side. After each test the number of pellets eaten (successfully retrieved pellets) and the number of pellets taken (touched but dropped) for each paw and the success rate (pellets eaten/pellets taken) are counted separately. After three days of food deprivation (12 g per animal per day) the animals are tested for 11 days. Full analysis is conducted only for the last five days.

MPTP treatment. The neurotoxin 1-methyl4phenyl-1,2,3,6-tetrahydropyridine (MPTP) causes degeneration of mesencephalic dopaminergic (DAergic) neurons in rodents, non-human primates, and humans and, in so doing, reproduces many of the symptoms of Parkinson's disease. MPTP leads to a marked decrease in the levels of dopamine and its metabolites, and in the number of dopaminergic terminals in the striatum as well as severe loss of the tyrosine hydroxylase (TH)-immunoreactive cell bodies in the substantia nigra, pars compacta.

In order to obtain severe and long-lasting lesions, and to reduce mortality, animals receive single injections of MPTP, and are then tested for severity of lesion 7–10 days later. Successive MPTP injections are administered on days 1, 2 and 3. Animals receive application of 4 mg/kg MPTP hydrochloride (Sigma) in saline once daily. All injections are intraperitoneal (i.p.) and the MPTP stock solution is frozen between injections. Animals are decapitated on day 11.

Immunohistology. At the completion of behavioral experiments, all animals are anaesthetized with 3 ml thiopental (1 g/40 ml i.p., Tyrol Pharma). The mice are perfused transcardially with 0.01 M PBS (pH 7.4) for 2 min, followed by 4% paraformaldehyde (Merck) in PBS for 15 min. The brains are removed and placed in 4% paraformaldehyde for 24 h at 4° C. For dehydration they are then transferred to a 20% sucrose (Merck) solution in 0.1 M PBS at 4° C. until they sink. The brains are frozen in methylbutan at −20° C. for 2 min and stored at −70° C. Using a sledge microtome (mod. 3800-Frigocut, Leica), 25 µm sections are taken from the genu of the corpus callosum (AP 1.7 mm) to the hippocampus (AP 21.8 mm) and from AP 24.16 to AP 26.72. Forty-six sections are cut and stored in assorters in 0.25 M Tris buffer (pH 7.4) for immunohistochemistry.

A series of sections is processed for free-floating tyrosine hydroxylase (TH) immunohistochemistry. Following three rinses in 0.1 M PBS, endogenous peroxidase activity is quenched for 10 min in 0.3% $H_2O_2$±PBS. After rinsing in PBS, sections are preincubated in 10% normal bovine serum (Sigma) for 5 min as blocking agent and transferred to either primary anti-rat TH rabbit antiserum (dilution 1:2000).

Following overnight incubation at room temperature, sections for TH immuno-reactivity are rinsed in PBS (2×10 min) and incubated in biotinylated anti-rabbit immunoglobulin G raised in goat (dilution 1:200) (Vector) for 90 min, rinsed repeatedly and transferred to Vectastain ABC (sector) solution for 1 h. 3,3'-Diaminobenzidine tetrahydrochloride (DAB; Sigma) in 0.1 M PBS, supplemented with 0.005% $H_2O_2$, serves as chromogen in the subsequent visualization reaction. Sections are mounted on to gelatin-coated slides, left to dry overnight, counter-stained with hematoxylin dehydrated in ascending alcohol concentrations and cleared in butylacetate. Coverslips are mounted on entellan.

Rotarod Test. We use a modification of the procedure described by Rozas and Labandeira-Garcia (1997), with a CR-1 Rotamex system (Columbus Instruments, Columbus, Ohio) comprising an IBM-compatible personal computer, a CIO-24 data acquisition card, a control unit, and a four-lane rotarod unit. The rotarod unit consists of a rotating spindle (diameter 7.3 cm) and individual compartments for each mouse. The system software allows preprogramming of session protocols with varying rotational speeds (0–80 rpm). Infrared beams are used to detect when a mouse has fallen onto the base grid beneath the rotarod. The system logs the fall as the end of the experiment for that mouse, and the total time on the rotarod, as well as the time of the fall and all the set-up parameters, are recorded. The system also allows a weak current to be passed through the base grid, to aid training.

Dementia

The object recognition task. The object recognition task has been designed to assess the effects of experimental manipulations on the cognitive performance of rodents. A rat is placed in an open field, in which two identical objects are present. The rats inspects both objects during the first trial of the object recognition task. In a second trial, after a retention interval of for example 24 hours, one of the two objects used in the first trial, the 'familiar' object, and a novel object are placed in the open field. The inspection time at each of the objects is registered. The basic measures in the OR task is the time spent by a rat exploring the two object the second trial. Good retention is reflected by higher exploration times towards the novel than the 'familiar' object.

Administration of the putative cognition enhancer prior to the first trial predominantly allows assessment of the effects on acquisition, and eventually on consolidation processes. Administration of the testing compound after the first trial allows to assess the effects on consolidation processes, whereas administration before the second trial allows to measure effects on retrieval processes.

The passive avoidance task. The passive avoidance task assesses memory performance in rats and mice. The inhibitory avoidance apparatus consists of a two-compartment box with a light compartment and a dark compartment. The two compartments are separated by a guillotine door that can be operated by the experimenter. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. In the habituation sessions and the retention session the rat is allowed to explore the apparatus for 300 sec. The rat is placed in the light compartment, facing the wall opposite to the guillotine door. After an accommodation period of 15 sec. the guillotine door is opened so that all parts of the apparatus can be visited freely. Rats normally avoid brightly lit areas and will enter the dark compartment within a few seconds.

In the shock session the guillotine door between the compartments is lowered as soon as the rat has entered the dark compartment with its four paws, and a scrambled 1 mA footshock is administered for 2 sec. The rat is removed from the apparatus and put back into its home cage. The procedure during the retention session is identical to that of the habituation sessions.

The step-through latency, that is the first latency of entering the dark compartment (in sec.) during the retention session is an index of the memory performance of the animal; the longer the latency to enter the dark compartment; the better the retention is. A testing compound in given half an hour before the shock session, together with 1 mg*kg$^{-1}$ scopolamine. Scopolamine impairs the memory performance during the retention session 24 hours later. If the test compound increases the enter latency compared with the scopolamine-treated controls, is likely to possess cognition enhancing potential.

The Morris water escape task. The Morris water escape task measures spatial orientation learning in rodents. It is a test system that has extensively been used to investigate the effects of putative therapeutic on the cognitive functions of rats and mice. The performance of an animal is assessed in a circular water tank with an escape platform that is submerged about 1 cm below the surface of the water. The escape platform is not visible for an animal swimming in the water tank. Abundant extra-maze cues are provided by the furniture in the room, including desks, computer equipment, a second water tank, the presence of the experimenter, and by a radio on a shelf that is playing softly.

The animals receive four trials during five daily acquisition sessions. A trial is started by placing an animal into the pool, facing the wall of the tank. Each of four starting positions in the quadrants north, east, south, and west is used once in a series of four trials; their order is randomized. The escape platform is always in the same position. A trial is terminated as soon as the animal had climbs onto the escape platform or when 90 seconds have elapsed, whichever event occurs first. The animal is allowed to stay on the platform for 30 seconds. Then it is taken from the platform and the next trial is started. If an animal did not find the platform within 90 seconds it is put on the platform by the experimenter and is allowed to stay there for 30 seconds. After the fourth trial of the fifth daily session, an additional trial is given as a probe trial: the platform is removed, and the time the animal spends in the four quadrants is measured for 30 or 60 seconds. In the probe trial, all animals start from the same start position, opposite to the quadrant where the escape platform had been positioned during acquisition.

Four different measures are taken to evaluate the performance of an animal during acquisition training: escape latency, traveled distance, distance to platform, and swimming speed. The following measures are evaluated for the probe trial: time (s) in quadrants and traveled distance (cm) in the four quadrants. The probe trial provides additional information about how well an animal learned the position of the escape platform. If an animal spends more time and swims a longer distance in the quadrant where the platform had been positioned during the acquisition sessions than in any other quadrant, one concludes that the platform position has been learned well.

In order to assess the effects of putative cognition enhancing compounds, rats or mice with specific brain lesions which impair cognitive functions, or animals treated with compounds such as scopolamine or MK-801, which interfere with normal learning, or aged animals which suffer from cognitive deficits, are used.

The T-maze spontaneous alternation task. The T-maze spontaneous alternation task (TeMCAT) assesses the spatial memory performance in mice. The start arm and the two goal arms of the T-maze are provided with guillotine doors which can be operated manually by the experimenter. A mouse is put into the start arm at the beginning of training. The guillotine door is closed. In the first trial, the 'forced trial', either the left or right goal arm is blocked by lowering the guillotine door. After the mouse has been released from the start arm, it will negotiate the maze, eventually enter the open goal arm, and return to the start position, where it will be confined for 5 seconds, by lowering the guillotine door. Then, the animal can choose freely between the left and right goal arm (all guillotine-doors opened) during 14 'free choice' trials. As soon a the mouse has entered one goal arm, the other one is closed. The mouse eventually returns to the start arm and is free to visit whichever go alarm it wants after having been confined to the start arm for 5 seconds. After completion of 14 free choice trials in one session, the animal is removed from the maze. During training, the animal is never handled.

The percent alternations out of 14 trials is calculated. This percentage and the total time needed to complete the first forced trial and the subsequent 14 free choice trials (in s) is analyzed. Cognitive deficits are usually induced by an injection of scopolamine, 30 min before the start of the training session. Scopolamine reduced the per-cent alternations to chance level, or below. A cognition enhancer, which is always administered before the training session, will at least partially, antagonize the scopolamine-induced reduction in the spontaneous alternation rate.

EXAMPLE 11

Identification of Test Compound Efficacy in an Animal Model of COPD

A/J mice are exposed to the smoke from 2 unfiltered cigarettes per day for 6 days per week for 14 weeks. Non-smoking, age-matched animals are used as controls. Animals are orally dosed with test compound or vehicle 1 hour before and 7 hours after smoke exposure. This twice-daily dosing regime is continued throughout the smoke exposure period. On day 7 of the weekly exposure, animals are given only 1 dose of test compound and are not exposed to cigarette smoke.

After the smoke exposure period, the mice are killed, their lungs inflated with phosphate-buffered formalin via their trachea, and then the lungs and heart are removed en bloc and fixed at 4° C. for 48 hours. The lungs are then prepared for paraffin wax sectioning, and 4 mm sections are cut and mounted on glass slides. Sections are then stained with haematoxylin and eosin. Morphometric analysis of lung sections is done by calculation of the Linear Mean Intercept (LMI) parameter using a semi-automated computer image analysis system. Each slide (1 per mouse) contains several sections originating from multiple lobes. Twelve non-overlapping areas (each area covering $1.53 \times 10-3$ cm$^2$) are randomly selected for LMI analysis. The 12 areas cover a minimum of two lobes per slide. Non-parenchymal components (airways, blood vessels) are excluded from the analysis to prevent artifactual error. The mean intercept length is calculated for each mouse. Development of emphysema is seen as an increase in LMI.

LMI data are expressed as the median and statistical comparisons are done using the non-parametric Mann-Witney U-test. A 'p' value of $<=0.05$ is considered to be statistically significant. The potency of a test compound is evaluated by comparison of the tobacco smoke induced increase in LMI in animals dosed with either the test compound or just the vehicle used for administration of the compound.

EXAMPLE 12

Identification of Test Compound Efficacy in an in Vitro Functional Test Relevant to COPD The potency of test compounds is evaluated by measuring the inhibition of elastolysis induced by human alveolar macrophages. The cells are isolated from bronchoalveolar lavage samples taken from non-smokers, disease-free smokers, and smokers with COPD. Macrophage suspensions are added to test wells coated with tritiated elastin and incubated at 37° C. for 3 h to allow adherence of the cells. The wells are then carefully washed to remove non-adherent cells and fresh medium is added to each well. The cells are incubated at 37° C. for up to 72 hours in the presence or absence of test compound. Every 24 hours the medium in each well is removed for analysis and replaced by fresh medium. Radioactivity released into the medium is measured by liquid scintillation counting and the rate of elastin degradation is calculated. The potency of a test compound is evaluated by comparing the rate of elastolysis measured with cells incubated in the presence or absence of the compound.

Guinea pigs are exposed on a single occasion to tobacco smoke for 50 minutes. Animals are sacrificed between 10 minutes and 24 hour following the end of the exposure and their lungs placed in RNAlater™. The lung tissue is homogenised, and total RNA was extracted using a Qiagen RNeasy™ Maxi kit. Molecular Probes RiboGreen™ RNA quantitation method is used to quantify the amount of RNA in each sample.

Total RNA is reverse transcribed, and the resultant cDNA is used in a real-time polymerase chain reaction (PCR). The cDNA is added to a solution containing the sense and anti-sense primers and the 6-carboxy-tetramethyl-rhodamine labeled probe of the serine/threonine kinase gene. Cyclophilin is used as the housekeeping gene. The expression of the serine/threonine kinase gene is measured using the TaqMan real-time PCR system that generates an amplification curve for each sample. From this curve a threshold cycle value is calculated: the fractional cycle number at which the amount of amplified target reaches a fixed threshold. A sample containing many copies of the serine/threonine kinase gene will reach this threshold earlier than a sample containing fewer copies. The threshold is set at 0.2, and the threshold cycle CT is calculated from the amplification curve. The CT value for the serine/threonine kinase gene is normalized using the CT value for the housekeeping gene.

Expression of the serine/threonine kinase gene is increased by at least 3-fold between 10 minutes and 3 hours post tobacco smoke exposure compared to air exposed control animals.

Test compounds are evaluated as follows. Animals are pre-treated with a test compound between 5 minutes and 1 hour prior to the tobacco smoke exposure and they are then sacrificed up to 3 hours after the tobacco smoke exposure has been completed. Control animals are pre-treated with the vehicle of the test compound via the route of adiministration chosen for the test compound. A test compound that reduces the tobacco smoke induced upregulation of serine/threonine kinase gene relative to the expression seen in vehicle treated tobacco smoke exposed animals is identified as an inhibitor of serine/threonine kinase gene expression.

EXAMPLE 13

In Vivo Testing of Compounds/Target Validation for the Treatment of Genito-urinary Diseases:

Bladder Outlet Obstruction Model

Wistar rats (200~250 g/Charles River Japan) are anesthetized intraperitoneally with ketamine. The abdomen is opened through a midline incision and the bladder and the proximal urethra are exposed. A constant degree of urethral obstruction is produced by tying a ligature around the urethra and a catheter with an outer diameter of 1 mm. The abdominal well is closed and the animals allowed to recover.

After 6 weeks, the rats are anesthetized with ketamine, and the ligature around the urethra is carefully removed to normalize the outlet resistance and enable repetitive micturition. A polyethylene catheter is implanted in the bladder through the dome, and exteriorized at the scapular level. Animals are then allowed to recover for at least 48 hours.

Cytometric investigation is performed without anesthesia two days after bladder catheter implantation in control and obstructed animals. The bladder catheter was connected via a T-tube to a strain gauge and a microinjection pump. The conscious rats are held under partial restraint in a restraining device. Warmed saline is infused into the bladder at a rate of 3 ml/hr for control and obstructed animals. The rate of infusion is increased from 3 to 10 ml/hr to obtain similar interval times between micturitions in obstructed and control rats. Overactivity of the obstructed bladders is assessed by measuring the cystometric parameters such as basal pressure, peak micturition pressure, threshold pressure, micturition interval, amplitude and frequency of spontaneous activity and micturition slope. Lluel et al., *J. Urol.* 160, 2253–57, 1998.

A test compound is dissolved in an appropriate vehicle, such as a mixture of ethanol, Tween 80 (ICN Biomedicals Inc.), and saline (1:1:8, v/v/v), is administered intravenously through the catheter.

EXAMPLE 14

In Vivo Testing of Compounds/Target Validation for the Treatment of Genito-urinary Diseases Measurement of the Relaxation Effects on the Rat Prostate Contraction Organ Bath Assay for Measuring Agonist-induced Contraction of Prostate An organ bath assay is employed to measure the agonist-induced contraction of prostate for assessing the biological activity of test compounds (i.e., drug candidates). Male Wistar rats (200~250 g/Charles River Japan) are anesthetized with ether and sacrificed by dislocating the necks. The whole prostate is excised and placed in oxygenated Modified Krebs-Henseleit solution (pH 7.4) of the following composition (112 mM NaCl, 5.9 mM KCl, 1.2 mM $MgCl_2$, 1.2 mM $NaH_2PO_4$, 2 mM $CaCl_2$, 2.5 mM $NaHCO_3$, 12 mM glucose). Ventricle prostate lobes were dissected into several strips depending on the size of prostate. Prostate strips are equilibrated for 60 min in organ bath chambers before any stimulation.

Isometric tension is recorded under an appropriate load. Contractile response to adrenergic agonists or electric field stimulation is determined several times until reproducible responses are obtained. Test compounds are pre-incubated prior to the agonistic or electric stimulation The ratio of each contraction to the negative control is calculated and the effect of the test compounds on the prostate contraction is evaluated.

EXAMPLE 15

In Vivo Testing of Compounds/Target Validation for the Treatment of Genito-urinary Diseases Evaluation of Test Compounds for Micturition Disorders Micturition parameters from cystometry are utilized to evaluate the drug candidates for micturition disorders. Sprague-Dawley rats are anesthetized by intraperitoneal administration of urethane at 1.2 g/kg. The abdomen is opened through a midline incision, and a polyethylene catheter is implanted into the bladder through the dome. In parallel, the inguinal region is incised, and a polyethylene catheter filled with 2 IU/ml of heparin in saline is inserted into a common iliac artery. The bladder catheter is connected via T-tube to a pressure transducer and a mnicroinjection pump. Saline is infused at room temperature into the bladder at a rate of 2.4 ml/hr. Intravesicular pressure is recorded continuously on a chart pen recorder. At least three reproducible micturition cycles are recorded before a test compound administration and used as baseline values. The saline infusion is stopped before administrating compounds. A test compound dissolved in an appropriate vehicle is intraarterially injected 2 min before another intraarterial administration of stimulant such as capsaicin. Relative increases in the induced intravesicular pressure are analyzed from the cystometry data in comparison with the normal micturition patterns. The test compounds-mediated inhibition of the increased bladder pressures is evaluated using Student's t-test. A probability level less than 5% is accepted as significant difference.

EXAMPLE 16

In Vivo Testing of Compounds/Target Validation for the Treatment of Genito-urinary Diseases Measurement of the Relaxation Effects on the Rat Bladder Contraction Organ Bath Assay for Measuring Agonist-induced Contraction of Urinary Bladder An organ bath assay is employed to measure the agonist-induced contraction of urinary bladder for assessing the biological activity of test compounds (i.e., drug candidates). Male Wistar rats (200–250 g/Charles River Japan) are anesthetized with ether and sacrificed by dislocating the necks. The whole urinary bladder is excised and placed in oxygenated Modified Krebs-Henseleit solution (pH 7.4) of the following composition (112 mM NaCl, 5.9 mM KCl, 1.2 mM $MgCl_2$, 1.2 mM $NaH_2PO_4$, 2 mM $CaCl_2$, 2.5 mM $NaHCO_3$, 12 mM glucose).

Isometric tension is recorded under an appropriate load using longitudinal strips of rat detrusor muscle. Bladder strips are equilibrated for 60 minutes before each stimulation. Contractile response to 80 mM KCl is determined at 15 minute intervals until reproducible responses are obtained. The response to KCl is used as an internal standard to evaluate the effect of test compounds.

The effects of test compounds are investigated by incubating the strips with compounds for 30 minutes prior to stimulation with an appropriate agonist or electrical stimulation. One of the preparations made from the same animal serves as a control while others are used for evaluating test compounds. The ratio of each contraction to the internal standard (e.g., a KCl-induced contraction) is calculated, and the effects of the test compounds on the contraction are evaluated.

EXAMPLE 17

In Vivo Testing of Compounds/Target Validation for the Treatment of Genito-urinary Diseases Measurement of Bladder Cystometry in Anesthetized Rats
(1) Animals. Female Sprague-Dawley rats (200–250 g/Charles River Japan) are used.
(2) Catheter implantation. Rats are anesthetized by intraperitoneal administration of urethane (Sigma) at 1.25 g/kg. The abdomen is opened through a midline incision, and a polyethylene catheter (BECTON DICKINSON, PE50) is implanted into the bladder through the dome. In parallel, the inguinal region is incised, and a polyethylene catheter (BECTON DICKINSON, PE50) filled with saline (Otsuka) is inserted into a femoral vein.
(3) Investigation of bladder contraction. The bladder is filled via the catheter by incremental volume of saline until spontaneous bladder contractions occur. The intravesicular pressure is measured a pressure transducer and displayed continuously on a chart recorder. The activity of test compounds is assessed after intravenous administration through a polyethylene cannula inserted into the femoral vein.

Measurement of Bladder Cystometry in Conscious Rats
(1) Animals. Female Sprague-Dawley rats (200–250 g/Charles River Japan) are used.
(2) Catheter implantation. Rats are anesthetized by intramuscular administration of ketamine (75 mg/kg) and xylazine (15 mg/kg). The abdomen is opened through a midline incision, and a polyethylene catheter (BECTON DICKINSON, PE50) is implanted into the bladder through the dome. The catheter is tunneled through subcutis of the animal by needle (14G) to neck. In parallel, the inguinal region is incised, and a polyethylene catheter (BECTON DICKINSON, PE50) filled with saline (Otsuka) is inserted into a femoral vein. The catheter is tunneled through subcutis of the animal by needle to neck.
(3) Cystometric investigation. The bladder catheter is connected via T-tube to a pressure transducer (Viggo-Spectramed Pte Ltd, DT-XXAD) and a mnicroinjection pump (TERUMO). Saline is infused at room temperature into the bladder at a rate of 10 ml/hr. Intravesicular pressure is recorded continuously on a chart pen recorder (Yokogawa). At least three reproducible micturition cycles are recorded before a test compound administration.
(4) Administration of test compounds. A test compound dissolved in the mixture of ethanol, Tween 80 (ICN Biomedicals Inc.) and saline (1:1:8, v/v/v) is administered intravenously through the catheter.

EXAMPLE 18

In Vivo Testing of Compounds/Target Validation for the Treatment of Inflammatory Disorders Mouse Anti-CD3 Induced Cytokine Production Model BALB/c mice are injected with a single intravenous injection of 10 μg of 145-2C11 (purified hamster anti-mouse CD3e monoclonal antibodies, PHARMINGEN). A test compound is administered intraperitoneally 60 min prior to the anti-CD3 mAb injection Blood is collected 90 minutes after the antibody injection. Serum is obtained by centrifugation at 3000 rpm. for 10 min. IL-2 and IL-4 levels in the serum are determined by an ELISA.

Mouse Anti-IgD Induced IgE Production Model

BALB/c mice are injected intravenously with 0.8 mg of purified goat anti-mouse IgD antibody or PBS (defined as day 0). Compound is administered intraperitoneally from day 0 to day 6. On day 7 blood is collected and serum is obtained by centrifugation at 3000 rpm. for 10 min. Serum total levels of IgE are determined by YAMASA's ELISA kit and their Ig subtypes are done by an Ig ELISA KIT (Rougier Biotech's, Montreal, Canada).

Mouse LPS-Induced TNF-α Production Model

BALB/c mice are injected intraperitoneally with LPS (200 μg/mouse). Compound is administered intraperitoneally 1 h before the LPS injection. Blood is collected at 90 min post-LPS injection and plasma is obtained. TNF-α concentration in the sample is determined using an ELISA kit.

Mouse Eotaxin-induced Eosinophilia Model

BALB/c mice are injected intradermally with a 2.5 ml of air on days −6 and −3 to prepare airpouch. On day 0 compound is administered intraperitoneally 60 min before eotaxin injection (3 μg/mouse, i.d.). IL-5 (360 ng/mouse) is injected intravenously 30 min before the eotaxin injection. After 4 h of the eotaxin injection leukocytes in exudate is collected and the number of total cells is counted. The differential cell counts in the exudate are performed by staining with May-Grunwald Gimsa solution.

Mouse D10 Cell Transfer Model

D10.G4.1 cells ($1 \times 10^7$ cells/mouse) containing 2 mg of conalbumin in saline is administered i.v. to AKR mice. After 6 h blood is collected and serum is obtained by centrifugation at 3000 r.p.m. for 10 min. IL-4 and IL-5 level in serum are determined by ELISA kits. Compound is administered intraperitoneally at −4 and +1 h after these cells injection.

Passive Cutaneous Anaphylaxis (PCA) Test in Rats

6 Weeks old male Wistar rats are sensitized intradermally (i.d.) on their shaved backs with 50 μl of 0.1 μg/ml mouse anti-DNP IgE monoclonal antibody (SPE-7) under a light anesthesia. After 24 hours, the rats are challenged intravenously with 1 ml of saline containing 0.6 mg DNP-BSA (30) (LSL CO., LTD) and 0.005 g of Evans blue. Compounds are-injected intraperitoneally (i.p.) 0.5 h prior to antigen injection. Rats without the sensitization, challenge, and compound treatment are used for a blank (control) and rats with sensitization, challenge and vehicle treatment are used to determine a value without inhibition. Thirty min after the challenge, the rats are killed, and the skin of the back is removed. Evans blue dye in the skin is extracted in formamide overnight at 63° C. Then an absorbance at 620 nm is measured to obtain the optical density of the leaked dye.

Percent inhibition of PCA with a compound is calculated as follows:

% inhibition={(mean vehicle value−sample value)/ (mean vehicle value−mean control value)}×100

Anaphylactic Bronchoconstriction in Rats

6 Weeks old male Wistar rats are sensitized intravenously (i.v.) with 10 μg mouse anti-DNP IgE, SPE-7, and 1 days later, the rats are challenged intravenously with 0.3 ml of saline containing 1.5 mg DNP-BSA (30) under anesthesia with urethane (1000 mg/kg, i.p.) and gallamine (50 mg/kg, i.v.). The trachea is cannulated for artificial respiration (2 ml/stroke, 70 strokes/min). Pulmonary inflation pressure (PIP) is recorded through a side-arm of cannula connected to pressure transducer. Change in PIP reflects change of both resistance and compliance of the lungs. To evaluate the drugs, each drug is given i.v. 5 min before challenge.

EXAMPLE 19

In Vivo Target Validation for the Treatment of Atherosclerosis

Effects on plasma cholesterol levels including HDL cholesterol are typically assessed in humanized apo-AI transgenic mice. Modulation of human target proteins can be determined in corresponding transgenic mice (e.g., CETP transgenic mice). 1.5 Triglyceride-lowering is usually evaluated in ob/ob mice or Zucker rats. Animals are fed with normal diets or modified diets (e.g., enriched by 0.5% cholesterol 20% coconut oil). Standard protocols consist of oral applications once daily for 7 to 10 days at doses ranging from 0.1 to 100 mg/kg. The compounds are dissolved (e.g., in Solutol/Ethanol/saline mixtures) and applied by oral gavage or intravenous injection. Before and at the end of the application period, blood samples are typically drawn by retroorbital punctuation. Plasma cholesterol and triglyceride levels are determined with standardized clinical diagnostic kits (e.g., INFINITY™ cholesterol reagent and INFINITY™ triglyceride reagent; Sigma, St. Louis). HDL cholesterol is determined after phosphotungstic acid precipitation of non-HDL lipoproteins or FPLC gel filtration with postcolumn derivatization of cholesterol using the reagents mentioned above. Plasma levels of human apolipoprotein-AI in relevant humanized transgenic mice are measured by immunoturbidimetry (Sigma).

Long-term anti-atherosclerotic potency of drug candidates are evaluated in Apo E-knockout mice. Therefore, animals are fed a standard chow diet (4.5% fat) or a Western diet (20% fat) containing 1 to 100 mg/kg of the respective compounds for 3 to 5 month. Arterial lesions are quantified in serial cryosections of the proximal aorta by staining with Oil Red O and counterstaining with hematoxylin. Lesion area size is determined using a digital imaging system.

EXAMPLE 20

In Vivo Testing of Cardiovascular Effects of Test Compounds

Hemodynamics in Anesthetized Rats

Male Wistar rats weighing 300–350 g (Harlan Winkelmann, Borchen, Germany) are anesthetized with thiopental "Nycomed" (Nycomed, Munich, Germany) 100 mg kg$^{-1}$ i.p. A tracheotomy is performed, and catheters are inserted into the femoral artery for blood pressure and heart rate measurements (Gould pressure transducer and recorder, model RS 3400) and into the femoral vein for substance administration. The animals are ventilated with room air and their body temperature is controlled. Test compounds are administered orally or intravenously.

Hemodynamics in Conscious SHR

Female conscious SHR (Moellegaard/Denmark, 220–290 g) are equipped with implantable radiotelemetry, and a data aquisition system (Data Sciences, St. Paul, Minn., USA), comprising a chronically implantable transducer/transmitter unit equipped with a fluid-filled catheter is used. The transmitter is implanted into the peritoneal cavity, and the sensing catheter is inserted into the descending aorta.

Single administration of test compounds is performed as a solution in Transcutol®/Cremophor®/H$_2$O (10/20/70=v/v/v) given orally by gavage. The animals of control groups only receive the vehicle. Before treatment, mean blood pressure and heart rate of treated and untreated control groups are measured.

Hemodynamics in Anesthetized Dogs

Studies are performed on anesthetized dogs of either sex (body weight between 20–30 kg). Anesthesia is initiated by slow intravenous injection of 25 mg kg$^{-1}$ sodium thiopental (Trapanal®, Byk Gulden, Konstanz, Germany). The anesthesia is continued and maintained throughout the experiment by continuous infusion of 0.04 mg kg$^{-1}$ h$^{-1}$ fentanyl (Fentanyl®, Janssen, Neuss, Germany) and 0.25 mg kg$^{-1}$ h$^{-1}$ droperidol (DihydrobenzperidolR, Janssen, Neuss, Germany). During this anaesthesia, heart rate is as low as 35–40 bpm due to increased vagal tone. Therefore, a parasympathetic blockade is achieved by intermittent injections of atropine (0.1 mg per animal) (AtropinsulfatR, Eifelfango, Bad Neuenahr, Germany). After intubation the animals are artificially ventilated at constant volume (EngströmR 300, Engström, Sweden) with room air enriched with 30% oxygen to maintain an end-tidal CO2 concentration of about 5% (NormocapR, Datex, Finland).

The following catheters are implanted for measurement of cardiovascular parameters: a tip catheter for recording of left ventricular pressure is inserted into the ventricle via the carotid artery (PC350, Millar Instruments, Houston, Tex., USA), a hollow catheter is inserted into the femoral artery and connected to a strain gauge (type 4-327-1, Telos Medical, Upland, Calif., USA for recording of arterial blood pressure, two venous catheters are inserted into either femoral vein and one additional catheter into a forearm vein for application of the anesthetic and drugs, respectively, and an oxymetry catheter for recording of oxygen saturation is inserted into the coronary sinus via the jugular vein (Schwarzer IVH4, München, Germany).

After a left-sided thoracotomy the ramus circumflexus of the left coronary artery (LCX) is freed from connective tissue, and an electromagnetic flow probe (Gould Statham, Oxnard, Calif., USA) is applied for measurement of coronary blood flow. Arterial blood pressure, electrocardiogram (lead II), left ventricular pressure, first derivative of left ventricular pressure (dP/dt), heart rate, coronary blood flow, and oxygen saturation in the coronary sinus are continuously recorded on a pen recorder (Brush, Gould, Cleveland, Ohio, USA). The maximum of dP/dt is used as measure of left ventricular contractility (dP/dtmax). After completion of the instrumentation, an interval of 60 min is allowed for stabilization before the test compound is intravenously applied as bolus injections. Care is taken that all measured cardiovascular parameters have returned to control level before injection of the next dose. Each dose of the test compound is tested at least three times in different animals. The order of injection of the different doses is randomized in each animal.

EXAMPLE 21

Expression Profiling

Total cellular RNA was isolated from cells by one of two standard methods: 1) guanidine isothiocyanate/cesium chloride density gradient centrifugation [Kellogg et al. (1990)]; or with the Tri-Reagent protocol according to the manufacturer's specifications (Molecular Research Center, Inc., Cincinatti, Ohio). Total RNA prepared by the Tri-reagent protocol was treated with DNAse I to remove genomic DNA contamination.

For relative quantitation of the mRNA distribution, total RNA from each cell or tissue source was first reverse transcribed. Eighty-five μg of total RNA was reverse transcribed using 1 μmole random hexamer primers, 0.5 mM each of dATP, dCTP, dGTP and dTTP (Qiagen, Hilden, Germany) and 3000 U RnaseQut (Invitrogen, Groningen, Netherlands) in a final volume of 680 μl. The first strand synthesis buffer and Omniscript reverse transcriptase (2 U/μl) were obtained from (Qiagen, Hilden, Germany). The reaction was incubated at 37° C. for 90 minutes and cooled on ice. The volume was adjusted to 6800 μl with water, yielding a final concentration of 12.5 ng/μl of starting RNA.

For relative quantitation of the distribution of mRNA in cells and tissues the Perkin Elmer ABI Prism R™ 7700 Sequence Detection system or Biorad iCycler was used according to the manufacturer's specifications and protocols. PCR reactions were set up to quantitate expression of the test gene and the housekeeping genes HPRT (hypoxanthine phosphoribosyltransferase), GAPDH (glyceraldehyde-3-phosphate dehydrogenase), β-actin, and others. Forward and reverse primers and probes were designed using the Perkin Elmer ABI Primer Express™ software and were synthesized by TibMolBiol (Berlin, Germany). The forward primer sequence was: Primer1 gaatacgcctaccgatgctc (SEQ ID NO: 21). The reverse primer sequence was Primer2 ctgcctttgctagctggagt (SEQ ID NO: 22). Probe1 tggatcaatttgaacgctctccatcc (SEQ ID NO: 23), labeled with FAM (carboxyfluorescein succinimidyl ester) as the reporter dye and TAMRA (carboxytetramethylrhodamine) as the quencher, was used as a probe. The following reagents were prepared in a total of 25 μl: 1× TaqMan buffer A, 5.5 mM MgCl$_2$, 200 nM of DATP, dCTP, dGTP, and dUTP, 0.025 U/μl AmpliTaq Gold™, 0.01 U/μl AmpErase, and Probe1 tggatcaatttgaacgctctccatcc, forward and reverse primers each at 200 nM, 200 nM, FAM/TAMRA-labeled probe, and 5 μl of template cDNA. Thermal cycling parameters were 2 min at 50° C., followed by 10 min at 95° C., followed by 40 cycles of melting at 95° C. for 15 sec and annealing/extending at 60° C. for 1 min.

Calculation of Corrected CT Values

The CT (threshold cycle) value is calculated as described in the "Quantitative determination of nucleic acids" section. The CF-value (factor for threshold cycle correction) is calculated as follows:

1. PCR reactions were set up to quantitate the housekeeping genes (HKG) for each cDNA sample.
2. $CT_{HKG}$-values (threshold cycle for housekeeping gene) were calculated as described in the "Quantitative determination of nucleic acids" section
3. $CT_{HKG}$-mean values (CT mean value of all HKG tested on one cDNAs) of all HKG for each cDNA are calculated (n=number of HKG):

$$CT_{HKG\text{-}n}\text{-mean value} = (CT_{HKG1}\text{-value} + CT_{HKG2}\text{-value} + \ldots + CT_{HKG\text{-}n}\text{-value})/n$$

4. $CT_{pannel}$ mean value (CT mean value of all HKG in all tested cDNAs)=($CT_{HKG1}$-mean value+$CT_{HKG2}$-mean value+ . . . +$CT_{HKG\text{-}y}$-mean value)/y (y=number of cDNAs)
5. $CF_{cDNA\text{-}n}$ (correction factor for cDNA n)=$CT_{pannel}$-mean value–$CT_{HKG\text{-}n}$-mean value
6. $CT_{cDNA\text{-}n}$ (CT value of the tested gene for the cDNA n)+$CF_{cDNA\text{-}n}$ (correction factor for cDNA n)=$CT_{cor\text{-}cDNA\text{-}n}$ (corrected CT value for a gene on cDNA n)

Calculation of Relative Expression

Definition: highest $CT_{cor\text{-}cDNA\text{-}n} \neq 40$ is defined as $CT_{cor\text{-}cDNA}$ [high]

Relative Expression=$2^{(CTcor\text{-}cDNA[high]-CTcor\text{-}cDNA\text{-}n)}$

Expression was tested in the following tissues: fetal heart, heart, pericardium, heart atrium (fight), heart atrium (left), heart ventricle (left), interventricular septum, fetal aorta, aorta, aorta sclerotic, artery, coronary artery, coronary artery sclerotic, vein, coronary artery smooth muscle primary cells, HUVEC cells, skin, adrenal gland, thyroid, thyroid tumor, pancreas, pancreas liver cirrhosis, esophagus, esophagus tumor, stomach, stomach tumor, colon, colon tumor, small intestine, ileum, ileum tumor, ileum chronic inflammation, rectum, salivary gland, fetal liver, liver, liver cirrhosis, liver tumor, HEP G2 cells, leukocytes (peripheral blood), Jurkat (T-cells), bone marrow, erythrocytes, lymph node, thymus, thrombocytes, bone marrow stromal cells, bone marrow CD71$^+$ cells, bone marrow CD33$^+$ cells, bone marrow CD34$^+$ cells, bone marrow CD15$^+$ cells, cord blood CD71$^+$ cells, spleen, spleen liver cirrhosis, skeletal muscle, adipose, fetal brain, brain, Alzheimer brain, cerebellum, cerebellum (right), cerebellum (left), cerebral cortex, Alzheimer cerebral cortex, frontal lobe, Alzheimer brain frontal lobe, occipital lobe, parietal lobe, temporal lobe, precentral gyrus, postcentral gyms, tonsilla cerebelli, vernis cerebelli, pons, substantia nigra, cerebral meninges, cerebral peduncles, corpus callosum, hippocampus, thalamus, dorsal root ganglia, spinal cord, neuroblastoma SK—N-MC cells, neuroblastoma SH—SY5Y cells, neuroblastoma IMR32 cells, glial tumor H4 cells, glial tumor H4 cells+APP, HEK CNS, HEK CNS+APP, retina, fetal lung, fetal lung fibroblast IMR-90 cells, lung, lung right upper lobe, lung right mid lobe, lung right lower lobe, lung tumor, lung COPD, trachea, cervix, testis, HeLa cells (cervix tumor), placenta, uterus, uterus tumor, ovary, ovary tumor, breast, breast tumor, MDA MB 231 cells (breast tumor), mammary gland, prostate, prostate BPH, bladder, ureter, penis, corpus cavernmosum, fetal kidney, kidney, kidney tumor, and HEK 293 cells.

The results are shown in Table 1.

TABLE 1

| Tissue | Relative Expression |
| --- | --- |
| fetal heart | 596 |
| heart | 4270 |
| pericardium | 1136 |
| heart atrium (right) | 10960 |
| heart atrium (left) | 9281 |
| heart ventricle (left) | 1710 |
| interventricular septum | 10809 |
| fetal aorta | 28 |
| aorta | 2 |
| aorta sclerotic | 1 |
| artery | 5 |
| coronary artery | 5 |
| coronary artery sclerotic | 0 |
| vein | 3 |
| coronary artery smooth muscle primary cells | 49 |
| HUVEC cells | 22 |
| skin | 399 |
| adrenal gland | 413 |
| thyroid | 72 |
| thyroid tumor | 47 |
| pancreas | 181 |
| pancreas liver cirrhosis | 62 |
| esophagus | 201 |
| esophagus tumor | 16 |
| stomach | 198 |
| stomach tumor | 159 |
| colon | 244 |
| colon tumor | 15 |

TABLE 1-continued

| Tissue | Relative Expression |
| --- | --- |
| small intestine | 867 |
| ileum | 942 |
| ileum tumor | 0 |
| ileum chronic inflammation | 102 |
| rectum | 724 |
| salivary gland | 92 |
| fetal liver | 43 |
| liver | 169 |
| liver cirrhosis | 30 |
| liver tumor | 0 |
| HEP G2 cells | 0 |
| leukocytes (peripheral blood) | 194 |
| Jurkat (T-cells) | 2 |
| bone marrow | 26 |
| erythrocytes | 9 |
| lymph node | 47 |
| thymus | 6 |
| thrombocytes | 2 |
| bone marrow stromal cells | 47 |
| bone marrow CD71$^+$ cells | 11 |
| bone marrow CD33$^+$ cells | 0 |
| bone marrow CD34$^+$ cells | 1 |
| bone marrow CD15$^+$ cells | 0 |
| cord blood CD71$^+$ cells | 6 |
| spleen | 29 |
| spleen liver cirrhosis | 0 |
| skeletal muscle | 3083 |
| adipose | 286 |
| fetal brain | 1193 |
| brain | 6889 |
| Alzheimer brain | 6472 |
| cerebellum | 885 |
| cerebellum (right) | 57052 |
| cerebellum (left) | 54350 |
| cerebral cortex | 30362 |
| Alzheimer cerebral cortex | 79024 |
| frontal lobe | 24322 |
| Alzheimer brain frontal lobe | 31216 |
| occipital lobe | 12331 |
| parietal lobe | 23010 |
| temporal lobe | 18561 |
| precentral gyrus | 24662 |
| postcentral gyrus | 474 |
| tonsilla cerebelli | 28924 |
| vermis cerebelli | 11666 |
| pons | 14972 |
| substantia nigra | 0 |
| cerebral meninges | 49 |
| cerebral peduncles | 85285 |
| corpus callosum | 28526 |
| hippocampus | 10587 |
| thalamus | 25180 |
| dorsal root ganglia | 177 |
| spinal cord | 6472 |
| neuroblastoma SK-N-MC cells | 0 |
| neuroblastoma SH-SY5Y cells | 2759 |
| neuroblastoma IMR32 cells | 572 |
| glial tumor H4 cells | 47 |
| glial tumor H4 cells + APP | 33 |
| HEK CNS | 48 |
| HEK CNS + APP | 44 |
| retina | 246 |
| fetal lung | 30 |
| fetal lung fibroblast IMR-90 cells | 120 |
| lung | 803 |
| lung right upper lobe | 25 |
| lung right mid lobe | 42 |
| lung right lower lobe | 25 |
| lung tumor | 41 |
| lung COPD | 45 |
| trachea | 89 |
| cervix | 355 |
| testis | 205 |
| HeLa cells (cervix tumor) | 11 |
| placenta | 79 |
| uterus | 158 |
| uterus tumor | 0 |

TABLE 1-continued

| Tissue | Relative Expression |
| --- | --- |
| ovary | 70 |
| ovary tumor | 0 |
| breast | 704 |
| breast tumor | 9 |
| MDA MB 231 cells (breast tumor) | 27 |
| mammary gland | 22 |
| prostate | 169 |
| prostate BPH | 42 |
| bladder | 87 |
| ureter | 52 |
| penis | 70 |
| corpus cavernosum | 12 |
| fetal kidney | 534 |
| kidney | 205 |
| kidney tumor | 3517 |
| HEK 293 cells | 22 |

REFERENCES

1. Muranyi A, Zhang R, Liu F, Hirano K, Ito M, Epstein H F, Hartshorne D J. Myotonic dystrophy protein kinase phosphorylates the myosin phosphatase targeting subunit and inhibits myosin phosphatase activity. FEBS Lett 2001 Mar. 30;493(2–3):80–4.
2. Endo A, Motonaga K, Arahata K, Harada K, Yamada T, Takashima S. Developmental expression of myotonic dystrophy protein kinase in brain and its relevance to clinical phenotype. Acta Neuropathol (Berl) 2000 November; 100(5):513–20.
3. Lam L T, Pham Y C, Nguyen T M, Morris G E. Characterization of a monoclonal antibody panel shows that the myotonic dystrophy protein kinase, DMPK, is expressed almost exclusively in muscle and heart. Hum Mol Genet 2000 Sep. 1;9(14):2167–73.
4. Shimizu M, Wang W, Walch E T, Dunne P W, Epstein H F. Rac-1 and Raf-1 kinases, components of distinct signaling pathways, activate myotonic dystrophy protein kinase. FEBS Lett 2000 Jun. 23;475(3):273–7.
5. Groenen P J, Wansink D G, Coerwinkel M, van den Broek W, Jansen G, Wieringa B. Constitutive and regulated modes of splicing produce six major myotonic dystrophy protein kinase (DMPK) isoforms with distinct properties. Hum Mol Genet 2000 Mar. 1;9(4):605–16.
6. Jinnai K, Sugio T, Mitani M, Hashimoto K, Takahashi K. Elongation of (CTG)n repeats in myotonic dystrophy protein kinase gene in tumors associated with myotonic dystrophy patients. Muscle Nerve 1999 September; 22(9):1271–4.
7. Mussini I, Biral D, Marin O, Furlan S, Salvatori S. Myotonic dystrophy protein kinase expressed in rat cardiac muscle is associated with sarcoplasmic reticulum and gap junctions. J Histochem Cytochem 1999 March; 47(3):383–92.
8. Pham Y C, Man N, Lam L T, Morris G E. Localization of myotonic dystrophy protein kinase in human and rabbit tissues using a new panel of monoclonal antibodies. Hum Mol Genet 1998 November; 7(12):1957–65.
9. Okoli G, Carey N, Johnson K J, Watt D J. Over expression of the murine myotonic dystrophy protein kinase in the mouse myogenic C2C12 cell line leads to inhibition of terminal differentiation. Biochem Biophys Res Commun 1998 May 29;246(3):905–11.
10. Leung T, Chen X Q, Tan I, Manser E, Lim L. Myotonic dystrophy kinase-related Cdc42-binding kinase acts as a Cdc42 effector in promoting cytoskeletal reorganization. Mol Cell Biol 1998 January; 18(1):130–40.
11. Tan I, Seow K T, Lim L, Leung T. Intermolecular and intramolecular interactions regulate catalytic activity of myotonic dystrophy kinase-related Cdc42-binding kinase alpha. Mol Cell Biol 2001 April; 21(8):2767–78.
12. Kedra D, Seroussi E, Fransson I, Trifunovic J, Clark M, Lagercrantz J, Blennow E, Mehlin H, Dumanski J. The germinal center kinase gene and a novel CDC25-like gene are located in the vicinity of the PYGM gene on 11q13. Hum Genet 1997 October; 100(5–6):611–9.

The invention claimed is:

1. An isolated and purified protein comprising the amino acid sequence shown in SEQ ID NO:2.

\* \* \* \* \*

SEQUENCE LISTING

```
<160> NUMBER OF SEQ ID NOS: 23

<210> SEQ ID NO 1
<211> LENGTH: 5196
<212> TYPE: DNA
<213> ORGANISM: Homo sapiens
<220> FEATURE:
<221> NAME/KEY: CDS
<222> LOCATION: (1)...(5196)

<400> SEQUENCE: 1 atg tct gga gaa gtg cgt ttg agg cag ttg gag cag ttt att ttg gac      48
Met Ser Gly Glu Val Arg Leu Arg Gln Leu Glu Gln Phe Ile Leu Asp
 1               5                  10                  15 ggg ccc gct cag acc aat ggg cag tgc ttc agt gtg gag aca tta ctg      96
Gly Pro Ala Gln Thr Asn Gly Gln Cys Phe Ser Val Glu Thr Leu Leu
                20                  25                  30 gat ata ctc atc tgc ctt tat gat gaa tgc aat aat tct cca ttg aga     144
Asp Ile Leu Ile Cys Leu Tyr Asp Glu Cys Asn Asn Ser Pro Leu Arg
```

-continued

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  |  | 45 |  |  |  |  |
| aga | gag | aag | aac | att | ctc | gaa | tac | cta | gaa | tgg | gct | aaa | cca | ttt | act | 192 |
| Arg | Glu | Lys | Asn | Ile | Leu | Glu | Tyr | Leu | Glu | Trp | Ala | Lys | Pro | Phe | Thr |
|  | 50 |  |  |  | 55 |  |  |  |  | 60 |  |  |  |  |  |
| tct | aaa | gtg | aaa | caa | atg | cga | tta | cat | aga | gaa | gac | ttt | gaa | ata | tta | 240 |
| Ser | Lys | Val | Lys | Gln | Met | Arg | Leu | His | Arg | Glu | Asp | Phe | Glu | Ile | Leu |
| 65 |  |  |  |  | 70 |  |  |  |  | 75 |  |  |  |  | 80 |
| aag | gtg | att | ggt | cga | gga | gct | ttt | ggg | gag | gtt | gct | gta | gta | aaa | cta | 288 |
| Lys | Val | Ile | Gly | Arg | Gly | Ala | Phe | Gly | Glu | Val | Ala | Val | Val | Lys | Leu |
|  |  |  |  | 85 |  |  |  |  | 90 |  |  |  |  | 95 |  |
| aaa | aat | gca | gat | aaa | gtg | ttt | gcc | atg | aaa | ata | ttg | aat | aaa | tgg | gaa | 336 |
| Lys | Asn | Ala | Asp | Lys | Val | Phe | Ala | Met | Lys | Ile | Leu | Asn | Lys | Trp | Glu |
|  |  |  | 100 |  |  |  |  | 105 |  |  |  |  | 110 |  |  |
| atg | ctg | aaa | aga | gct | gag | aca | gca | tgt | ttt | cgt | gaa | gaa | agg | gat | gta | 384 |
| Met | Leu | Lys | Arg | Ala | Glu | Thr | Ala | Cys | Phe | Arg | Glu | Glu | Arg | Asp | Val |
|  |  | 115 |  |  |  |  | 120 |  |  |  |  | 125 |  |  |  |
| tta | gtg | aat | gga | gac | aat | aaa | tgg | att | aca | acc | ttg | cac | tat | gct | ttc | 432 |
| Leu | Val | Asn | Gly | Asp | Asn | Lys | Trp | Ile | Thr | Thr | Leu | His | Tyr | Ala | Phe |
| 130 |  |  |  |  | 135 |  |  |  |  | 140 |  |  |  |  |  |
| cag | gat | gac | aat | aac | tta | tac | ctg | gtt | atg | gat | tat | tat | gtt | ggt | ggg | 480 |
| Gln | Asp | Asp | Asn | Asn | Leu | Tyr | Leu | Val | Met | Asp | Tyr | Tyr | Val | Gly | Gly |
| 145 |  |  |  |  | 150 |  |  |  |  | 155 |  |  |  |  | 160 |
| gat | ttg | ctt | act | cta | ctc | agc | aaa | ttt | gaa | gat | aga | ttg | cct | gaa | gat | 528 |
| Asp | Leu | Leu | Thr | Leu | Leu | Ser | Lys | Phe | Glu | Asp | Arg | Leu | Pro | Glu | Asp |
|  |  |  |  | 165 |  |  |  |  | 170 |  |  |  |  | 175 |  |
| atg | gct | aga | ttt | tac | ttg | gct | gag | atg | gtg | ata | gca | att | gac | tca | gtt | 576 |
| Met | Ala | Arg | Phe | Tyr | Leu | Ala | Glu | Met | Val | Ile | Ala | Ile | Asp | Ser | Val |
|  |  |  | 180 |  |  |  |  | 185 |  |  |  |  | 190 |  |  |
| cat | cag | cta | cat | tat | gta | cac | aga | gac | att | aaa | cct | gac | aat | ata | ctg | 624 |
| His | Gln | Leu | His | Tyr | Val | His | Arg | Asp | Ile | Lys | Pro | Asp | Asn | Ile | Leu |
|  |  | 195 |  |  |  |  | 200 |  |  |  |  | 205 |  |  |  |
| atg | gat | atg | aat | gga | cat | att | cgg | tta | gca | gat | ttt | ggt | tct | tgt | ctg | 672 |
| Met | Asp | Met | Asn | Gly | His | Ile | Arg | Leu | Ala | Asp | Phe | Gly | Ser | Cys | Leu |
| 210 |  |  |  |  | 215 |  |  |  |  | 220 |  |  |  |  |  |
| aag | ctg | atg | gaa | gat | gga | acg | gtt | cag | tcc | tca | gtg | gct | gta | gga | act | 720 |
| Lys | Leu | Met | Glu | Asp | Gly | Thr | Val | Gln | Ser | Ser | Val | Ala | Val | Gly | Thr |
| 225 |  |  |  |  | 230 |  |  |  |  | 235 |  |  |  |  | 240 |
| cca | gat | tat | atc | tct | cct | gaa | atc | ctt | caa | gcc | atg | gaa | gat | gga | aaa | 768 |
| Pro | Asp | Tyr | Ile | Ser | Pro | Glu | Ile | Leu | Gln | Ala | Met | Glu | Asp | Gly | Lys |
|  |  |  |  | 245 |  |  |  |  | 250 |  |  |  |  | 255 |  |
| ggg | aga | tat | gga | cct | gaa | tgt | gac | tgg | tgg | tct | ttg | ggg | gtc | tgt | atg | 816 |
| Gly | Arg | Tyr | Gly | Pro | Glu | Cys | Asp | Trp | Trp | Ser | Leu | Gly | Val | Cys | Met |
|  |  |  | 260 |  |  |  |  | 265 |  |  |  |  | 270 |  |  |
| tat | gaa | atg | ctt | tac | gga | gaa | aca | cca | ttt | tat | gca | gaa | tcg | ctg | gtg | 864 |
| Tyr | Glu | Met | Leu | Tyr | Gly | Glu | Thr | Pro | Phe | Tyr | Ala | Glu | Ser | Leu | Val |
|  |  | 275 |  |  |  |  | 280 |  |  |  |  | 285 |  |  |  |
| gag | aca | tac | gga | aaa | atc | atg | aac | cac | aaa | gag | agg | ttt | cag | ttt | cca | 912 |
| Glu | Thr | Tyr | Gly | Lys | Ile | Met | Asn | His | Lys | Glu | Arg | Phe | Gln | Phe | Pro |
|  | 290 |  |  |  |  | 295 |  |  |  |  | 300 |  |  |  |  |
| gcc | caa | gtg | act | gat | gtg | tct | gaa | aat | gct | aag | gat | ctt | att | cga | agg | 960 |
| Ala | Gln | Val | Thr | Asp | Val | Ser | Glu | Asn | Ala | Lys | Asp | Leu | Ile | Arg | Arg |
| 305 |  |  |  |  | 310 |  |  |  |  | 315 |  |  |  |  | 320 |
| ctc | att | tgt | agc | aga | gaa | cat | cga | ctt | ggt | caa | aat | gga | ata | gaa | gac | 1008 |
| Leu | Ile | Cys | Ser | Arg | Glu | His | Arg | Leu | Gly | Gln | Asn | Gly | Ile | Glu | Asp |
|  |  |  |  | 325 |  |  |  |  | 330 |  |  |  |  | 335 |  |
| ttt | aag | aaa | cac | cca | ttt | ttc | agt | gga | att | gat | tgg | gat | aat | att | cgg | 1056 |
| Phe | Lys | Lys | His | Pro | Phe | Phe | Ser | Gly | Ile | Asp | Trp | Asp | Asn | Ile | Arg |
|  |  |  | 340 |  |  |  |  | 345 |  |  |  |  | 350 |  |  |
| aac | tgt | gaa | gca | cct | tat | att | cca | gaa | gtt | agt | agc | cca | aca | gat | aca | 1104 |

```
                Asn Cys Glu Ala Pro Tyr Ile Pro Glu Val Ser Ser Pro Thr Asp Thr
                                355                 360                 365 tcg aat ttt gat gta gat gat gat tgt tta aaa aat tct gaa acg atg              1152
Ser Asn Phe Asp Val Asp Asp Asp Cys Leu Lys Asn Ser Glu Thr Met
        370                 375                 380 ccc cca cca aca cat act gca ttt tct ggc cat ctg cca ttt gtt                  1200
Pro Pro Pro Thr His Thr Ala Phe Ser Gly His His Leu Pro Phe Val
385                 390                 395                 400 ggt ttt aca tat act agt agc tgt gta ctt tct gat cgg agc tgt tta              1248
Gly Phe Thr Tyr Thr Ser Ser Cys Val Leu Ser Asp Arg Ser Cys Leu
                405                 410                 415 aga gtt acg gct ggt ccc acc tca ctg gat ctt gat gtt aat gtt cag              1296
Arg Val Thr Ala Gly Pro Thr Ser Leu Asp Leu Asp Val Asn Val Gln
        420                 425                 430 agg act cta gac aac aac tta gca act gaa gct tat gaa aga aga att              1344
Arg Thr Leu Asp Asn Asn Leu Ala Thr Glu Ala Tyr Glu Arg Arg Ile
435                 440                 445 aag cgc ctt gag caa gaa aaa ctt gaa ctc agt aga aaa ctt caa gag              1392
Lys Arg Leu Glu Gln Glu Lys Leu Glu Leu Ser Arg Lys Leu Gln Glu
        450                 455                 460 tca aca cag act gtc caa gct ctg cag tat tca act gtt gat ggt cca              1440
Ser Thr Gln Thr Val Gln Ala Leu Gln Tyr Ser Thr Val Asp Gly Pro
465                 470                 475                 480 cta aca gca agc aaa gat tta gaa ata aaa aac tta aaa gaa gaa att              1488
Leu Thr Ala Ser Lys Asp Leu Glu Ile Lys Asn Leu Lys Glu Glu Ile
                485                 490                 495 gaa aaa cta aga aaa caa gta aca gaa tca agt cat ttg gaa cag caa              1536
Glu Lys Leu Arg Lys Gln Val Thr Glu Ser Ser His Leu Glu Gln Gln
                500                 505                 510 ctt gaa gaa gct aat gct gtg agg caa gaa cta gat gat gct ttt aga              1584
Leu Glu Glu Ala Asn Ala Val Arg Gln Glu Leu Asp Asp Ala Phe Arg
        515                 520                 525 caa atc aag gct tat gaa aaa caa atc aaa acg tta caa caa gaa aga              1632
Gln Ile Lys Ala Tyr Glu Lys Gln Ile Lys Thr Leu Gln Gln Glu Arg
530                 535                 540 gaa gat cta aat aag gaa cta gtc cag gct agt gag cga tta aaa aac              1680
Glu Asp Leu Asn Lys Glu Leu Val Gln Ala Ser Glu Arg Leu Lys Asn
545                 550                 555                 560 caa tcc aaa gag ctg aaa gac gca cac tgt cag agg aaa ctg gcc atg              1728
Gln Ser Lys Glu Leu Lys Asp Ala His Cys Gln Arg Lys Leu Ala Met
                565                 570                 575 cag gaa ttc atg gag atc aat gag cgg cta aca gaa ttg cac acc caa              1776
Gln Glu Phe Met Glu Ile Asn Glu Arg Leu Thr Glu Leu His Thr Gln
                580                 585                 590 aaa cag aaa ctt gct cgc cat gtc cga gat aag gaa gaa gag gtg gac              1824
Lys Gln Lys Leu Ala Arg His Val Arg Asp Lys Glu Glu Glu Val Asp
        595                 600                 605 ctg gtg atg caa aaa gtt gaa agc tta agg caa gaa ctg cgc aga aca              1872
Leu Val Met Gln Lys Val Glu Ser Leu Arg Gln Glu Leu Arg Arg Thr
        610                 615                 620 gaa aga gcc aaa aaa gag gtt agt att cat aca gaa gct cta gct gct              1920
Glu Arg Ala Lys Lys Glu Val Ser Ile His Thr Glu Ala Leu Ala Ala
625                 630                 635                 640 gaa gca tct aaa gac agg aag cta cgt gaa cag agt gag cac tat tct              1968
Glu Ala Ser Lys Asp Arg Lys Leu Arg Glu Gln Ser Glu His Tyr Ser
                645                 650                 655 aag caa ctg gaa aat gaa ttg gag gga ctg aag caa aaa caa att agt              2016
Lys Gln Leu Glu Asn Glu Leu Glu Gly Leu Lys Gln Lys Gln Ile Ser
                660                 665                 670
```

```
tac tca cca gga gta tgc agc ata gaa cat cag caa gag ata acc aaa       2064
Tyr Ser Pro Gly Val Cys Ser Ile Glu His Gln Gln Glu Ile Thr Lys
            675                 680                 685 cta aag act gat ttg gaa aag aaa agt atc ttt tat gaa gaa gaa tta       2112
Leu Lys Thr Asp Leu Glu Lys Lys Ser Ile Phe Tyr Glu Glu Glu Leu
        690                 695                 700 tct aaa aga gaa gga ata cat gca aat gaa ata aaa aat ctt aag aaa       2160
Ser Lys Arg Glu Gly Ile His Ala Asn Glu Ile Lys Asn Leu Lys Lys
705                 710                 715                 720 gaa ctg cat gat tca gaa ggt cag caa ctt gct ctc aac aaa gaa att       2208
Glu Leu His Asp Ser Glu Gly Gln Gln Leu Ala Leu Asn Lys Glu Ile
                725                 730                 735 atg att tta aaa gac aaa ttg gaa aaa acc aga aga gaa agt caa agt       2256
Met Ile Leu Lys Asp Lys Leu Glu Lys Thr Arg Arg Glu Ser Gln Ser
            740                 745                 750 gaa agg gag gaa ttt gaa agt gag ttc aaa caa caa tat gaa cga gaa       2304
Glu Arg Glu Glu Phe Glu Ser Glu Phe Lys Gln Gln Tyr Glu Arg Glu
        755                 760                 765 aaa gtg ttg tta act gaa gaa aat aaa aag ctg acg agt gaa ctt gat       2352
Lys Val Leu Leu Thr Glu Glu Asn Lys Lys Leu Thr Ser Glu Leu Asp
770                 775                 780 aag ctt act act ttg tat gag aac tta agt ata cac aac cag cag tta       2400
Lys Leu Thr Thr Leu Tyr Glu Asn Leu Ser Ile His Asn Gln Gln Leu
785                 790                 795                 800 gaa gaa gag gtt aaa gat cta gca gac aag aaa gaa tca gtt gca cat       2448
Glu Glu Glu Val Lys Asp Leu Ala Asp Lys Lys Glu Ser Val Ala His
            805                 810                 815 tgg gaa gcc caa atc aca gaa ata att cag tgg gtc agc gat gaa aag       2496
Trp Glu Ala Gln Ile Thr Glu Ile Ile Gln Trp Val Ser Asp Glu Lys
        820                 825                 830 gat gca cga ggg tat ctt cag gcc tta gct tct aaa atg act gaa gaa       2544
Asp Ala Arg Gly Tyr Leu Gln Ala Leu Ala Ser Lys Met Thr Glu Glu
                835                 840                 845 ttg gag gca tta aga aat tcc agc ttg ggt aca cga gca aca gat atg       2592
Leu Glu Ala Leu Arg Asn Ser Ser Leu Gly Thr Arg Ala Thr Asp Met
850                 855                 860 ccc tgg aaa atg cgt cgt ttt gcg aaa ctg gat atg tca gct aga ctg       2640
Pro Trp Lys Met Arg Arg Phe Ala Lys Leu Asp Met Ser Ala Arg Leu
865                 870                 875                 880 gag ttg cag tcg gct ctg gat gca gaa ata aga gcc aaa cag gcc atc       2688
Glu Leu Gln Ser Ala Leu Asp Ala Glu Ile Arg Ala Lys Gln Ala Ile
            885                 890                 895 caa gaa gag ttg aat aaa gtt aaa gca tct aat atc ata aca gaa tgt       2736
Gln Glu Glu Leu Asn Lys Val Lys Ala Ser Asn Ile Ile Thr Glu Cys
        900                 905                 910 aaa cta aaa gat tca gag aag aag aac ttg gaa cta ctc tca gaa atc       2784
Lys Leu Lys Asp Ser Glu Lys Lys Asn Leu Glu Leu Leu Ser Glu Ile
                915                 920                 925 gaa cag ctg ata aag gac act gaa gag ctt aga tct gaa aag ggt ata       2832
Glu Gln Leu Ile Lys Asp Thr Glu Glu Leu Arg Ser Glu Lys Gly Ile
930                 935                 940 gag cac caa gac tca cag cat tct ttc ttg gca ttt ttg aat acg cct       2880
Glu His Gln Asp Ser Gln His Ser Phe Leu Ala Phe Leu Asn Thr Pro
945                 950                 955                 960 acc gat gct ctg gat caa ttt gaa cgc tct cca tcc tgt act cca gct       2928
Thr Asp Ala Leu Asp Gln Phe Glu Arg Ser Pro Ser Cys Thr Pro Ala
            965                 970                 975 agc aaa ggc aga cgt act gta gac tcc act cca ctt tca gtt cac aca       2976
Ser Lys Gly Arg Arg Thr Val Asp Ser Thr Pro Leu Ser Val His Thr
        980                 985                 990
```

```
cca acc tta agg aaa aaa gga tgt cct ggt tca act ggc ttt cca cct      3024
Pro Thr Leu Arg Lys Lys Gly Cys Pro Gly Ser Thr Gly Phe Pro Pro
        995                 1000                1005 aag cgc aag act cac cag ttt ttt gta aaa tct ttt act act cct acc      3072
Lys Arg Lys Thr His Gln Phe Phe Val Lys Ser Phe Thr Thr Pro Thr
    1010                1015                1020 aag tgt cat cag tgt acc tcc ttg atg gtg ggt tta ata aga cag ggc      3120
Lys Cys His Gln Cys Thr Ser Leu Met Val Gly Leu Ile Arg Gln Gly
1025                1030                1035                1040 tgt tca tgt gaa gtg tgt gga ttc tca tgc cat ata act tgt gta aac      3168
Cys Ser Cys Glu Val Cys Gly Phe Ser Cys His Ile Thr Cys Val Asn
                1045                1050                1055 aaa gct cca acc act tgt cca gtt cct cct gaa cag aca aaa ggt ccc      3216
Lys Ala Pro Thr Thr Cys Pro Val Pro Pro Glu Gln Thr Lys Gly Pro
            1060                1065                1070 ctg ggt ata gat cct cag aaa gga ata gga aca gca tat gaa ggt cat      3264
Leu Gly Ile Asp Pro Gln Lys Gly Ile Gly Thr Ala Tyr Glu Gly His
        1075                1080                1085 gtc agg att cct aag cca gct gga gtg aag aaa ggg tgg cag aga gca      3312
Val Arg Ile Pro Lys Pro Ala Gly Val Lys Lys Gly Trp Gln Arg Ala
    1090                1095                1100 ctg gct ata gtg tgt gac ttc aaa ctc ttt ctg tac gat att gct gaa      3360
Leu Ala Ile Val Cys Asp Phe Lys Leu Phe Leu Tyr Asp Ile Ala Glu
1105                1110                1115                1120 gga aaa gca tct cag ccc agt gtt gtc att agt caa gtg att gac atg      3408
Gly Lys Ala Ser Gln Pro Ser Val Val Ile Ser Gln Val Ile Asp Met
                1125                1130                1135 agg gat gaa gaa ttt tct gtg agt tca gtc ttg gct tct gat gtt atc      3456
Arg Asp Glu Glu Phe Ser Val Ser Ser Val Leu Ala Ser Asp Val Ile
            1140                1145                1150 cat gca agt cgg aaa gat ata ccc tgt ata ttt agg gtc aca gct tcc      3504
His Ala Ser Arg Lys Asp Ile Pro Cys Ile Phe Arg Val Thr Ala Ser
        1155                1160                1165 cag ctc tca gca tct aat aac aaa tgt tca atc ctg atg cta gca gac      3552
Gln Leu Ser Ala Ser Asn Asn Lys Cys Ser Ile Leu Met Leu Ala Asp
    1170                1175                1180 act gag aat gag aag aat aag tgg gtg gga gtg ctg agt gaa ttg cac      3600
Thr Glu Asn Glu Lys Asn Lys Trp Val Gly Val Leu Ser Glu Leu His
1185                1190                1195                1200 aag att ttg aag aaa aac aaa ttc aga gac cgc tca gtc tat gtt ccc      3648
Lys Ile Leu Lys Lys Asn Lys Phe Arg Asp Arg Ser Val Tyr Val Pro
                1205                1210                1215 aaa gag gct tat gac agc act cta ccc ctc att aaa aca acc cag gca      3696
Lys Glu Ala Tyr Asp Ser Thr Leu Pro Leu Ile Lys Thr Thr Gln Ala
            1220                1225                1230 gcc gca atc ata gat cat gaa aga att gct ttg gga aac gaa gaa ggg      3744
Ala Ala Ile Ile Asp His Glu Arg Ile Ala Leu Gly Asn Glu Glu Gly
        1235                1240                1245 tta ttt gtt gta cat gtc acc aaa gat gaa att att aga gtt ggt gac      3792
Leu Phe Val Val His Val Thr Lys Asp Glu Ile Ile Arg Val Gly Asp
    1250                1255                1260 aat aag aag att cat cag att gaa ctc att cca aat gat cag ctt gtt      3840
Asn Lys Lys Ile His Gln Ile Glu Leu Ile Pro Asn Asp Gln Leu Val
1265                1270                1275                1280 gct gtg atc tca gga cga aat cgt cat gta cga ctt ttt cct atg tca      3888
Ala Val Ile Ser Gly Arg Asn Arg His Val Arg Leu Phe Pro Met Ser
                1285                1290                1295 gca ttg gat ggg cga gag acc gat ttt tac aag ctg tca gaa act aaa      3936
Ala Leu Asp Gly Arg Glu Thr Asp Phe Tyr Lys Leu Ser Glu Thr Lys
```

-continued

| | | | | | | | | | | | | | | | |
|---|---|---|---|---|---|---|---|---|---|---|---|---|---|---|---|
| | 1300 | | | | 1305 | | | | | 1310 | | | | | |
| ggg | tgt | caa | acc | gta | act | tct | gga | aag | gtg | cgc | cat | gga | gct | ctc | aca | 3984 |
| Gly | Cys | Gln | Thr | Val | Thr | Ser | Gly | Lys | Val | Arg | His | Gly | Ala | Leu | Thr | |
| | | 1315 | | | | | 1320 | | | | | 1325 | | | | |
| tgc | ctg | tgt | gtg | gct | atg | aaa | agg | cag | gtc | ctc | tgt | tat | gaa | cta | ttt | 4032 |
| Cys | Leu | Cys | Val | Ala | Met | Lys | Arg | Gln | Val | Leu | Cys | Tyr | Glu | Leu | Phe | |
| 1330 | | | | | 1335 | | | | | 1340 | | | | | | |
| cag | agc | aag | acc | cgt | cac | aga | aaa | ttt | aaa | gaa | att | caa | gtc | cca | tat | 4080 |
| Gln | Ser | Lys | Thr | Arg | His | Arg | Lys | Phe | Lys | Glu | Ile | Gln | Val | Pro | Tyr | |
| 1345 | | | | | 1350 | | | | | 1355 | | | | | 1360 | |
| aat | gtc | cag | tgg | atg | gca | atc | ttc | agt | gaa | caa | ctc | tgt | gtg | gga | ttc | 4128 |
| Asn | Val | Gln | Trp | Met | Ala | Ile | Phe | Ser | Glu | Gln | Leu | Cys | Val | Gly | Phe | |
| | | | 1365 | | | | | 1370 | | | | | 1375 | | | |
| cag | tca | gga | ttt | cta | aga | tac | ccc | ttg | aat | gga | gaa | gga | aat | cca | tac | 4176 |
| Gln | Ser | Gly | Phe | Leu | Arg | Tyr | Pro | Leu | Asn | Gly | Glu | Gly | Asn | Pro | Tyr | |
| | 1380 | | | | | 1385 | | | | | 1390 | | | | | |
| agt | atg | ctc | cat | tca | aat | gac | cat | aca | cta | tca | ttt | att | gca | cat | caa | 4224 |
| Ser | Met | Leu | His | Ser | Asn | Asp | His | Thr | Leu | Ser | Phe | Ile | Ala | His | Gln | |
| | | 1395 | | | | | 1400 | | | | | 1405 | | | | |
| cca | atg | gat | gct | atc | tgc | gca | gtt | gag | atc | tcc | agt | aaa | gaa | tat | ctg | 4272 |
| Pro | Met | Asp | Ala | Ile | Cys | Ala | Val | Glu | Ile | Ser | Ser | Lys | Glu | Tyr | Leu | |
| | 1410 | | | | | 1415 | | | | | 1420 | | | | | |
| ctg | tgt | ttt | aac | agc | att | ggg | ata | tac | act | gac | tgc | cag | ggc | cga | aga | 4320 |
| Leu | Cys | Phe | Asn | Ser | Ile | Gly | Ile | Tyr | Thr | Asp | Cys | Gln | Gly | Arg | Arg | |
| 1425 | | | | | 1430 | | | | | 1435 | | | | | 1440 | |
| tct | aga | caa | cag | gaa | ttg | atg | tgg | cca | gca | aat | cct | tcc | tct | tgt | tgt | 4368 |
| Ser | Arg | Gln | Gln | Glu | Leu | Met | Trp | Pro | Ala | Asn | Pro | Ser | Ser | Cys | Cys | |
| | | | | 1445 | | | | | 1450 | | | | | 1455 | | |
| tac | aat | gca | cca | tat | ctc | tcg | gtg | tac | agt | gaa | aat | gca | gtt | gat | atc | 4416 |
| Tyr | Asn | Ala | Pro | Tyr | Leu | Ser | Val | Tyr | Ser | Glu | Asn | Ala | Val | Asp | Ile | |
| | | | 1460 | | | | | 1465 | | | | | 1470 | | | |
| ttt | gat | gtg | aac | tcc | atg | gaa | tgg | att | cag | act | ctt | cct | ctc | aaa | aag | 4464 |
| Phe | Asp | Val | Asn | Ser | Met | Glu | Trp | Ile | Gln | Thr | Leu | Pro | Leu | Lys | Lys | |
| | | 1475 | | | | | 1480 | | | | | 1485 | | | | |
| gtt | cga | ccc | tta | aac | aat | gaa | gga | tca | tta | aat | ctt | tta | ggg | ttg | gag | 4512 |
| Val | Arg | Pro | Leu | Asn | Asn | Glu | Gly | Ser | Leu | Asn | Leu | Leu | Gly | Leu | Glu | |
| | 1490 | | | | | 1495 | | | | | 1500 | | | | | |
| acc | att | aga | tta | ata | tat | ttc | aaa | aat | aag | atg | gca | gaa | ggg | gac | gaa | 4560 |
| Thr | Ile | Arg | Leu | Ile | Tyr | Phe | Lys | Asn | Lys | Met | Ala | Glu | Gly | Asp | Glu | |
| 1505 | | | | | 1510 | | | | | 1515 | | | | | 1520 | |
| ctg | gta | gta | cct | gaa | aca | tca | gat | aat | agt | cgg | aaa | caa | atg | gtt | aga | 4608 |
| Leu | Val | Val | Pro | Glu | Thr | Ser | Asp | Asn | Ser | Arg | Lys | Gln | Met | Val | Arg | |
| | | | 1525 | | | | | 1530 | | | | | 1535 | | | |
| aac | att | aac | aat | aag | cgg | cgt | tat | tcc | ttc | aga | gtc | cca | gaa | gag | gaa | 4656 |
| Asn | Ile | Asn | Asn | Lys | Arg | Arg | Tyr | Ser | Phe | Arg | Val | Pro | Glu | Glu | Glu | |
| | | | 1540 | | | | | 1545 | | | | | 1550 | | | |
| agg | atg | cag | cag | agg | agg | gaa | atg | cta | cga | gat | cca | gaa | atg | aga | aat | 4704 |
| Arg | Met | Gln | Gln | Arg | Arg | Glu | Met | Leu | Arg | Asp | Pro | Glu | Met | Arg | Asn | |
| | | | 1555 | | | | | 1560 | | | | | 1565 | | | |
| aaa | tta | att | tct | aat | cca | act | aat | ttt | aat | cac | ata | gca | cac | atg | ggt | 4752 |
| Lys | Leu | Ile | Ser | Asn | Pro | Thr | Asn | Phe | Asn | His | Ile | Ala | His | Met | Gly | |
| | 1570 | | | | | 1575 | | | | | 1580 | | | | | |
| cct | gga | gat | gga | ata | cag | atc | ctg | aaa | gat | ctg | ccc | atg | aac | cct | cgg | 4800 |
| Pro | Gly | Asp | Gly | Ile | Gln | Ile | Leu | Lys | Asp | Leu | Pro | Met | Asn | Pro | Arg | |
| 1585 | | | | | 1590 | | | | | 1595 | | | | | 1600 | |
| cct | cag | gaa | agt | cgg | aca | gta | ttc | agt | ggc | tca | gtc | agt | att | cca | tct | 4848 |
| Pro | Gln | Glu | Ser | Arg | Thr | Val | Phe | Ser | Gly | Ser | Val | Ser | Ile | Pro | Ser | |
| | | | | 1605 | | | | | 1610 | | | | | 1615 | | |
| atc | acc | aaa | tcc | cgc | cct | gag | cca | ggc | cgc | tcc | atg | agt | gct | agc | agt | 4896 |

-continued

```
Ile Thr Lys Ser Arg Pro Glu Pro Gly Arg Ser Met Ser Ala Ser Ser
        1620                1625                1630 ggc ttg tca gca agg tca tcc gca cag aat ggc agc gca tta aag agg      4944
Gly Leu Ser Ala Arg Ser Ser Ala Gln Asn Gly Ser Ala Leu Lys Arg
        1635                1640                1645 gaa ttc tct gga gga agc tac agt gcc aag cgg cag ccc atg ccc tcc      4992
Glu Phe Ser Gly Gly Ser Tyr Ser Ala Lys Arg Gln Pro Met Pro Ser
        1650                1655                1660 ccg tca gag ggc tct ttg tcc tct gga ggc atg gac caa gga agt gat      5040
Pro Ser Glu Gly Ser Leu Ser Ser Gly Gly Met Asp Gln Gly Ser Asp
1665                1670                1675                1680 gcc cca gcg agg gac ttt gac gga gag gac tct gac tct ccg agg cat      5088
Ala Pro Ala Arg Asp Phe Asp Gly Glu Asp Ser Asp Ser Pro Arg His
                1685                1690                1695 tcc aca gct tcc aac agt tcc aac cta agc agc ccc cca agc cca gct      5136
Ser Thr Ala Ser Asn Ser Ser Asn Leu Ser Ser Pro Pro Ser Pro Ala
            1700                1705                1710 tca ccc cga aaa acc aag agc ctc tcc ctg gag agc act gac cgc ggg      5184
Ser Pro Arg Lys Thr Lys Ser Leu Ser Leu Glu Ser Thr Asp Arg Gly
        1715                1720                1725 agc tgg gac ccg                                                      5196
Ser Trp Asp Pro
    1730
```

<210> SEQ ID NO 2
<211> LENGTH: 1732
<212> TYPE: PRT
<213> ORGANISM: Homo sapiens

<400> SEQUENCE: 2

```
Met Ser Gly Glu Val Arg Leu Arg Gln Leu Glu Gln Phe Ile Leu Asp
1               5                   10                  15

Gly Pro Ala Gln Thr Asn Gly Gln Cys Phe Ser Val Glu Thr Leu Leu
            20                  25                  30

Asp Ile Leu Ile Cys Leu Tyr Asp Glu Cys Asn Asn Ser Pro Leu Arg
        35                  40                  45

Arg Glu Lys Asn Ile Leu Glu Tyr Leu Glu Trp Ala Lys Pro Phe Thr
    50                  55                  60

Ser Lys Val Lys Gln Met Arg Leu His Arg Glu Asp Phe Glu Ile Leu
65                  70                  75                  80

Lys Val Ile Gly Arg Gly Ala Phe Gly Glu Val Ala Val Val Lys Leu
                85                  90                  95

Lys Asn Ala Asp Lys Val Phe Ala Met Lys Ile Leu Asn Lys Trp Glu
            100                 105                 110

Met Leu Lys Arg Ala Glu Thr Ala Cys Phe Arg Glu Glu Arg Asp Val
        115                 120                 125

Leu Val Asn Gly Asp Asn Lys Trp Ile Thr Thr Leu His Tyr Ala Phe
    130                 135                 140

Gln Asp Asp Asn Asn Leu Tyr Leu Val Met Asp Tyr Val Gly Gly
145                 150                 155                 160

Asp Leu Leu Thr Leu Leu Ser Lys Phe Glu Asp Arg Leu Pro Glu Asp
                165                 170                 175

Met Ala Arg Phe Tyr Leu Ala Glu Met Val Ile Ala Ile Asp Ser Val
            180                 185                 190

His Gln Leu His Tyr Val His Arg Asp Ile Lys Pro Asp Asn Ile Leu
        195                 200                 205

Met Asp Met Asn Gly His Ile Arg Leu Ala Asp Phe Gly Ser Cys Leu
```

-continued

```
                210                 215                 220
Lys Leu Met Glu Asp Gly Thr Val Gln Ser Ser Val Ala Val Gly Thr
225                 230                 235                 240

Pro Asp Tyr Ile Ser Pro Glu Ile Leu Gln Ala Met Glu Asp Gly Lys
                245                 250                 255

Gly Arg Tyr Gly Pro Glu Cys Asp Trp Trp Ser Leu Gly Val Cys Met
                260                 265                 270

Tyr Glu Met Leu Tyr Gly Glu Thr Pro Phe Tyr Ala Glu Ser Leu Val
            275                 280                 285

Glu Thr Tyr Gly Lys Ile Met Asn His Lys Glu Arg Phe Gln Phe Pro
        290                 295                 300

Ala Gln Val Thr Asp Val Ser Glu Asn Ala Lys Asp Leu Ile Arg Arg
305                 310                 315                 320

Leu Ile Cys Ser Arg Glu His Arg Leu Gly Gln Asn Gly Ile Glu Asp
                325                 330                 335

Phe Lys Lys His Pro Phe Phe Ser Gly Ile Asp Trp Asp Asn Ile Arg
                340                 345                 350

Asn Cys Glu Ala Pro Tyr Ile Pro Glu Val Ser Ser Pro Thr Asp Thr
            355                 360                 365

Ser Asn Phe Asp Val Asp Asp Cys Leu Lys Asn Ser Glu Thr Met
        370                 375                 380

Pro Pro Pro Thr His Thr Ala Phe Ser Gly His His Leu Pro Phe Val
385                 390                 395                 400

Gly Phe Thr Tyr Thr Ser Ser Cys Val Leu Ser Asp Arg Ser Cys Leu
                405                 410                 415

Arg Val Thr Ala Gly Pro Thr Ser Leu Asp Leu Asp Val Asn Val Gln
                420                 425                 430

Arg Thr Leu Asp Asn Asn Leu Ala Thr Glu Ala Tyr Glu Arg Arg Ile
            435                 440                 445

Lys Arg Leu Glu Gln Glu Lys Leu Glu Leu Ser Arg Lys Leu Gln Glu
        450                 455                 460

Ser Thr Gln Thr Val Gln Ala Leu Gln Tyr Ser Thr Val Asp Gly Pro
465                 470                 475                 480

Leu Thr Ala Ser Lys Asp Leu Glu Ile Lys Asn Leu Lys Glu Glu Ile
                485                 490                 495

Glu Lys Leu Arg Lys Gln Val Thr Glu Ser Ser His Leu Glu Gln Gln
                500                 505                 510

Leu Glu Glu Ala Asn Ala Val Arg Gln Glu Leu Asp Asp Ala Phe Arg
            515                 520                 525

Gln Ile Lys Ala Tyr Glu Lys Gln Ile Lys Thr Leu Gln Gln Glu Arg
        530                 535                 540

Glu Asp Leu Asn Lys Glu Leu Val Gln Ala Ser Glu Arg Leu Lys Asn
545                 550                 555                 560

Gln Ser Lys Glu Leu Lys Asp Ala His Cys Gln Arg Lys Leu Ala Met
                565                 570                 575

Gln Glu Phe Met Glu Ile Asn Glu Arg Leu Thr Glu Leu His Thr Gln
            580                 585                 590

Lys Gln Lys Leu Ala Arg His Val Arg Asp Lys Glu Glu Val Asp
        595                 600                 605

Leu Val Met Gln Lys Val Glu Ser Leu Arg Gln Glu Leu Arg Arg Thr
610                 615                 620

Glu Arg Ala Lys Lys Glu Val Ser Ile His Thr Glu Ala Leu Ala Ala
625                 630                 635                 640
```

-continued

```
Glu Ala Ser Lys Asp Arg Lys Leu Arg Glu Gln Ser Glu His Tyr Ser
                645                 650                 655
Lys Gln Leu Glu Asn Glu Leu Glu Gly Leu Lys Gln Lys Gln Ile Ser
            660                 665                 670
Tyr Ser Pro Gly Val Cys Ser Ile Glu His Gln Gln Glu Ile Thr Lys
        675                 680                 685
Leu Lys Thr Asp Leu Glu Lys Lys Ser Ile Phe Tyr Glu Glu Glu Leu
    690                 695                 700
Ser Lys Arg Glu Gly Ile His Ala Asn Glu Ile Lys Asn Leu Lys Lys
705                 710                 715                 720
Glu Leu His Asp Ser Glu Gly Gln Gln Leu Ala Leu Asn Lys Glu Ile
                725                 730                 735
Met Ile Leu Lys Asp Lys Leu Glu Lys Thr Arg Arg Glu Ser Gln Ser
            740                 745                 750
Glu Arg Glu Glu Phe Glu Ser Glu Phe Lys Gln Gln Tyr Glu Arg Glu
        755                 760                 765
Lys Val Leu Leu Thr Glu Glu Asn Lys Lys Leu Thr Ser Glu Leu Asp
    770                 775                 780
Lys Leu Thr Thr Leu Tyr Glu Asn Leu Ser Ile His Asn Gln Gln Leu
785                 790                 795                 800
Glu Glu Glu Val Lys Asp Leu Ala Asp Lys Lys Glu Ser Val Ala His
                805                 810                 815
Trp Glu Ala Gln Ile Thr Glu Ile Ile Gln Trp Val Ser Asp Glu Lys
            820                 825                 830
Asp Ala Arg Gly Tyr Leu Gln Ala Leu Ala Ser Lys Met Thr Glu Glu
        835                 840                 845
Leu Glu Ala Leu Arg Asn Ser Ser Leu Gly Thr Arg Ala Thr Asp Met
    850                 855                 860
Pro Trp Lys Met Arg Arg Phe Ala Lys Leu Asp Met Ser Ala Arg Leu
865                 870                 875                 880
Glu Leu Gln Ser Ala Leu Asp Ala Glu Ile Arg Ala Lys Gln Ala Ile
                885                 890                 895
Gln Glu Glu Leu Asn Lys Val Lys Ala Ser Asn Ile Ile Thr Glu Cys
            900                 905                 910
Lys Leu Lys Asp Ser Glu Lys Lys Asn Leu Glu Leu Leu Ser Glu Ile
        915                 920                 925
Glu Gln Leu Ile Lys Asp Thr Glu Glu Leu Arg Ser Glu Lys Gly Ile
    930                 935                 940
Glu His Gln Asp Ser Gln His Ser Phe Leu Ala Phe Leu Asn Thr Pro
945                 950                 955                 960
Thr Asp Ala Leu Asp Gln Phe Glu Arg Ser Pro Ser Cys Thr Pro Ala
                965                 970                 975
Ser Lys Gly Arg Arg Thr Val Asp Ser Thr Pro Leu Ser Val His Thr
            980                 985                 990
Pro Thr Leu Arg Lys Lys Gly Cys Pro Gly Ser Thr Gly Phe Pro Pro
        995                 1000                1005
Lys Arg Lys Thr His Gln Phe Phe Val Lys Ser Phe Thr Thr Pro Thr
    1010                1015                1020
Lys Cys His Gln Cys Thr Ser Leu Met Val Gly Leu Ile Arg Gln Gly
1025                1030                1035                1040
Cys Ser Cys Glu Val Cys Gly Phe Ser Cys His Ile Thr Cys Val Asn
                1045                1050                1055
```

-continued

Lys Ala Pro Thr Thr Cys Pro Val Pro Pro Glu Gln Thr Lys Gly Pro
              1060                1065                1070

Leu Gly Ile Asp Pro Gln Lys Gly Ile Gly Thr Ala Tyr Glu Gly His
         1075                1080                1085

Val Arg Ile Pro Lys Pro Ala Gly Val Lys Lys Gly Trp Gln Arg Ala
     1090                1095                1100

Leu Ala Ile Val Cys Asp Phe Lys Leu Phe Leu Tyr Asp Ile Ala Glu
1105                1110                1115                1120

Gly Lys Ala Ser Gln Pro Ser Val Val Ile Ser Gln Val Ile Asp Met
             1125                1130                1135

Arg Asp Glu Glu Phe Ser Val Ser Ser Val Leu Ala Ser Asp Val Ile
                 1140                1145                1150

His Ala Ser Arg Lys Asp Ile Pro Cys Ile Phe Arg Val Thr Ala Ser
             1155                1160                1165

Gln Leu Ser Ala Ser Asn Asn Lys Cys Ser Ile Leu Met Leu Ala Asp
     1170                1175                1180

Thr Glu Asn Glu Lys Asn Lys Trp Val Gly Val Leu Ser Glu Leu His
1185                1190                1195                1200

Lys Ile Leu Lys Lys Asn Lys Phe Arg Asp Arg Ser Val Tyr Val Pro
             1205                1210                1215

Lys Glu Ala Tyr Asp Ser Thr Leu Pro Leu Ile Lys Thr Thr Gln Ala
             1220                1225                1230

Ala Ala Ile Ile Asp His Glu Arg Ile Ala Leu Gly Asn Glu Glu Gly
             1235                1240                1245

Leu Phe Val Val His Val Thr Lys Asp Glu Ile Ile Arg Val Gly Asp
     1250                1255                1260

Asn Lys Lys Ile His Gln Ile Glu Leu Ile Pro Asn Asp Gln Leu Val
1265                1270                1275                1280

Ala Val Ile Ser Gly Arg Asn Arg His Val Arg Leu Phe Pro Met Ser
                 1285                1290                1295

Ala Leu Asp Gly Arg Glu Thr Asp Phe Tyr Lys Leu Ser Glu Thr Lys
             1300                1305                1310

Gly Cys Gln Thr Val Thr Ser Gly Lys Val Arg His Gly Ala Leu Thr
             1315                1320                1325

Cys Leu Cys Val Ala Met Lys Arg Gln Val Leu Cys Tyr Glu Leu Phe
     1330                1335                1340

Gln Ser Lys Thr Arg His Arg Lys Phe Lys Glu Ile Gln Val Pro Tyr
1345                1350                1355                1360

Asn Val Gln Trp Met Ala Ile Phe Ser Glu Gln Leu Cys Val Gly Phe
             1365                1370                1375

Gln Ser Gly Phe Leu Arg Tyr Pro Leu Asn Gly Glu Gly Asn Pro Tyr
             1380                1385                1390

Ser Met Leu His Ser Asn Asp His Thr Leu Ser Phe Ile Ala His Gln
     1395                1400                1405

Pro Met Asp Ala Ile Cys Ala Val Glu Ile Ser Ser Lys Glu Tyr Leu
     1410                1415                1420

Leu Cys Phe Asn Ser Ile Gly Ile Tyr Thr Asp Cys Gln Gly Arg Arg
1425                1430                1435                1440

Ser Arg Gln Gln Glu Leu Met Trp Pro Ala Asn Pro Ser Ser Cys Cys
                 1445                1450                1455

Tyr Asn Ala Pro Tyr Leu Ser Val Tyr Ser Glu Asn Ala Val Asp Ile
             1460                1465                1470

Phe Asp Val Asn Ser Met Glu Trp Ile Gln Thr Leu Pro Leu Lys Lys

-continued

```
                1475                1480                1485
Val Arg Pro Leu Asn Asn Glu Gly Ser Leu Asn Leu Leu Gly Leu Glu
    1490                1495                1500

Thr Ile Arg Leu Ile Tyr Phe Lys Asn Lys Met Ala Glu Gly Asp Glu
1505                1510                1515                1520

Leu Val Val Pro Glu Thr Ser Asp Asn Ser Arg Lys Gln Met Val Arg
                1525                1530                1535

Asn Ile Asn Asn Lys Arg Arg Tyr Ser Phe Arg Val Pro Glu Glu Glu
            1540                1545                1550

Arg Met Gln Gln Arg Arg Glu Met Leu Arg Asp Pro Glu Met Arg Asn
        1555                1560                1565

Lys Leu Ile Ser Asn Pro Thr Asn Phe Asn His Ile Ala His Met Gly
    1570                1575                1580

Pro Gly Asp Gly Ile Gln Ile Leu Lys Asp Leu Pro Met Asn Pro Arg
1585                1590                1595                1600

Pro Gln Glu Ser Arg Thr Val Phe Ser Gly Ser Val Ser Ile Pro Ser
                1605                1610                1615

Ile Thr Lys Ser Arg Pro Glu Pro Gly Arg Ser Met Ser Ala Ser Ser
            1620                1625                1630

Gly Leu Ser Ala Arg Ser Ser Ala Gln Asn Gly Ser Ala Leu Lys Arg
        1635                1640                1645

Glu Phe Ser Gly Gly Ser Tyr Ser Ala Lys Arg Gln Pro Met Pro Ser
    1650                1655                1660

Pro Ser Glu Gly Ser Leu Ser Ser Gly Gly Met Asp Gln Gly Ser Asp
1665                1670                1675                1680

Ala Pro Ala Arg Asp Phe Asp Gly Glu Asp Ser Asp Ser Pro Arg His
                1685                1690                1695

Ser Thr Ala Ser Asn Ser Ser Asn Leu Ser Ser Pro Ser Pro Ala
            1700                1705                1710

Ser Pro Arg Lys Thr Lys Ser Leu Ser Leu Glu Ser Thr Asp Arg Gly
        1715                1720                1725

Ser Trp Asp Pro
    1730
```

<210> SEQ ID NO 3
<211> LENGTH: 1732
<212> TYPE: PRT
<213> ORGANISM: Rattus norvegicus
<300> PUBLICATION INFORMATION:
<308> DATABASE ACCESSION NUMBER: EMBL/AF021935
<309> DATABASE ENTRY DATE: 2000-08-30

<400> SEQUENCE: 3

```
Met Ser Gly Glu Val Arg Leu Arg Gln Leu Glu Gln Phe Ile Leu Asp
1               5                   10                  15

Gly Pro Ala Gln Thr Asn Gly Gln Cys Phe Ser Val Glu Thr Leu Leu
            20                  25                  30

Asp Ile Leu Ile Cys Leu Tyr Asp Glu Cys Asn Asn Ser Pro Leu Arg
        35                  40                  45

Arg Glu Lys Asn Ile Leu Glu Tyr Leu Glu Trp Ala Lys Pro Phe Thr
    50                  55                  60

Ser Lys Val Lys Gln Met Arg Leu His Arg Gly Asp Phe Glu Ile Leu
65                  70                  75                  80

Lys Val Ile Gly Arg Gly Ala Phe Gly Glu Val Ala Val Val Lys Leu
                85                  90                  95
```

-continued

```
Lys Asn Ala Asp Lys Val Phe Ala Met Lys Ile Leu Asn Lys Trp Glu
            100                 105                 110

Met Leu Lys Arg Ala Glu Thr Ala Cys Phe Arg Glu Glu Arg Asp Val
        115                 120                 125

Leu Val Asn Gly Asp Ser Lys Trp Ile Thr Thr Leu His Tyr Ala Phe
    130                 135                 140

Gln Asp Asp Asn Asn Leu Tyr Leu Val Met Asp Tyr Tyr Val Gly Gly
145                 150                 155                 160

Asp Leu Leu Thr Leu Leu Ser Lys Phe Glu Asp Arg Leu Pro Glu Glu
                165                 170                 175

Met Ala Arg Phe Tyr Leu Ala Glu Met Val Ile Ala Ile Asp Ser Val
            180                 185                 190

His Gln Leu His Tyr Val His Arg Asp Ile Lys Pro Asp Asn Ile Leu
        195                 200                 205

Met Asp Met Asn Gly His Ile Arg Leu Ala Asp Phe Gly Ser Cys Leu
    210                 215                 220

Lys Leu Met Glu Asp Gly Thr Val Gln Ser Ser Val Ala Val Gly Thr
225                 230                 235                 240

Pro Asp Tyr Ile Ser Pro Glu Ile Leu Gln Ala Met Glu Asp Gly Lys
                245                 250                 255

Gly Arg Tyr Gly Pro Glu Cys Asp Trp Trp Ser Leu Gly Val Cys Met
            260                 265                 270

Tyr Glu Met Leu Tyr Gly Glu Thr Pro Phe Tyr Ala Glu Ser Leu Val
        275                 280                 285

Glu Thr Tyr Gly Lys Ile Met Asn His Lys Glu Arg Phe Gln Phe Pro
    290                 295                 300

Thr Gln Val Thr Asp Val Ser Glu Asn Ala Lys Asp Leu Ile Arg Arg
305                 310                 315                 320

Leu Ile Cys Ser Arg Glu His Arg Leu Gly Gln Asn Gly Ile Glu Asp
                325                 330                 335

Phe Lys Lys His Pro Phe Phe Ser Gly Ile Asp Trp Asp Asn Ile Arg
            340                 345                 350

Asn Cys Glu Ala Pro Tyr Ile Pro Glu Val Ser Ser Pro Thr Asp Thr
        355                 360                 365

Ser Asn Phe Asp Val Asp Asp Asp Cys Leu Lys Asn Ser Glu Thr Met
    370                 375                 380

Pro Pro Pro Thr His Thr Ala Phe Ser Gly His His Leu Pro Phe Val
385                 390                 395                 400

Gly Phe Thr Tyr Thr Ser Ser Cys Val Leu Ser Asp Arg Ser Cys Leu
                405                 410                 415

Arg Val Thr Ala Gly Pro Thr Ser Leu Asp Leu Asp Val Asn Val Gln
            420                 425                 430

Arg Thr Leu Asp Asn Asn Leu Ala Thr Glu Ala Tyr Glu Arg Arg Ile
        435                 440                 445

Lys Arg Leu Glu Gln Glu Lys Leu Glu Leu Thr Arg Lys Leu Gln Glu
    450                 455                 460

Ser Thr Gln Thr Val Gln Ala Leu Gln Tyr Ser Thr Val Asp Gly Pro
465                 470                 475                 480

Leu Thr Ala Ser Lys Asp Leu Glu Ile Lys Ser Leu Lys Glu Glu Ile
                485                 490                 495

Glu Lys Leu Arg Lys Gln Val Ala Glu Val Asn His Leu Glu Gln Gln
            500                 505                 510

Leu Glu Glu Ala Asn Ser Val Arg Arg Glu Leu Asp Asp Ala Phe Arg
```

-continued

```
              515                 520                 525
Gln Ile Lys Ala Phe Glu Lys Gln Ile Lys Thr Leu Gln Gln Glu Arg
        530                 535                 540
Glu Glu Leu Asn Lys Glu Leu Val Gln Ala Ser Glu Arg Leu Lys Asn
545                 550                 555                 560
Gln Ser Lys Glu Leu Lys Asp Ala His Cys Gln Arg Lys Leu Ala Met
                565                 570                 575
Gln Glu Phe Met Glu Ile Asn Glu Arg Leu Thr Glu Leu His Thr Gln
                580                 585                 590
Lys Gln Lys Leu Ala Arg His Val Arg Asp Lys Glu Glu Val Asp
        595                 600                 605
Leu Val Met Gln Lys Ala Glu Ser Leu Arg Gln Glu Leu Arg Arg Ala
        610                 615                 620
Glu Arg Ala Lys Lys Glu Leu Glu Val His Thr Glu Ala Leu Ile Ala
625                 630                 635                 640
Glu Ala Ser Lys Asp Arg Lys Leu Arg Glu Gln Ser Arg His Tyr Ser
                645                 650                 655
Lys Gln Leu Glu Asn Glu Leu Glu Gly Leu Lys Gln Lys Gln Ile Ser
                660                 665                 670
Tyr Ser Pro Gly Ile Cys Ser Ile Glu His Gln Gln Glu Ile Thr Lys
        675                 680                 685
Leu Lys Thr Asp Leu Glu Lys Lys Ser Ile Phe Tyr Glu Glu Ile
        690                 695                 700
Ser Lys Arg Glu Gly Ile His Ala Ser Glu Ile Lys Asn Leu Lys Lys
705                 710                 715                 720
Glu Leu His Asp Ser Glu Gly Gln Gln Leu Ala Leu Asn Lys Glu Ile
                725                 730                 735
Met Val Leu Lys Asp Lys Leu Glu Lys Thr Arg Arg Glu Ser Gln Ser
                740                 745                 750
Glu Arg Glu Glu Phe Glu Asn Glu Phe Lys Gln Gln Tyr Glu Arg Glu
        755                 760                 765
Lys Val Leu Leu Thr Glu Glu Asn Lys Lys Leu Thr Ser Glu Leu Asp
770                 775                 780
Lys Leu Thr Ser Leu Tyr Glu Ser Leu Ser Leu Arg Asn Gln His Leu
785                 790                 795                 800
Glu Glu Glu Val Lys Asp Leu Ala Asp Lys Lys Glu Ser Val Ala His
                805                 810                 815
Trp Glu Ala Gln Ile Thr Glu Ile Ile Gln Trp Val Ser Asp Glu Lys
                820                 825                 830
Asp Ala Arg Gly Tyr Leu Gln Ala Leu Ala Ser Lys Met Thr Glu Glu
        835                 840                 845
Leu Glu Ala Leu Arg Asn Ser Ser Leu Gly Thr Arg Ala Thr Asp Met
        850                 855                 860
Pro Trp Lys Met Arg Arg Phe Ala Lys Leu Asp Met Ser Ala Arg Leu
865                 870                 875                 880
Glu Leu Gln Ser Ala Leu Asp Ala Glu Ile Arg Ala Lys Gln Ala Ile
                885                 890                 895
Gln Glu Glu Leu Asn Lys Val Lys Ala Ser Asn Ile Ile Thr Glu Cys
                900                 905                 910
Lys Leu Lys Asp Ser Glu Lys Lys Asn Leu Glu Leu Ser Glu Ile
                915                 920                 925
Glu Gln Leu Ile Lys Asp Thr Glu Glu Leu Arg Ser Glu Lys Gly Val
        930                 935                 940
```

-continued

Glu His Arg Asp Ser Gln His Ser Phe Leu Ala Phe Leu Asn Thr Pro
945                 950                 955                 960

Thr Asp Ala Leu Asp Gln Phe Glu Arg Ser Pro Ser Cys Thr Pro Ala
            965                 970                 975

Gly Lys Gly Arg Arg Ile Ala Asp Ser Ala Pro Leu Pro Val His Thr
        980                 985                 990

Pro Thr Leu Arg Lys Lys Gly Cys Pro Ala Ser Ala Gly Phe Pro Pro
    995                 1000                1005

Lys Arg Lys Thr His Gln Phe Phe Val Lys Ser Phe Thr Ala Pro Thr
1010                1015                1020

Lys Cys His Gln Cys Thr Ser Leu Met Val Gly Leu Ile Arg Gln Gly
1025                1030                1035                1040

Cys Ser Cys Glu Val Cys Gly Phe Ser Cys His Ile Thr Cys Val Asn
                1045                1050                1055

Lys Ala Pro Thr Thr Cys Pro Val Pro Pro Glu Gln Thr Lys Gly Pro
                1060                1065                1070

Leu Gly Ile Asp Pro Gln Lys Gly Val Gly Thr Ala Tyr Glu Gly His
            1075                1080                1085

Val Arg Ile Pro Lys Pro Ala Gly Val Lys Lys Gly Trp Gln Arg Ala
    1090                1095                1100

Leu Ala Val Val Cys Asp Phe Lys Leu Phe Leu Tyr Asp Ile Ala Glu
1105                1110                1115                1120

Gly Lys Ala Ser Gln Pro Ser Ser Val Ile Ser Gln Val Ile Asp Met
                1125                1130                1135

Arg Asp Glu Glu Phe Ser Val Ser Val Leu Ala Ser Asp Val Ile
            1140                1145                1150

His Ala Ser Arg Lys Asp Ile Pro Cys Ile Phe Arg Val Thr Ala Ser
            1155                1160                1165

Gln Leu Ser Ala Pro Ser Asp Lys Cys Ser Ile Leu Met Leu Ala Asp
    1170                1175                1180

Ser Glu Thr Glu Arg Ser Lys Trp Val Gly Val Leu Ser Glu Leu His
1185                1190                1195                1200

Lys Val Leu Lys Lys Asn Lys Phe Arg Asp Arg Ser Val Tyr Val Pro
                1205                1210                1215

Lys Glu Ala Tyr Asp Ser Thr Leu Pro Leu Ile Lys Thr Thr Gln Ala
            1220                1225                1230

Ala Ala Ile Ile Asp His Glu Arg Val Ala Leu Gly Asn Glu Glu Gly
        1235                1240                1245

Leu Phe Val Val His Val Thr Lys Asp Glu Ile Ile Arg Val Gly Asp
    1250                1255                1260

Asn Lys Lys Ile His Gln Ile Glu Leu Ile Pro Ser Asp Gln Leu Val
1265                1270                1275                1280

Ala Val Ile Ser Gly Arg Asn Arg His Val Arg Leu Phe Pro Met Ser
                1285                1290                1295

Ala Leu Asp Gly Arg Glu Thr Asp Phe Tyr Lys Leu Ala Glu Thr Lys
            1300                1305                1310

Gly Cys Gln Thr Ile Ala Ala Gly Lys Val Arg His Gly Ala Leu Ser
        1315                1320                1325

Cys Leu Cys Val Ala Met Lys Arg Gln Val Leu Cys Tyr Glu Leu Phe
    1330                1335                1340

Gln Ser Lys Thr Arg His Arg Lys Phe Lys Glu Ile Gln Val Pro Cys
1345                1350                1355                1360

-continued

Asn Val Gln Trp Met Ala Ile Phe Ser Glu His Leu Cys Val Gly Phe
              1365                1370                1375
Gln Ser Gly Phe Leu Arg Tyr Pro Leu Asn Gly Glu Gly Ser Pro Cys
        1380                1385                1390
Asn Met Leu His Ser Asn Asp His Thr Leu Ala Phe Ile Thr His Gln
    1395                1400                1405
Pro Met Asp Ala Ile Cys Ala Val Glu Ile Ser Asn Lys Glu Tyr Leu
1410                1415                1420
Leu Cys Phe Ser Ser Ile Gly Ile Tyr Thr Asp Cys Gln Gly Arg Arg
1425                1430                1435                1440
Ser Arg Gln Gln Glu Leu Met Trp Pro Ala Asn Pro Ser Ser Cys Cys
                1445                1450                1455
Tyr Asn Ala Pro Tyr Leu Ser Ile Tyr Ser Glu Asn Ala Val Asp Ile
            1460                1465                1470
Phe Asp Val Asn Ser Met Glu Trp Ile Gln Thr Leu Pro Leu Lys Lys
        1475                1480                1485
Val Arg Pro Leu Asn Thr Glu Gly Ser Leu Asn Leu Leu Gly Leu Glu
    1490                1495                1500
Thr Ile Arg Leu Ile Tyr Phe Lys Asn Lys Met Ala Glu Gly Asp Glu
1505                1510                1515                1520
Leu Val Val Pro Glu Thr Ser Asp Asn Ser Arg Lys Gln Met Val Arg
                1525                1530                1535
Asn Ile Asn Asn Lys Arg Arg Tyr Ser Phe Arg Val Pro Glu Glu Glu
            1540                1545                1550
Arg Met Gln Gln Arg Arg Glu Met Leu Arg Asp Pro Glu Met Arg Asn
        1555                1560                1565
Lys Leu Ile Ser Asn Pro Thr Asn Phe Asn His Ile Ala His Met Gly
    1570                1575                1580
Pro Gly Asp Gly Ile Gln Ile Leu Lys Asp Leu Pro Met Asn Pro Arg
1585                1590                1595                1600
Pro Gln Glu Ser Arg Thr Val Phe Ser Gly Ser Val Ser Ile Pro Ser
                1605                1610                1615
Ile Thr Lys Ser Arg Pro Glu Pro Gly Arg Ser Met Ser Ala Ser Ser
            1620                1625                1630
Gly Leu Ser Ala Arg Ser Ser Ala Gln Asn Gly Ser Ala Leu Lys Arg
        1635                1640                1645
Glu Phe Ser Gly Gly Ser Tyr Asn Thr Lys Arg Gln Pro Met Pro Ser
    1650                1655                1660
Pro Ser Glu Gly Ser Leu Ser Gly Gly Val Asp Gln Gly Ser Asp
1665                1670                1675                1680
Ala Pro Val Arg Asp Tyr Asp Gly Glu Asp Ser Asp Ser Pro Arg His
                1685                1690                1695
Ser Thr Ala Ser Asn Ser Ser Asn Leu Ser Ser Pro Ser Pro Val
            1700                1705                1710
Ser Pro Arg Lys Thr Lys Ser Leu Ser Leu Glu Ser Thr Asp Arg Gly
        1715                1720                1725
Ser Trp Asp Pro
    1730

<210> SEQ ID NO 4
<211> LENGTH: 710
<212> TYPE: DNA
<213> ORGANISM: Homo sapiens

<400> SEQUENCE: 4

```
gggcccgctc cgaccaatgg gcagtgcttc agtgtggaga cattactgga tatactcatc        60
tgcctttatg atgaatgcaa taattctcca ttgagaagag agaagaacat tctcgaatac       120
ctagaatggg ctaaaccatt tacttctaaa gtgaaacaaa tgcgattaca tagagaagac       180
tttgaaatat taaaggtgat tggtcgaggg gcttttgggg aggttgctgt agtaaaacta       240
aaaaatgcag ataaagtgtt tgccatgaaa atattgaata aatgggaaat gctgaaaaga       300
gctgagacag catgttttcg tgaagaaagg gatgtattag tgaatggaga caataaatgg       360
attacaacct tgcactatgc tttccaggat gacaataact tatacctggt tatggattat       420
tatgttggtg gggatttgct tactctactc agcaaatttg aagatagatt gcctgaagat       480
atggctagat tttacttggc tgagatggtg atagcaattg actcagttca tcagctacat       540
tattgtacac agagacatta aacctgacaa tatactgatg gatatgaatg acatattcg        600 gttagcagat ttggttcttg tctgaagctg atggaagatg aacggttca gtcctcagtg        660 gctgtaggaa ctccagatta tatctctcct gaaatccttc aagccatgga                  710

<210> SEQ ID NO 5
<211> LENGTH: 891
<212> TYPE: DNA
<213> ORGANISM: Homo sapiens
<220> FEATURE:
<221> NAME/KEY: misc_feature
<222> LOCATION: (1)...(891)
<223> OTHER INFORMATION: n = A,T,C or G

<400> SEQUENCE: 5
ggaagaagag gtggacctgg tgatgcaaaa agttgaaagc ttaaggcaag aactgcgcag        60
aacagaaaga gccaaaaaag agctggaagt tcatacagaa gctctagctg ctgaagcatc       120
taaagacagg aagctacgtg aacagagtga gcactattct aagcaactgg aaaatgaatt       180
ggagggactg aagcaaaaac aaattagtta ctcaccagga gtatgcagca tagaacatca       240
gcaagagata accaaactaa agactgattt ggaaaagaaa agtatctttt atgaagaaga       300
attatctaaa agagaaggaa tacatgcaaa tgaaataaaa atcttaaga aagaactgca        360 tgattcagaa ggtcagcaac ttgctctcaa caaagaaatt atgattttaa aagacaaatt       420
ggaaaaaacc agaagagaaa gtcaaagtga aaggaaggaa tttgaaagtg agttcaaaca       480
acaatatgaa cgagaaaaag tgttgttaac tgaagaaaat aaaaagctga cgagtgaact       540
tgataagctt actactttgt atgagaactt aagtatacac aaccagcagt tagaagaaga       600
ggttaaagat ctagncagac aagaaagaat cagtgtgcac atngggaagc caaatcacag       660
aaataattca gtgggtcagc gatgaaaagg atgcagcgag ggtatcttca gggccttagt       720
tctaaaatga ctgaagaatt tggggcctta gaaattcagg ttgggtaaac gagcaagata       780
tgccctggaa aatgggtggt tggaatggtt gtcagtaaag ggattgggg ttgggtggga       840 aatagagcaa ggctccaaag agggataagg aagttttta gagggaaag g                  891

<210> SEQ ID NO 6
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 6
```

| | |
|---|---|
| tatttctaaa tttttgcttg ctgttagtgg accatcaaca gttgaatact gcagagcttg | 60 |
| gacagtctgt gttgactctt gaagtttct actgagttca agtttttctt gctcaaggcg | 120 |
| cttaattctt ctttcataag cttcagttgc taagttgttg tctagagtcc tctgaacatt | 180 |
| aacatcaaga tccagtgagg tgggaccagc cgtaactctt aaacagctcc gatcagaaag | 240 |
| tacacagcta ctagtatatg taaaaccaac aaatggcaga tggtggccag aaaatgcagt | 300 |
| atgtgttggt gggggcatcg tttcagaatt ttttaaacaa tcatcatcta catcaaaatt | 360 |
| cgatgtatct gttgggctac taacttctgg aatataaggt gcttcacagt tccgaatatt | 420 |
| atcccaatca attccactga aaatggtg tttcttaaag tcttctattc cattttgacc | 480 |
| aagtcgatgt tctctgctac aaatgagcct tcgaataaga tccttagcat tttcagacac | 540 |
| atcagtcact gggctggaa actgaaacct ctctttgtgg ttcatgattn ttncgtatgt | 600 |
| ctccaccagc gattctgcat aaaa | 624 |

<210> SEQ ID NO 7
<211> LENGTH: 942
<212> TYPE: DNA
<213> ORGANISM: Homo sapiens

<400> SEQUENCE: 7

| | |
|---|---|
| cctgaaacat cagataatag tcggaaacaa atggttagaa acattaacaa taagcggcgt | 60 |
| tattccttca gagtcccaga agaggaaagg atgcagcaga ggagggaaat gctacgagat | 120 |
| ccagaaatga gaaataaatt aatttctaat ccaactaatt ttaatcacat agcacacatg | 180 |
| ggtcctggag atgaataca gatcctgaaa gatctgccca tgaaccctcg gcctcaggaa | 240 |
| agtcggacag tattcagtgg ctcagtcagt attccatcta tcaccaaatc ccgccctgag | 300 |
| ccaggccgct ccatgagtgc tagcagtggc ttgtcagcaa ggtcatccgc acagaatggc | 360 |
| agcgcattaa agagggaatt ctctggagga agctacagtg ccaagcggca gcccatgccc | 420 |
| tcccccgtcag agggctcttt gtcctccgga ggcatggacc aaggaagtga tgccccagcg | 480 |
| agggactttg acggagagga ctctgactct ccgaggcatt ccacagcttc caacagttcc | 540 |
| aacctaagca gcccccaagc ccagtttcac cccgaaaaac caagagctct ccctggagag | 600 |
| cactgaccgc gggagctggg accgtgagct gctcagaatg agacctctcg ctctccgtcc | 660 |
| ctgcaattca ctgctctcaa tttcattcct ctccctccaa ctcgcctgtt cggctgaaag | 720 |
| ccacaagggc ttgggcgcgg tagcaagaca gggcttcagg agtctgagaa aggaattcag | 780 |
| aatccgggcc cagtaaagga cacaagacag ttcgagacat aaataaggag agtctccagc | 840 |
| gcgagaggga cagaaatacc aacacacagg tgaaagaaca gatttgtgag agatagggtg | 900 |
| agaaaggcga tgagaacgag gtgaccagaa gtgggataag ga | 942 |

<210> SEQ ID NO 8
<211> LENGTH: 950
<212> TYPE: DNA
<213> ORGANISM: Homo sapiens

<400> SEQUENCE: 8

| | |
|---|---|
| aagatatggc taggatttta cttggcctga gatggtgata gcaattgact aagttcatca | 60 |
| gctacattat gtacacagag acattaaacc tgacaatata ctgatggata tgaatggaca | 120 |
| tattcggtta gcagatttgg ttcttgtctg aagctgatgg aagatggaac ggttcagtcc | 180 |
| tcagtggctg taggaactcc agattatatc tctcctgaaa tccttcaagc catgaagat | 240 |
| ggaaaaggga gatatggacc tgaatgtgac tggtggtctt gggggtctgt atgtatgaaa | 300 |

```
tgctttacgg agaaacacca ttttatgcag aatcgctggt ggagacatac ggaaaaatca      360
tgaaccacaa agagaggttt cagtttccag cccaagtgac tgatgtgtct gaaaatgcta      420
aggatcttat tcgaaggctc atttgtagca gagaacatcg acttggtcaa atggaatag       480 aagactttaa gaaacaccca tttttcagtg gaattgattg ggataatatt cggaactgtg      540
aagcacctta tattccagaa gttagtagcc aaagatacat cgaatttgat gtagatgatg      600
attgttgaaa acattctga aaaagatgcc ccacactcaa agaatactgg attttttctgg      660 ccaccaactg catttgtggt ttacatataa ctagttactg tggtccttct gaacggcgcg      720
tctagagtac cgctggtcca ctcacgacct gatggtagtc agaggatcta aaacaattag      780
aacgacgttt gagaaaatta ggctgagcaa acgtcaacg cgaagatcga gtacaaacgc       840
agcccactac ggtgggccac gcagaatgaa catataaagg acaacaacac ttggcatgaa      900
cgggaagatc aacgcaaaaa ataggtcaac acatacacga acgccgccgc                 950
```

<210> SEQ ID NO 9
<211> LENGTH: 552
<212> TYPE: DNA
<213> ORGANISM: Homo sapiens

<400> SEQUENCE: 9

```
tatatttagg gtcacagctt cccagctctc agcatctaat aacaaatgtt caatcctgat       60
gctagcagac actgagaatg agaagaataa gtgggtggga gtgctgagtg aattgcacaa      120
gattttgaag aaaaacaaat tcagagaccg ctcagtctat gttcccaaag aggcttatga      180
cagcactcta cccctcatta aaacaaccca ggcagccgca atcatagatc atgaaagaat      240
tgctttggga aacgaagaag ggttatttgt tgtacatgtc accaagatg aaattattag       300 agttggtgac aataagaaga ttcatcagat tgaactcatt ccaaatgatc agcttgttgc      360
tgtgatctca ggacgaaatc gtcatgtacg actttttcct atgtcagcat ggatgggcg       420 agagaccgat ttttacaagc tgtcagaaac taaagggtgt caaaccgtaa cttctggaaa      480
ggtgcgccat ggagctctca catgcctgtg tgtggctatg aaaaggcagg tcctctgtta      540
tgaactattt ca                                                          552
```

<210> SEQ ID NO 10
<211> LENGTH: 831
<212> TYPE: DNA
<213> ORGANISM: Homo sapiens

<400> SEQUENCE: 10

```
agattttact tggctgagat ggtgatagca agttgactaa gttcatcagc tacattatgt       60
acacagagac attaaacctg acaatatact gatggatatg aatggacata ttcggttagc      120
agatttggtt cttgtctgaa gctgatgaa gatggaacgg ttcagtcctc agtggctgta      180
ggaactccag attatatctc tcctgaaatc cttcaagcca tggaagatgg aaaagggaga     240
tatggacctg aatgtgactg gtggtcttgg gggtctgtat gtatgaaatg ctttacggag     300
aaacaccatt ttatgcagaa tcgctggtgg agacatacgg aaaaatcatg aaccacaaag     360
agaggtttca gtttccagcc caagtgactg atgtgtctga aaatgctaag gatcttattc     420
gaaggctcat ttgtagcaga gaacatcgac ttggtcaaac atggaataga agactttaag     480
aaacacccat ttttcagtgg aatcgatggg ataatattcg gaactgtgaa gcaccttata     540
ttccagaagt tagtagcccc aacagataca tcgaatttcg atgtacgatg attgattcgt     600
```

```
gtgacaaaca attcttgaaa cgatgcccccc gacaaaaaca tactgcattt tctggccacc      660
atctgccata ggtcggtcta tacatatact agtagctgtg tactttctga tcggaagctg      720
gttgaagaat tcacggttgg tcccaccttc agagggattc ctggcatgtg accgttccga      780
ggactctaga cacaaacctt agcacactga caggcttctg cacgacaaa c                831
```

<210> SEQ ID NO 11
<211> LENGTH: 546
<212> TYPE: DNA
<213> ORGANISM: Homo sapiens

<400> SEQUENCE: 11

```
agaaacatta caataagcg gcgttattcc ttcagagtcc cagaagagga aaggatgcag       60
cagaggaggg aaatgctacg agatccagaa atgagaaata aattaatttc taatccaact      120
aattttaatc acatagcaca catgggtcct ggagatggaa tacagatcct gaaagatctg      180
cccatgaacc ctcggcctca ggaaagtcgg acagtattca gtggctcagt cagtattcca      240
tctatcacca aatcccgccc tgagccaggc cgctccatga gtgctagcag tggcttgtca      300
gcaaggtcat ccgcacagaa tggcagcgca ttaaagaggg aattctctgg aggaagctac      360
agtgccaagc ggcagcccat gccctccccg tcagagggct ctttgtcctc cggaggcatg      420
gaccaaggaa gtgatgcccc agcgagggac tttgacggag aggactctga ctctccgagg      480
catttcacag ctttcaacag tttcaaccta agcagccccc ccaagcccag cttcaccccc      540
aaaaaa                                                                 546
```

<210> SEQ ID NO 12
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 12

```
agtttttat ttctaaatct tgcttgctg ttagtggacc atcaacagtt gaatactgca        60
gagcttggac agtctgtgtt gactcttgaa gttttctact gagttcaagt tttttcttgct     120 caaggcgctt aattcttctt tcataagctt cagttgctaa gttgttgtct agagtcctct      180
gaacattaac atcaagatcc agtgaggtgg gaccagccgt aactcttaaa cagctccgat      240
cagaaagtac acagctacta gtatatgtaa aacccaacan atggcagatg ggtgccagaa      300
aatgcagtat gtgttggtgg ggcatcgttt cagaattttt aaacaatcat catctacatc      360
aaaattcgat gtatctgttg ngctactaac ttctggaata taaggtgctt cacagttccg      420
aatattatcc caatcaattc cactgaanaa atgggtgtnt cttanagtct tctattccat      480
tttgaccaag tcgatgtctc tgctacaaat gagccttcga aatagatcct tagcattttc      540
agacacatca gtcacttggg ctgganactg aaacctctct tttgggtc                   588
```

<210> SEQ ID NO 13
<211> LENGTH: 507
<212> TYPE: DNA
<213> ORGANISM: Homo sapiens

<400> SEQUENCE: 13

```
tatttctaaa tctttgcttg ctgttagtgg accatcaaca gttgaatact gcagagcttg       60
gacagtctgt gttgactctt gaagttttct actgagttca gttttttctt gctcaaggcg     120
```

```
cttaattctt ctttcataag cttcagttgc taagttgttg tctagagtcc tctgaacatt     180
aacatcaaga tccagtgagg tgggaccagc cgtaactctt aaacagctcc gatcagaaag     240
tacacagcta ctagtatatg taaaaccaac aaatggcaga tggtggccag aaaatgcagt     300
atgtgttggt gggggcatcg tttcagaatt ttttaaacaa tcatcatcta catcaaaatt     360
cgatgtatct gttgggctac taacttctgg aatataaggt gcttcacagt tccgaatatt     420
atcccaatca attccactga aaaatgggtg tttcctaaag tcttctattc aattttgacc     480
aagtcgatgt tctctgctac aaatgag                                         507

<210> SEQ ID NO 14
<211> LENGTH: 686
<212> TYPE: DNA
<213> ORGANISM: Homo sapiens
<220> FEATURE:
<221> NAME/KEY: misc_feature
<222> LOCATION: (1)...(686)
<223> OTHER INFORMATION: n = A,T,C or G

<400> SEQUENCE: 14
aagtttttta tttctaaagc tttgcttgct gttagtggac catcaacagt tgaatactgc      60
agagcttgga cagtctgtgt tgactcttga agtttctac tgagttcaag ttttctttgc      120
tcaaggcgct taattcttct ttcataagct tcagttgcta agttgttgtc tagagtcctc     180
tgaacattaa catcaagatc cagtgaggtg ggaccagccg taactcttaa acagctccga     240
tcagaaagta cacagctact agtatatgta aacccaacaa atggcagatg gtggccagaa     300
aatgcagtat gtgttggtgg nggcatcgtt tcagaatttt ttaaacatca tcatctacat     360
caaaattcga tgtatctgtt gggctactaa cttctggaat ataggtgctt cacagttccg     420
aatattatcc ccatccaatt ccactggaaa atgggtggt ttcttaaagt cttctattcc     480
attttgacca gtccgatgt ctctgctaca aatgagccct tcgaattaga atcttagcat     540
tttcagacac atcagtcacc ttggcctgga aactgaaacc cttcttnggg ggtcatgatt     600
tttcccgaat gcctccccag cgatcctgct taaatggggg ttcttcctaa aagctattta     660
tacataacga ccccccaagga acacca                                         686

<210> SEQ ID NO 15
<211> LENGTH: 469
<212> TYPE: DNA
<213> ORGANISM: Homo sapiens
<220> FEATURE:
<221> NAME/KEY: misc_feature
<222> LOCATION: (1)...(469)
<223> OTHER INFORMATION: n = A,T,C or G

<400> SEQUENCE: 15
cacgaggctg agtgaattgc acaagatttt gaagaaaaac aaattcagag accgctcagt      60
ctatgttccc aaagaggctt atgacagcac tctacccctc attaaaacaa cccaggcagc     120
cgcaatcata gatcatgaaa gaattgcttt gggaaacgaa gaagggttat ttgttgtaca     180
tgtcaccaaa gatgaaaatta ttagagttgg tgacaataag aagattcatc agattgaact     240
cattccaaat gatcagcttg ttgctgtgat ctcaggacga atcgtcatg tacgactttt      300 tcctatgtca gcattggatg ggcgagagac cgattttac aagctgtcag aaactaaagg     360
gtgtcaaacc ataacttctg gaaggtgcg ccatggagct ctcacatgcc tgtgtgtggc     420
tatgaaaagg caggtcctct gttatgaact atntcagagc aagaccgt                 469
```

<210> SEQ ID NO 16
<211> LENGTH: 462
<212> TYPE: DNA
<213> ORGANISM: Homo sapiens

<400> SEQUENCE: 16

```
gccggtccca gttacaacag ctgaagaaag ggtggcagag agcactggct atagtgtgtg      60
acttcaaact ctttctgtac gatattgctg aaggaaaagc atctcagccc agtgttgtca     120
ttagtcaagt gattgacatg agggatgaag aattttctgt gagttcagtc ttggcttctg     180
atgttatcca tgcaagtcgg aaagatatac cctgtatatt tagggtcaca gcttcccagc     240
tctcagcatc taataacaaa tgttcaatcc tgatgctagc agacactgag aatgagaaga     300
ataagtgggt gggagtgctg agtgaattgc acaagatttt gaagaaaaac aaattcagag     360
accgctcagt ctatgttccc aaagaggctt atgacagcac tctacccctc attaaaacaa     420
cccaggcagc cgcaatcata gatcatgaaa gaattgcttt gg                        462
```

<210> SEQ ID NO 17
<211> LENGTH: 470
<212> TYPE: DNA
<213> ORGANISM: Homo sapiens
<220> FEATURE:
<221> NAME/KEY: misc_feature
<222> LOCATION: (1)...(470)
<223> OTHER INFORMATION: n = A,T,C or G

<400> SEQUENCE: 17

```
aagttttta tttctaaatc tttgcttgct gttagtggac catcaacagt tgaatactgc       60
aganttggac agtctgtgtt gactcttgaa gttttctact gagttcaagt ttttcttgct     120
caaggcgctt aattcttctt tcataagctt cagttgctaa gttgttgtct agagtcctct     180
gaacattaac atcaagatcc agtgaggtgg gaccagccgt aactcttaaa cagctccgat     240
cagaaagtac acagctacta gtatatgtaa aaccaacaaa tggcagatgg tggccagaaa     300
atgcagtatg tgttggtggg ggcatcgttt cagaatttt taaacaatca tcatctacat      360
caaaattccg atgtatctgt tgggctacta acttctgaa tataaggtgc ttcacagttc      420
cgaatattat cccaatcaat tccactgaaa atgggtgtt tcttaaagtc                 470
```

<210> SEQ ID NO 18
<211> LENGTH: 560
<212> TYPE: DNA
<213> ORGANISM: Homo sapiens
<220> FEATURE:
<221> NAME/KEY: misc_feature
<222> LOCATION: (1)...(560)
<223> OTHER INFORMATION: n = A,T,C or G

<400> SEQUENCE: 18

```
gaaatgcttt acggagaaac accatttat gcagaatcgc tggtggagac atacggaaaa       60
atcatgaacc acaagagag gtttcagttt ccagcccaag tgactgatgt gtctgaaaat     120
gctaaggatc ttattcgaag gctcatttgt agcagagaac atcgacttgg tcaaaatgga     180
atagaagact ttaagaaaca cccattttc agtggaattg attgggataa tattcggaac     240
tgtgaagcac cttatattcc agaagttagt agcccaacag atacatcgaa ttttgatgta     300
gatgatgatt gtttaaaaaa ttctgaaacg atgcccccac caacacatac tgcattttct     360
ggccaccatc tgccatttgt tggttttaca tatctagtag ctgtgtcttc tgatnggact     420
gtttaagagt tcggctggtc cacctcactg ganttgatgt taatgtnaga ggctctagca     480
```

```
acaacttagc actgaantta tgaaagaaga attaacgctt ganaagaaac ttgactcagt    540
ngaaacttca gagntacaca                                                560
```

<210> SEQ ID NO 19
<211> LENGTH: 599
<212> TYPE: DNA
<213> ORGANISM: Homo sapiens
<220> FEATURE:
<221> NAME/KEY: misc_feature
<222> LOCATION: (1)...(599)
<223> OTHER INFORMATION: n = A,T,C or G

<400> SEQUENCE: 19

```
catctcaaaa taatttttt ttgttgacga taaatgtatc caagaccata attaataaat     60
ctggcaagaa ataggcctct gttgctagat attacatggt aactcacagc caggtacaat   120
gaaggactgt tttacctgtg tacataatgt agctgatgaa ctgagtcaat tgctatcacc   180
atctcagcca aataaaatct agccatatct tcaggcaatc tatcttcaaa tttgctgagt   240
agagtaagca aatccccacc aacataataa tccataacca ggtataagtt attgtcatcc   300
tggaaagcat agtgcaaggt tgtaatccat ttattgtctc cattcactaa tacatccctt   360
tcttcacgaa aacatgctgt ctcagctctt ttcagcattt cccatttatt caatattttc   420
atggcaaaca ctntatctgc attttttagt tttactacag caacctcccc aaaagctcct   480
cgaccaatca cctttaatat ttcaaagtct tctctatgtt atcggatttg tttcaattta   540
gaagtaaatg gtttaccccc tttctagtat tcgaaaatgt tcttctcttt tctcaatgg    599
```

<210> SEQ ID NO 20
<211> LENGTH: 24
<212> TYPE: DNA
<213> ORGANISM: Artificial Sequence
<220> FEATURE:
<223> OTHER INFORMATION: random oligonucleotide

<400> SEQUENCE: 20

```
tcaactgact agatgtacat ggac                                            24
```

<210> SEQ ID NO 21
<211> LENGTH: 20
<212> TYPE: DNA
<213> ORGANISM: Homo sapiens

<400> SEQUENCE: 21

```
gaatacgcct accgatgctc                                                 20
```

<210> SEQ ID NO 22
<211> LENGTH: 20
<212> TYPE: DNA
<213> ORGANISM: Homo sapiens

<400> SEQUENCE: 22

```
ctgcctttgc tagctggagt                                                 20
```

```
<210> SEQ ID NO 23
<211> LENGTH: 26
<212> TYPE: DNA
<213> ORGANISM: Homo sapiens

<400> SEQUENCE: 23
tggatcaatt tgaacgctct ccatcc                                              26
```